(12) United States Patent
Harman et al.

(10) Patent No.: US 6,512,166 B1
(45) Date of Patent: *Jan. 28, 2003

(54) COMBINATIONS OF FUNGAL CELL WALL DEGRADING ENZYME AND FUNGAL CELL MEMBRANE AFFECTING COMPOUND

(75) Inventors: Gary E. Harman, Geneva, NY (US); Matteo Lorito, Salerno (IT); Antonio Di Pietro, Cordoba (ES); Christopher K. Hayes, Geneva, NY (US); Felice Scala, Sorrento (IT); Christian P. Kubicek, Vienna (AT)

(73) Assignee: Cornell Research Foundation, Inc., Ithaca, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 08/611,504

(22) Filed: Mar. 5, 1996

Related U.S. Application Data

(63) Continuation-in-part of application No. 08/499,164, filed on Jul. 7, 1995, now abandoned, which is a continuation of application No. 08/249,927, filed on May 26, 1994, now Pat. No. 5,433,947, which is a continuation of application No. 07/990,609, filed on Dec. 15, 1992, now Pat. No. 5,326,561, application No. 08/611,504, which is a continuation-in-part of application No. 08/371,680, filed on Dec. 21, 1994, now Pat. No. 6,020,540, which is a continuation-in-part of application No. 08/045,269, filed on Apr. 14, 1993, now Pat. No. 5,378,821, which is a continuation-in-part of application No. 07/919,784, filed on Jul. 27, 1992, now Pat. No. 6,251,390, which is a continuation-in-part of application No. 07/716,134, filed on Jun. 17, 1991, now Pat. No. 5,173,419.
(60) Provisional application No. 60/007,567, filed on Nov. 27, 1995.

(51) Int. Cl.⁷ ............................ A01H 5/00; G12N 15/82
(52) U.S. Cl. ........................ 800/301; 514/12; 800/279
(58) Field of Search ................... 424/94.61; 435/200, 435/209, 254.1, 256.7, 69.1, 320.1, 419, 468; 514/396, 423, 359, 256; 800/301, 298, 278, 279; 536/23.2, 23.6

(56) References Cited

U.S. PATENT DOCUMENTS

| | | | |
|---|---|---|---|
| 4,477,433 A | 10/1984 | Hultman | 435/254 |
| 4,489,161 A | 12/1984 | Papavizas | 435/254 |
| 4,686,185 A | 8/1987 | Wakunaga et al. | |
| 4,751,081 A | 6/1988 | Suslow et al. | 424/93 |
| 4,940,840 A * | 7/1990 | Suslow et al. | 800/205 |
| 5,137,819 A | 8/1992 | Kilburn et al. | |
| 5,168,064 A | 12/1992 | Bennett et al. | |
| 5,173,419 A * | 12/1992 | Harman et al. | |
| 5,187,262 A | 2/1993 | Raikhel et al. | |
| 5,188,961 A | 2/1993 | Overbye et al. | |
| 5,202,247 A | 4/1993 | Kilburn et al. | |
| 5,238,843 A | 8/1993 | Carpenter et al. | |
| 5,258,304 A * | 11/1993 | Carpenter et al. | 435/264 |
| 5,258,502 A | 11/1993 | Kuranda | |
| 5,290,687 A * | 3/1994 | Suslow et al. | 435/69.1 |
| 5,326,561 A * | 7/1994 | Harman et al. | 424/94.61 |
| 5,328,999 A | 7/1994 | Bennett et al. | |
| 5,340,731 A | 8/1994 | Kilburn et al. | |
| 5,348,743 A | 9/1994 | Ryals et al. | |
| 5,350,689 A | 9/1994 | Shillito et al. | |
| 5,352,607 A | 10/1994 | Laine et al. | |
| 5,356,803 A | 10/1994 | Carpenter et al. | |
| 5,360,608 A * | 11/1994 | Harman et al. | 424/94.61 |

(List continued on next page.)

FOREIGN PATENT DOCUMENTS

| | | |
|---|---|---|
| DE | 4117026 | 11/1992 |
| EP | 339009 | 10/1989 |
| EP | 418695 | 3/1991 |
| EP | 425016 A2 | 5/1991 |
| EP | 462065 A2 | 12/1991 |
| EP | 0531218 * | 4/1992 |
| EP | 531218 A1 | 3/1993 |
| JP | 63-123645 | 5/1988 |
| JP | 2-28608 | 1/1990 |
| JP | 5084087 | 4/1993 |
| JP | 6046849 | 2/1994 |
| WO | WO 90/03732 | 4/1990 |
| WO | WO 90/07001 * | 6/1990 |
| WO | WO 92/01792 | 2/1992 |
| WO | 9201792 * | 2/1992 |
| WO | WO9402598 | 2/1994 |
| WO | WO 94/13784 | 6/1994 |
| WO | WO 94/17667 | 8/1994 |
| WO | WO 94/24271 | 10/1994 |
| WO | WO 94/24288 | 10/1994 |
| WO | WO 95/00652 | 1/1995 |
| WO | WO 95/19443 | 7/1995 |
| WO | WO 96/36700 | 11/1996 |

OTHER PUBLICATIONS

Watanabe et al. Agric. Biol. Chem. 52(4):895–901, 1988 (AR14).*

Roberts et al. (AT9) J. Gen. Microbiol. 136:1771–1778, 1990.*

(List continued on next page.)

*Primary Examiner*—Amy J. Nelson
(74) *Attorney, Agent, or Firm*—Nixon Peabody LLP

(57) ABSTRACT

A system for inhibiting the germination or growth of a fungus comprises (a) fungal cell wall degrading chitinolytic or glucanolytic enzyme and (b) antifungal cell membrane affecting: compound. Exemplified antifungal fungal cell membrane affecting compounds include flusilazole, miconazole, osmotin, gramicidin, valinomycin, phospholipase B, and trichorzianines. The system components (a) and (b) may be supplemented with polyene macrolide antibiotic, antifungal epithiodiketopiperazine antibiotic (e.g., gliotoxin), fungal cell wall biosynthesis inhibitor (e.g., L-sorbose) and/or detergent. Embodiments include method of contacting a plant which expresses cell wall degrading enzyme with antifungal fungal cell membrane affecting compound.

17 Claims, 17 Drawing Sheets

U.S. PATENT DOCUMENTS

| | | | |
|---|---|---|---|
| 5,378,821 A | * | 1/1995 | Harman et al. |
| 5,395,541 A | | 3/1995 | Carpenter et al. |
| 5,399,680 A | | 3/1995 | Zhu et al. |
| 5,433,947 A | * | 7/1995 | Harman et al. .......... 424/94.61 |
| 5,446,138 A | * | 8/1995 | Blaiseu et al. |
| 5,474,926 A | | 12/1995 | Harman et al. ............. 435/200 |
| 5,514,779 A | | 5/1996 | Broekaert et al. |
| 5,516,674 A | | 5/1996 | Lawrence et al. |
| 5,529,919 A | | 6/1996 | Knowles et al. |
| 5,530,187 A | | 6/1996 | Lamb et al. |
| 5,538,525 A | | 7/1996 | Broekaert et al. |
| 5,539,095 A | | 7/1996 | Sticklen et al. |
| 5,550,046 A | | 8/1996 | Suzuki et al. |
| 5,554,743 A | | 9/1996 | Bennett et al. |
| 5,561,051 A | | 10/1996 | Silverman |
| 5,563,328 A | | 10/1996 | Mitra et al. |
| 5,569,597 A | | 10/1996 | Grimsley et al. |
| 5,569,830 A | | 10/1996 | Bennett et al. |
| 5,585,545 A | | 12/1996 | Bennett et al. |
| 5,597,946 A | | 1/1997 | Jaynes et al. |
| 5,633,450 A | * | 5/1997 | Suslow et al. ............... 800/205 |
| 5,670,706 A | * | 9/1997 | Cornelissen et al. ........ 800/205 |

OTHER PUBLICATIONS

Mishra et al. (AT11) PNAS (USA) 69(2):313–317 (1972).*

Poulose, A.J., (AS2) "Biotechnology & Fungal Control", In: Target Sites of Fungicide, Koller, ed., CRC Press, Boca Raton, Florida 1992, pp. 313, 314, 317.*

Stam M, et al. "The silence of genes in transgenic plants," Ann. Bot. 79: 3–12, 1997.*

Koziel MG, et al. "Optimizing expression of transgenes with an emphasis on post–transcriptional events." Plant Mol. Biol. 32: 393–405, 1996.*

Smith CJS, et al. "Antisense RNA inhibition of polygalacturonase gene expression in transgenic tomatoes." Nature 334: 724–726, Aug. 25, 1988.*

Kless H, et al. "Cloning of the gene coding for chitobiase of *Serratia marcenscens.*" Mol. Gen. Genet. 217: 471–473 (Abstract only), 1989.*

Robbins PW, et al. "Primary structure of the *Streptomyces–plicatus* enzyme endo–beta–N–acetylglucosaminidase." JBC 259: 7577–7583 (Abstract only), 1984.*

Sperisen C, et al. "Comparison of cloned genes provides evidence for intergenomic exchange of DNA in the evolution of a tobacco glucan endo–1,3–beta–blucosidase gene family." PNAS 88:1820–1824, Mar. 1990.*

Broglie, K. et al., "Transgenic Plants with Enhanced Resistance to the Fungal Pathogen *Rhizoctonia solani.*" 1991, Science, vol. 254, pp. 1194–1197.*

Blaiseau, P. and Lafay, J., "Primary structure of a chitinase–encoding gene (chiI)from the filamentous fungus *Aphanocladium album:* similarity to bacterial chitinases." 1992, Gene, vol. 120, pp. 243–248.*

Howie, W. et al., "Transgenic tobacco plants which express the chiA gene from *Serratia marcescens* have enhanced tolerance to *Rhizoctonia solani.*" 1994, Transgenic Research, vol. 3, pp. 90–98.*

Draborg, H. et al., "Molecular cloning and expression in *S Cerevisiae* of two exochitinases from *Trichoderma Harzianum.*" 1995, Biochemistry and Molecular Biology Int'l., vol. 36, pp. 781–791.*

Zhu, Q. et al., "Enhanced Protection Against Fungal Attack by Constitutive Co–expression of Chitinase and Glucanase Genes in Transgenic Tobacco." 1994, Bio/Technology, vol. 12, pp. 807–812.*

Schaeffer, H. et al., "Cloning and Targeted Gene Disruption of EXG1, Encoding Exo–B1,3–Glucanase, in the Phytopathogenic Fungus *Cochliobolus carbonum.*" 1994, Applied and Environmental Microbiology, vol. 60, pp. 594–598.*

Hayes et al, "Isolation and Sequence Of An Endochitinase–Encoding Gene From A cDNA Library of *Trichoderma harzianum,*" Gene, 138:143–148 (1994).

Harikrishna et al., "An Endochitinase Gene Expressed at High Levels in the Styler Transmitting Tissues of Tomatoes," *Plant Molecular Biology,* 30:899–911 (1996).

Chen et al., "Analysis of Ethylene Signal–Transduction Kinetics Associated with Seedling–Growth Response and Chitinase Induction in Wild–Type and Mutant Arabidopsis," *Plant Physiol.,* 108:597–607 (1995).

Jach et al., "Enhanced Quantitative Resistance Against Fungal Disease by Combinatorial Expression of Different Barley Antifungal Proteins in Transgenic Tobacco," *The Plant Journal,* 8(1):97–109 (1995).

Limón et al., "Primary Structure and Expression Pattern of the 33–kDa Chitinase Gene From the Mycoparasitic Fungus *harzianum,*" *Curr. Genet,* 28:478–483 (1995).

Spaink et al., "Rhizobium NodI and NodJ Proteins Play a Role in the Efficiency of Secretion of Lipochitin Oligosaccharides," *Journal of Bacteriology,* 177(21):6276–6281 (1995).

Perlick et al., "The Broad Bean Gene VfNOD32 Encodes a Nodulin with Sequence Similarities to Chitinase That Is Homologous to $(\alpha/\beta)_8$–Barrel–Type Seed Proteins," *Plant Physiol.,* 110:147–154 (1996).

Kellmann et al., "Characterization of Two Class II Chitinase Genes From Peanut and Expression Studies in Transgenic Tobacco Plants," *Plant Molecular Biology,* 30:351–358 (1996).

Didierjean et al., "Heavy–Metal–Responsive Genes in Maize: Identification and Comparison of Their Expression Upon Various Forms of Abiotic Stress," *Planta,* 199:1–8 (1996).

Turóczi et al., "Biological and Molecular Characterization of Potential Biocontrol Strains of Trichoderma," *J. Basic Microbiol.,* 36(1):63–72 (1996).

Xu et al., Regulation, Expression and Function of a New Basic Chitnase Gene in Rice (*Oryza sativa* L.), *Plant Molecular Biology,* 30:387–401 (1996).

Hanfrey et al., "Leaf Senescence in *Brassica napus:* Expression of Genes Encoding Pathogenesis–Related Proteins," *Plant Molecular Biology,* 30:597–609 (1996).

Hartland et al., "The Linkage of (1–3)–β–Glucan to Chitin During Cell Wall Assembly in *Saccharomyces cerevisiae,*" *Yeast,* 19:1591–1599 (1994).

García et al., "Cloning and Characterization of a Chitinase (CHIT42) cDNA From the Mycoparasitic Fungus *Trichoderma harzianum,*" *Curr Genet.,* 27:83–89 (1994).

Lorito et al., "Potential of Genes and Gene Products from Trichoderma sp and Gliocladium sp. For the Development of Biological Pesticides," *Molecular Biotechnology,* 2:209–217 (1994).

Perrakis et al., "Crystal Structure of a Bacterial Chitinase At 2.3 Å Resolution," *Current Biology,* 2:1169–1180 (1994).

Meins et al., "Gene Silencing in Transgenic Plants: A Heuristic Autoregulation Model," *Current Topics in Microbiology and Immunology,,* 105–120 (1995).

Berglund et al., "A Proline–Rich Chitinase From *Beta vulgaris,*" *Plant Molecular Biology,* 27:211–216 (1995).

Araki et al., "Structural Classification of Plant Chitinases: Two Subclasses in Class I and Class II Chitinases," *Biosci. Biotech. Biochem.*, 59(2):336–338 (1995).

Shinshi et al., "Identification of An Ethylene–Responsive Region in the Promoter of a Tobacco Class I Chitinase Gene," *Plant Molecular Biology*, 27:923–932 (1995).

Van Kan et al., Induction of Tomato Stress Protein mRNAs By Ethephon, 2,6–dichloroisonicotinic Acid and Salicylate, *Plant Molecular Biology*, 27:1205–1213 (1995).

Chang et al., "Molecular Cldoning and Characterization of a Pea Chitinase Gene Expressed in Response to Wounding, Fungal Infection and The Elicitor Chitosan," *Plant Molecular Biology*, 28:105–111 (1995).

Semino et al., "Synthesis of "Nod"–like Chitin Oligosaccharides by the Xenopus Development Protein DG42," *Proc. Natl. Acad., Sci.*, 92:3498–3501 (1995).

Benhamou, "Immunocytochemistry of Plant Defense Mechanisms Induced Upon Microbial Attack," *Microscopy Research and Technique*, 31:63–78 (1995).

Samac et al., "Effect of Chitinase Antisense RNA Expression On Disease Susceptibility of Arabidopsis Plants," *Plant Molecular Biology*, 25:587–596 (1994).

Gaffney et al., "Global Regulation of Expression of Antifungal Factors by a *Pseudomonas fluorescens* Biological Control Strain," *Molecular Plant–Microbe Interactions*, 7:455–463 (1994).

Wu et al., "Molecular Analysis of Two cDNA Clones Encoding Acidic Class I Chitinase in Maize," *Plant Physiol.*, 105:1097–1105 (1994).

Clarke et al,. "Wound–Induced and Developmental Activation of a Poplar Tree Chitinase Gene Promoter in Transgenic Tobacco," *Plant Molecular Biology*, 15:799–815 (1994).

Koby et al., "The Chitinase Encoding Tn7–Based chiA Gene Endows *Pseudomonas fluorescens* With the Capacity to Control Pathogens In Soil," *Gene*, 147:81–83 (1994).

Brurberg et al., "Expression of a Chitinase Gene From *Serratia marcescens* In *Lactococcus lactis* and *Lactobacillus plantarum*," *Appl Microbiol Biotechnol*, 42:108–115 (1994).

Mylona et al., "The Root Epideremis–Specific Pea Gene RH12 is Homologous To a Pathogenesis–Related Gene," *Plant Molecular Biology*, 26:39–50 (1994).

Leah et al., "Identification of An Enhancer/Silencer Sequence Directing the Aleurone–Specific Expression of a Barley Chitinase Gene," *The Plant Journal*, 6:579–589 (1994).

Heitz et al., "Molecular Characterization of a Novel Tobacco Pathogenesis–Related (PR) Protein: A New Plant Chitinase/ Lysozyme," *Mol Gen Genet*, 245::246–254 (1994).

Beerhues et al., "Primary Structure and Expression Of mRNAs Encoding Basic Chitinase and 1,3–β–Glucanase in Potato," *Plant Molecular Biology,*, 24:353–367 (1994).

Ponstein et al., "A Novel Pathogen– and Wound–Inducible Tobacco (*Nicotiana tabacum*) Protein With Antifungal Activity," *Plant Physiol.*, 104:109–118 (1994).

Lawton et al., "Regulation of Cucumber Class III Chitinase Gene Expression," *Molecular Plant–Microbe Interactions*, 7:48–57 (1994).

Yamagami et al., The Complete Amino Acid Sequence of Chitinase–a From the Seeds of Rye (*Secale cereal*), *Biosci. Biotech. Biochem.*, 58:322–329 (1994).

Fukuda et al., "Characterization of a Novel cis–acting Element That Is Responsive To a Fungal Elicitor In the Promoter of A Tobacco Class I Chitinase Gene," *Plant Molecular Biology,*, 24:485–493 (1994).

Holm et al., "Structural Similarity of Plant Chitinase and Lysozymes From Animals and Phage– An Evolutionary Connection," *FEBS Letters*, 340:129–132 (1994).

Staehelin et al., "Perception of Rhizobium Nodulation Factors By Tomato Cells and Inactivation By Root Chitinases," *Proc. Natl. Acad. Sci. USA*, 91:2196–2200 (1994).

Melchers et al., A New Class of Tobacco Chitinases Homologous To Bacterial Exo–Chitinases Displays Antifungal Activity, *The Plant Journal*, 5:469–480 (1994).

Nielsen et al., A Hydroxyproline–Containing Class IV Chitinase of Sugar Beets is Glycosylated With Xylose, *Plant Molecular Biology*, 25:241–257 (1994).

Chet et al., "Biological Control of Rungal Pathogens," *Applied Biochemistry and Biotechnology*, 48:37–43 (1994).

Faure–Raynaud, M., "Determination of the Chitinolytic Activity of *Abies Alba* Mill. Litter Microorganisms: Bacteria and Yeasts," *Ann. Microbiol.*, 132:267–279 (1981).

Harpster et al., "Relative Strengths of the 35S Califlower Mosaic Virus, 1', 2', and Nopaline Synthase Promoters in Transformed Tobacco Sugarbeet and Oilseed Rape Callus Tissue," *Mol Gen Genet*, 212:182–190 (1988).

Gaynor, John J., "Primary Structure of An Endochitinase mRNA From *Solanum tubersum,"* Nucleic Acids Research*, 16:5210 (1988).

Metraux et al., "Isolation of a Complementary DNA Encoding a Chitinase With Structural Homology To a Bifunctional Lysozyme/Chitinase," *Proc. Natl. Acad. Sci. USA*, 86:896–900 (1989).

Harpster et al., "Nucleoside Sequence of the Chitinase B Gene of *Serratia marcescens,"* Nucleic Acids Research*, 17:5395 (1989).

Gaynor et al., "Sequence Analysis of a Genomic Clone Encoding An Endochitinase from *Solanum tubersum,"* Nucleic Acids Research*, 17:5855–5856 (1989).

Payne et al., "Isolation of Complementary DNA Clones Encoding Pathogenesis–Related Proteins P and Q, Two Acidic Chitinases From Tobacco," *Proc. Natl. Acad. Sci. USA*, 87:98–102 (1990).

Ori et al., A Major Stylar Matrix Polypeptide (sp41) is a Member of the Pathogenesis–Related Proteins Superclass, *The EMBO Journal*, 9:3429–3236 (1990).

Linthorst et al., "Analysis of Gene Families Encoding Acidic and Basic β–1,3–Glucanases of Tobacco," *Proc. Natl. Acad. Sci. USA*, 87:8756–8760 (1990).

Herget et al., "Elicitor–Specific Induction of One Member of the Chitinase Gene Family in *Arachis hypogaea,"* Mol Gen Genet.*, 224:469–476 (1990).

Henrissat, "Weak Sequence Homologies Among Chitinases Detected By Clustering Analysis," *Proteins Seq Data Anal.*, 3:523–526 (1990).

Leah et al., "Biochemical and Molecular Characterization of Three Barley Seed Proteins with Antifungal Properties," *The Journal of Biological Chemistry*, 266:1564–1573 (1991).

Zhu et al., "Isolation and Characterization of a Rice Gene Encoding a Basic Chitinase," *Mol Gen Genet*, 226:289–296 (1991).

De Bolle et al., "A Technique For Detecting Antifungal Activity of Proteins Separated by Polyacrylamide Gel Electrophoresis," *Electrophoresis*, 12:442–444 (1991).

Friedrich et al., "Pathogenesis–Related Protein 4 is Structurally Homologous To the Carboxy–Terminal Domains of Hevein, Win–1 and Win–2," *Mol Gen Genet,* 230:113–119 (1991).

Neuhaus et al., "A Short C–Terminal Sequence is Necessary and Sufficient For the Targeting of Chitinases to the Plant Vacuole," *Proc. Natl. Acad. Sci. USA,* 88:10362–10366 (1991).

Watanabe et al., "Structure of the Gene Encoding Chitinase D of *Bacillus circulans* WL–12 and Possible Homology of the Enzyme to Other Prokaryotic Chitinases and Class III Plant Chitinases," *Journal of Bacteriology,* 174:408–414 (1992).

Verburg et al., "Identification of an Essential Tyrosine Residue in the Catalytic Site of a Chitinase Isolated from *Zea mays* That Is Selectively Modified During Inactivation with 1–Ethyl–3–(dimethylaminopropyl)–carbodiimide," *The Journal of Biological Chemistry,* 267:3886–3893 (1992).

van Buuren et al., The Structure and Regulation of Homeologous Tobacco Endochitinase Genes of *Nicotiana sylvestris* and *N. Tomentosiformis* Origin, *Mol Gen Genet,* 232–460–469 (1992).

Hejgaard et al., Antifungal Activity of Chitin–Binding PR–4 Type Proteins From Barley Grain and Stressed Leaf, *FEBS Letters,* 307:389–392 (1992).

Flach et al., "What's New in Chitinase Research?," *Experientia,* 48:701–716 (1992).

Araki et al., "The Complete Amino Acid Sequence of Yam (*Diosorea japonica*) Chitinase," *The Journal of Biological Chemistry,,* 267:19944–19947 (1992).

Blaiseau et al., "Primary Structure of a Chitinase–Encoding Gene (chi1) From the Filamentous Fungus *Aphanocladium album:* Similarity to Bacterial Chitinases," *Gene,* 120:243–248 (1992).

Hart et al., "Regulated Inactivation of Homologous Gene Expression in Transgenic *Nicotiana sylvestris* Plants Containing a Defense–Related Tobacco Chitinase Gene," *Mol Gen Genet,* 235:179–188 (1992).

Ishige et al., "Cloning of a Complementary DNA That Encodes an Acidic Chitinase Which is Induced by Ethylene and Expression of the Corresponding Gene," *Plant Cell Physiol.,* 34:103–111 (1993).

Stintzi et al.,"Plant 'Pathogenesis–Related' Proteins and Their Role in Defense Against Pathogens," *Biochimie,* 75:687–706 (1993).

Hart et al., "A 61 bp Enhancer Element of the Tobacco β–1,3–Glucanase B Gene Interacts With One or More Regulated Nuclear Proteins," *Plant Molecular Biology,* 21:121–131 (1993).

Melchers et al., "Extracellular Targeting of the Vacuolar Tobacco Proteins AP24, Chitinase and β–1,3–Glucanase in Transgenic Plants," *Plant Molecular Biology,* 21:583–593 (1993).

Benhamou et al., "Antifungal Effect of Bean Endochitinase on *Rhizoctonia solani:* Ultrastructural Changes and Cytochemical Aspects of Chitin Breakdown," *Canadian Journal of Microbiology,* 39:318–328 (1993).

Sticher et al., "Posttranslational Processing of a New Class of Hydroxyproline–Containing Proteins," *Plant Physiol.,* 101:1239–1247 (1993).

Blaak et al., "Characteristics of An Exochitinase From *Streptomyces olivaceoviridis,* Its Corresponding Gene, Putative Protein Domains and Relationship to Other Chitinases," *Eur. J. Biochem.,* 214:659–669 (1993).

Tsujibo et al., "Site–Directed Mutagenesis of Chitinase From Alteromonas sp. Strain O–7," *Biosci. Biotech. Biochem.,* 57:1396–1397 (1993).

Iseli et al., "The N–Terminal Cysteine–Rich Domain of Tobacco Class I Chitinase Is Essential for Chitin Binding but Not for Catalyti Catalytic or Antifungal Activity," *Plant Physiol.,* 103:221–226 (1993).

Vogelsang et al., "Cloning of a Class III Acidic Chitinase from Chickpea," *Plant Physiol.,* 103:297–298 (1993).

Danhash et al., "Molecular Characterization of Four Chitinase cDNAs Obtained From *Cladosporium fulvum*–Infected Tomato," *Plant Molecular Biology,* 22:1017–1029 (1993).

Watanabe et al., "Identification of Glutamic Acid 204 and Aspartic Acid 200 in Chitinase A1 of *Bacillus circulans* WL–12 as Essential Residues for Chitinase Activity," *The Journal of Biological Chemistry,* 268:18567–18572 (1993).

Smigocki et al., "Cytokinin–Mediated Insect Resistance in Nicotiana plants Transformed With the ipt Gene," *Plant Molecular Biology,* 23:325–335 (1993).

Tsujibo et al., "Cloning and Sequence Analysis of the Gene Encoding a Thermostable Chitinase From *Streptomyces thermoviolaceus* OPC–520," *Gene,* 134:113–117 (1993).

Wemmer et al., "The Most Abundant Soluble Basic Protein of the Stylar Transmitting Tract in Potato (*Solanum tuberosum* L.) Is An Endochitinase," *Planta,* 194:264–273 (1994).

Laflamme et al., "Isolation of Nucleotide Sequence of cDNA Clones Encoding Potato Chitinase Genes," *Plant Molecular Biology,* 13:249–250 (1989).

Shinshi et al., "Structure of a Tobacco Endochitinase Gene: Evidence That Different Chitinase Genes Can Arise by Transposition of Sequences Encoding a Cysteine–Rich Domain," *Plant Molecular Biology,* 14:357–368 (1990).

Memelink et al., "Tobacco Genes Encoding Acidic and Basic Isoforms of Pathogenesis–Related Proteins Display Different Expression Patterns," *Plant Molecular Biology,* 14:119–126 (1990).

Bednarek et al., "The Barley Lectin Carboxyl–Terminal Propeptide Is a Vacuolar Protein Sorting Determinant in Plants," *The Plant Cell,* 3:1195–1206 (1991).

Neale et al., "Chitinase, β–1,3–Glucanase, Osmotin, and Extensin Are Expressed in Tobacco Explants During Flower Formation," *The Plant Cell,* 2:673–684 (1990).

Neuhaus et al., Mutation Analysis of the C–Terminal Vacuolar Targeting Peptide of Tobacco Chitinase: Low Specificity of the Sorting System, and Gradual Transition Between Intracellular Retention and Secretion Into the Extracellular Space, *The Plant Journal,* 5:45–54 (1994).

Nielsen et al., "An Acidic Class III Chitinase in Sugar Beet: Induction by *Cercospora beticola,* Characterization, and Expression in Transgenic Tobacco Plants," *Molecular Plant–Microbe Interactions,* 6:495–506 (1993).

Meier et al., "Spatial and Temporal Accumulation of Defense Gene Transcripts in Bean (*Phaseolus vulgaris*) Leaves in Relation to Bacteria–Induced Hypersensitive Cell Death," *Molecular Plant–Microbe Interactions,* 6:453–466 (1993).

Davis et al., "Populus Chitinase Genes: Structure, Organization, and Similarity of Translated Sequences to Herbaceous Plant Chitnases," *Plant Molecular Biology,* 17:631–639 (1991).

Margis–Pinheiro et al., "Isolation of a Complementary DNA Encoding the Bean PR4 Chitinase: An Acidic Enzyme with An Amino–Terminus Cysteine–Rich Domain," *Plant Molecular Biology,* 17:243–253 (1991).

Edington et al., "cDNA Cloning and Characterization of a Putative 1,3–β–D–Glucanase Transcript Induced by Fungal Elicitor in Bean Cell Suspension Cultures," *Plant Molecular Biology*, 16:81–94 (1991).

Neuhaus et al., "High–Level Expression of a Tobacco Chitinase Gene in *Nicotiana sylvestris*. Susceptibility of Transgenic Plants to *Cercospora nicotianae* Infection," *Plant Molecular Biology*, 16:141–151 (1991).

Ohme–Takagi et al., "Structure and Expression of a Tobacco β–1,3–Glucanase Gene," *Plant Molecular Biology*, 15:941–946 (1990).

Payne et al., "Evidence for a Third Structural Class of β–1,3–Glucanase in Tobacco," *Plant Molecular Biology*, 15:797–808 (1990).

Ernst et al., "Ozone–Induced Changes of mRNA Levels of β–1,3–Glucanase, Chitinase and 'Pathogenesis–Related' Protein lb in Tobacco Plants," *Plant Molecular Biology*, 20:673–682 (1992).

van Kan et al., "Differential Accumulation of mRNAs Encoding Extracellular and Intracellular PR Proteins in Tomato Induced by Virulent and Avirulent Races of *Cladosporium fulvum*," *Plant Molecular Biology*, 20:513–527 (1992).

Neuhaus et al., "The Function of Vacuolar β–1,3–Glucanase Investigated by Antisense Transformation. Susceptibility of Transgenic *Nicotiana sylvestris* Plants to *Cercospora nicotianae* Infection," *Plant Molecular Biology*, 19:803–813 (1992).

Lawton et al., "Acidic and Basic Class III Chitinase mRNA Accumulation in Response to TMV Infection of Tobacco," *Plant Molecular Biology*, 19:735–743 (1992).

Lund et al., "A Plant Signal Sequence Enhances the Secretion of Bacterial ChiA in Transgenic Tobacco," *Plant Molecular Biology*, 18:47–53 (1992).

Araki et al., "Amino Acid Sequences of the N–Terminal Domain of Yam (*Dioscorea japonica*) Aerial Tuber Acidic Chitinase. Evicence for the Presence of a Wheat Germ agglutinin Domain in Matured Acidic Chitinase from Unstressed Tuber," *Plant Molecular Biology*, 19:351–354 (1992).

Shapira et al., Control of Plant Diseases by Chitinase Expressed from Cloned DNA in *Escherichia Col.*, *Phytopatholy* 79(11):1246–1249 (1989).

Mauch et al., "Antifungal Hydrolases in Pea Tissue–II. Inhibition of Fungal Growth By Combinations of Chitinase and β–1,3–Glucanase," *Plant Physiol.*, 89:936–942 (1988).

Klemsdal et al., "Molecular Cloning of Chitinase Genes from *Trichoderma harzianum* Strain P1," 11th Nordic Postgraduate School in Plant Pathology (Feb. 1992).

Ulhoa et al., "Purification and Some Properties of the Extracellular Chitinase Produced by *Trichoderma harzianum*," Enzyme Microb. Technol. 14:236–240 (1992).

Arroyo–Begovich, "Chitinase from *Neurospora crassa*," Meth. in Enzymology, 161:471–474 (1988).

Pedraza–Reyes et al., "Chitinase Activity in Germinating Cells of *Mucor rouxii*," Antonie Van Leeunenhoek, 59(3):183:189.

Pedraza–Reyes et al., "Detection of Nine Chitinase Species in Germinating Cells of *Mucor rouxii*," Current Microbiology, 22(1):43–46 (1991).

Ohtakara et al., "Isolation of Chitinase and Chitobiase Produced by *Pycnoporus Cinnabarinus* and Their Properties," Chemical Abstracts, 95:7597 (1981).

Otakara et al., "Studies on the Chitinolytic Enzymes of Black–koji Mold," *Agr. Biol. Chem.*, 27(6):454–460 (1963).

Yabuki, Derwent Biotechnology Abstracts, 4(15) 85–07729 (1985) (abstract).

Yabuki, Derwent Biotechnology Abstracts, 4(15) 85–07730 (1985) (abstract).

Tronsmo, A., Aktuelt fra Statens Fagtjeneste for Landbruket 2., 107–113 (1985).

Sivan et al., "Degradation of Fungal Cell Walls by Lytic Enzymes of *Trichoderma harzianum*," *J. Gen. Microbiol.*, vol. 135(3):675–682, Biosis Abstract.

Sandhu et al., Use of Lytic Enzymes for Protoplast Production in *Trichoderma reesei* QM9414, Enzyme Microb. Technol., 11:21–25 (1989).

Usui et al., "Enzymic Synthesis of useful Cnito–oligosaccharides Utilizing Transglycosylation by Chitinolytic Enzymes in a Buffer Containing Ammonium Sulfate," *Carbohydrate Research*, 203:65–77 (1990).

De Vries et al., "Release of Protoplasts from *Schizophyllum commune* by Combined Action of Purified α–1,3–Glucanase and Chitinase Derived from *Trichoderma viride*," *Journal of General Microbiology*, 76:319–330 (1973).

Takara Biomedicals Brochure for Chitinase T–1, dated 4/89, (Portion translated).

Takara Biomedicals Brochure for β–N–Acetylhexosaminidase from *Trichoderma harzianum* AF6–T8, dated 4/89 (Portion translated).

De La Cruz et al., "Isolation and Characterization of Three Chitinases from *Trichoderma harzianum*," *Eur. J. Biochem.*, 206:859–867 (1992).

Kitamoto, Y. et al., "Purification and Some Properties of an Exo–β–1,3–glucanase from *Trichoderma harzianum*," *Agric. Biol. Chem.*, 51(12):3385–3386 (1987).

Ridout et al., "Enzyme Activity and Electrophoretic Profile of Extracellular Protein Induced in Trichoderma spp. by Cell Walls of *Rhizoctonia solani*," *Journal of General Microbiology*, 1323:2345–2352 (1986).

Tangarone et al., "Purification and Characterization of an Endo–(1,3)–β–D–Glucanase from *Trichoderma longibrachiatum*," *Applied and Environmental Microbiology*, 55:177–184 (1999).

Ulhoa et al., "Purification and Characterization of an Extracellular Chitobiase from *Trichoderma longibrachiatum*," Current Microbiology, 23:285–289 (1991).

Ulhoa et al., "Regulation of Chitinase Synthesis in *Trichoderma longibrachiatum*," *Journal of General Microbiology*, 137:2163–2169 (1991).

Methods in Enzymology, vol. 161, Wood, W.A. et al., eds., 1988, Academic Press, pp. 479–484, 498–501.

Yabuki et al., "Purification and Characterization of Chitinase and Chitobiase Produced by *Aeromonas Hydrophila* Subsp. Anaerogenes A52," *J. Gen. Appl. Microbiology*, 32:25–38 (1986).

Harman et al., "Chitinolytic Enzymes of *Trichoderma harzianum*: Purification of Chitobiosidase and Endochitinase," *Phytopathology*, 83(3):313–318 (1993).

DiPietro et al., "Endochitinase from *Gliocladium virens*: Characterization, and Synergistic Antifungal Activity in Combination with Gliotoxin," *Phytopathology*, 83(3):308–313 (1993).

Lorito et al., "Chitinolytic Enzymes Produced by *Trichoderma harzianum*: Antifungal Activity of Purified Endochitinase and Chitobiosidase," *Phytopathology*, 83(3):302–307(1993).

Mauch et al., "Antifungal Hydrolases in Pea Tissue," *Plant Physiol.*, 87:325–333 (1988).

VanHoof et al., "A Single β1,3–Glucanase Secreted by the Maize Pathogen *Cochliobolus carbonum* Acts by an Exolytic Mechanism," *Physiological and Molecular Plant Pathology,* 39:259–267 (1991).

Sullivan et al., "The Secretion of N–Acetylglucosaminidase During Germ–tube Formation in *Candida albicans,"* *J. Gen. Microbiol.,* 130:2213–2218 (1984).

Daugrois, J.H. et al., "Purification and Characterization of Two Basic β–1,3–Glucanases Induced in *Colletotrichum lindemuthianum*–Infected Bean Seedlings," *Arch. Biochem. Biophys.,* 292:468–474 (1992).

Zikakis, J.P. et al., "Chitinase–Chitobiase from Soybean Seeds and Puffballs," in Methods in Enzymology, vol. 161, Wood, W.A. et al., eds., Academic Press, New York, 1988, pp. 490–497.

Manson et al., "Localization of Chitinolytic Enzymes in Blood of Turbot, *Scophthalmus maximus,* and Their Possible Roles in Defens Defense," *J. Fish Biol.,* 40:919–927 (1992).

Gooday, "Physiology of Microbial Degradation of Chitin and Chitosan," *Biodegradation,* 1:177–190 (1990).

Wessels et al., "Wall Structure Wall Growth and Fungal Morphogenesis," eds., Biochemistry of Cell Walls and Membranes in Fungi, Springer–Verlag, London, 1990, pp. 81–95.

El–Sayed et al., "Chitinolytic Activity and Virulence Associated with Native and Mutant Isolates of an Entomopathogenic Fungus, *Nomuraea rileyi,"* *J. of Invertebrate Pathology,* 54:394–403 (1989).

Ohtakara, A., "Chitinase and β–N–acetylhexosaminidase from *Pycnoporous cinnabarinus*" in Methods in Enzymology, vol. 161, Wood, W.A. et al., ed. Academic Press, New York 1988, pp. 462–470.

von Bodman, S. et al., "Synthesis, Bacterial Expression, and Mutagenesis of the Gene Coding For Mammalian Cytochrome $b_5$,"Proc. Natl. Acad. Sci. USA, 83, 9443–9447 (1986).

Carsolio et al., "Characterization of ech–42, a *Trichoderma harzianum* Endochitinase Gene Expressed During Mycoparasitism," *Proc. Natl. Acad. Sci. USA,* 91:10903–10907 (1994).

Kuranda, M.J. et al., "Chitinase Is Required for Cell Separation During Growth of *Saccharomyces cerevisiae,"* *J. Biol. Chem.,* 226(29):19758–19767 (1991).

Giordani, et al., "Antifungal Action of Carica papaya Latex: Isolation of Fungal Cell Wall Hydrolysing Enzymes," *Mycoses,* 34(11–12):469–477 (1991).

Giordani et al., "Glycosidic Activities of *Candida albicans* After Action of Vegetable Latex Saps (Natural Antifungals) and Isoconazole (Synthetic Antifungals),"*Mycoses,* 34(1–2):67–73 (1991).

Davies, D.A.L., Nature, vol. 273, 235–236 (May 18, 1978).

Harman, G.E., et al., Proceedings of EFPP/IOBC Workshop, Copenhagen, Denmark, 7/91, eight pages.

Jones, R.W., et al, Journal of General Microbiology, 134, 2067–2075 (1988).

Klemsdal, S.S., et al., 11th Nordic Postgraduate School in Plant Pathology, abstract of poster presented Feb. 3, 1992 in Tisvildeleije, Denmark.

Lorito, M., et al., Phytopathology, 82, No. 2, 245–246 (2/92).

Poulose, A.J., in Koeller, W., ed., Target Sites of Fungicide Action, CRC Press, Boca Raton, Florida 1992, at pp. 313, 314, 317.

Roberts, D.P., et al, Phytopathology, vol. 80, No. 5, 461–465 (1990).

Richer, D.L., Pestic. Sci. 19:309–315 (1987).

Tronsmo, A., Phytopathology 79(10), 1153 (1989), entry #143.

Tronsmo, A., Norwegian Journal of Agricultural Sciences 3:157–161 (1989).

Tronsmo, A., Biological Control 1, 59–62 (1991).

Vessey, J.C., et al, Trans. Br. Mycol. Soc. 60:710–713 (1973).

The Merck Index, 10th edition, p. 244 (1983).

Jawetz, E., et al, Review of Medical Microbiology, 16th edition, p. 147 (1984).

Berkeley, R. C. W., et al, Microbiol. Polysaccharides and Polysaccharases, 285–311, 436–447 (1979).

Ordentlich, A., et al, Crop Protection, vol. 9, 363–366 (10/90).

Bisaria, V.S., et al, J. Gen. Microbiol. 132(4), 973–978 (1987)—Abstract.

Brewer, D., et al, Can J. Microbiol, vol. 33, 619–625 (1987).

Cabib, E., et al, "Chitin Synthase from *Saccharomyces cerevisiae*" in Methods in Enzymology vol. 138, Ginsburg, V., ed., pp. 643–649, Academic Press, New York, 1987.

Ghisalberti, E.L., et al, Soil Biol. Biochem, vol. 23, No. 11, pp. 1011–1020, 1991.

Griffin, D.H., Fungal Physiology, 2nd edition, pp. 75–85, 173–175, Wiley–Liss, New York, 1993.

Langs, D.A., Science, vol. 241, 188–191 (7/88).

Lorito, M., et al, Microbiology 140, 623–629 (4/94).

Martin, J.–F., Ann. Rev. Microbiol., 31, 13–38 (1977).

Nelson, E.B., et al, Phytopathology, 76 (No. 3), 327–335 (1986).

Neuhaus, J.–M., et al, Plant Molecular Biology 16, 141–151 (1991).

Roberts, W.K., et al, Journal of General Microbiology 134, 169–176 (1988).

Roberts, W.K., et al, Journal of General Microbiology 136, 1771–1778 (1990).

Shinshi, H., et al, Proc. Nat'l. Acad. Sci. USA, vol. 84, pp. 89–93 (1/87).

Schirmbock, M., et al, Applied and Environmental Microbiology, vol. 66, No. 12, 4364–4370 (12/94).

Singh, N.K., et al, Plant Physiol., 85, 529–536 (1987).

Vigers, A.J., et al, Molecular Plant–Microbe Ineractions vol. 4, No. 4, 315–323 (1991).

Vigers, A.J., et al, Plant Science 83, 155–161 (1992).

Mishra, N.C., Proc. Nat'l. Acad. Sci. USA, 69 (2), 313–317 (2/72).

Watanabe, R., et al, Agric. Biol. Chem. 52(4), 895–901 (1988).

Lorito, M., "Expression of Genes from *Trichoderma Harzianum* in Transgenic Plants", from handout at seminar at US Department of Agriculture, 4/95.

Lorito, M., et al, "Antifungal Chitinases and β–1,3–Exoglucanases are Synergistic with Compounds that Alter Membrane Structure or Function" from handout at seminar at US Department of Agriculture, 4/95.

* cited by examiner

COMBINATIONS OF FUNGAL CELL WALL DEGRADING ENZYME AND FUNGAL CELL MEMBRANE AFFECTING COMPOUND

CROSS-REFERENCE TO RELATED APPLICATION

This is a continuation-in-part of application Ser. No. 08/499,164, filed Jul. 7, 1995, now abandoned, which is continuation of application Ser. No. 08/249,927, filed May 26, 1994, now U.S. Pat. No. 5,433,947, which is a continuation of application Ser. No. 07/990,609, filed Dec. 15, 1992, now U.S. Pat. No. 5,326,561. This application claims priority to Provisional Application Ser. No. 60/007567, filed Nov. 27, 1995. This is also a continuation-in-part of U.S. patent application Ser. No. 08/371,680, filed Dec. 21, 1994, issued as U.S. Pat. No. 6,020,540 which is a continuation-in-part of U.S. patent application Ser. No. 08/045,269, filed Apr. 14, 1993, now issued as U.S. Pat. No. 5,378,821, which is a continuation-in-part of U.S. patent application Ser. No. 07/919,784, filed Jul. 27, 1992, issued as U.S. Pat. No. 6,251,390, which is a continuation-in-part of U.S. patent application Ser. No. 07/716,134, filed Jun. 17, 1991, now issued as U.S. Pat. No. 5,173,419.

This invention was made at least in part with Government support under U.S.-Israel Binational Agricultural Research and Development Fund (BARD) grant number US-1723-89. The Government has certain rights in the invention.

TECHNICAL FIELD

This invention is directed at antifungal synergistic combinations of fungal cell wall degrading enzyme and fungal cell membrane affecting fungicide and use thereof for topical or internal application in agriculture or medicine to inhibit germination or growth of fungi.

BACKGROUND OF THE INVENTION

The primary methods of controlling disease-causing fungi on crop plants and on animals, including humans, comprise treatment with synthetic chemical pesticides. However, the exposure of man and habitats to increasing amounts of pesticides has come under criticism, resulting in a search for environmentally safer methods including the use of synergistic combinations of fungicides to reduce the amounts of application.

Poulose, A. J., in Koeller, W., ed., Target Sites of Fungicide Action, CRC Press, Boca Raton, Fla., 1992, at pages 313–314 reviews the disclosures of a number of authors directed to synergistic interaction of different lytic enzymes produced by a variety of microorganisms with a small number of, antifungal compounds including amphotericin B, benomyl, polyoxin B, kitazin P and nikkomycin.

SUMMARY OF THE INVENTION

It is an object of this invention to expand the range of synergistic combinations of fungicide/enzyme.

In one embodiment, the invention is directed to a system for inhibiting the germination or growth of a fungus, said system comprising (a) fungal cell wall degrading chitinolytic or glucanolytic enzyme; (b) antifungal fungal cell membrane affecting compound which-is not expressed by the same organism as the fungal cell wall degrading enzyme in nature, in an amount to provide a concentration where it provides about 4 to 95% inhibition of spore germination when used without (a); the weight ratio of (a) to (b) being 0.005:1 to 500,000:1.

Preferably the fungal cell wall degrading, chitinolytic or glucanolytic enzyme is present in an amount to provide a concentration where said enzyme provides 2 to 50% inhibition of spore germination when it is used without antifungal fungal cell membrane affecting compound and the antifungal fungal cell membrane affecting compound is present in an amount where it provides 10 to 70% inhibition of spore germination when it is used without fungal cell wall degrading chitinolytic or glucanolytic enzyme and the total of the percentage inhibitions provided by the fungal cell wall chitinolytic or glucanolytic enzyme and the antifungal fungal cell membrane affecting compound when each is used without the other is less than 100%.

Very preferably, the fungal cell wall degrading chitinolytic or glucanolytic. enzyme is present in an amount to provide a concentration where said enzyme provides 5 to 20% inhibition of spore germination when it is used without antifungal fungal cell membrane affecting compound and the antifungal fungal cell membrane affecting compound is present in an amount to provide a concentration where said compound provides 15 to 60% inhibition of spore germination when it is used without fungal cell wall degrading enzyme.

The term "system" is used because the fungal wall degrading chitinolytic or glucanolytic enzyme and antifungal fungal cell membrane affecting compound can be applied as part of the same composition or can be applied concurrently as separate compositions or can be applied separately at different times. Preferably, the two kinds of antifungal components of the system are applied in the same composition or concurrently as separate compositions or the antifungal fungal cell membrane affecting compound is applied up to 8 hours after the cell wall degrading chitinolytic or glucanolytic enzyme.

The term "inhibit" is used herein to mean reduce the growth and/or development of fungi compared to where inhibiting agent is not present.

The term "fungal cell wall degrading chitinolytic or glucanolytic enzyme" is used herein to mean chitinolytic or glucanolytic enzyme that effects lysis of fungal cell walls.

The term "antifungal fungal cell membrane affecting compound" is used herein to mean sterol synthesis inhibiting fungicide, antifungal peptide antibiotic, zeamatin and proteins that are serologically related to zeamatin and antifungal lipid lytic enzymes. The term "fungal cell membrane" means plasmalemma and membranes surrounding secretory vesicles, vacuoles, mitochondria, endoplasmic reticulum, and nuclei.

The limitation "which is not expressed by the same organism as the fungal cell wall degrading enzyme in nature" is to exclude combinations which occur in nature.

The concentration where fungal cell wall degrading enzyme individually provides a specified percentage fungal inhibition or where antifungal fungal cell membrane affecting compound individually provides a specific percentage fungal inhibition can be determined as follows: Assays are performed under sterile conditions. Equal volumes of spore suspensions, 3× potato dextrose broth, and the test solution or suspension in 5 mM Tris-HCl (pH 6.0) or 5 mM potassium phosphate buffer (pH 6.7) are mixed. The control is the same as the test solution except for the control the antifungal agent is omitted. The assay mixtures (total volume 45 or 30 $\mu$l) are incubated on flat-bottomed ELISA plates, each containing 96 wells, with 2,000 to 3,000 spores per well, at 25° C. After 22 to 30 hours, the plates are placed under an inverted microscope. The percentage of conidia germinating is determined as the percentage of the first 100 spores randomly found in a well. In addition, the lengths of 20 germ tubes are measured and averaged. All experiments are performed twice, with three replicates for each treatment. The inhibition values obtained in the two experiments are combined and averaged, and standard deviations are calculated from the 6 data points. The values obtained for the control are taken as 0% inhibition and all other values are divided by the values obtained for the control and multiplied by 100% to obtain percent inhibition. Determination of concentration corresponding to a particular percent inhibition is carried out by subjecting dose-response curves to regression analysis by using a binomial regression of the third order, with $R^2$ ranging between 0.95 and 0.99.

The system of the invention can optionally contain as additional components, for example, antifungal polyene macrolide antibiotic, antifungal epithiodiketopiperazine antibiotic, fungal cell wall biosynthesis inhibitor (e.g., chitin synthetase inhibitor or β-1,3-glucan synthetase inhibitor) and/or detergent, in an inhibition improving amount. The term "inhibition improving amount" is used to mean an amount causing a greater % fungal inhibition than if the additional component(s) is/are omitted.

In another embodiment, the invention is directed to a method of inhibiting the germination or growth of a fungus and comprises contacting such fungus or a locus to be protected from such fungus with an antifungal effective amount of combination of fungal cell wall degrading chitinolytic or glucanolytic enzyme in a concentration where said enzyme individually provides 2 to 50% inhibition of spore germination and antifungal fungal cell membrane affecting compound which is not chitinolytic or glucanolytic enzyme and which is not expressed by the same organism as the fungal cell wall degrading enzyme in nature in a concentration where said compound individually provides about 4 to 95%, for example, 10 to 70%, inhibition of spore germination, the total of the percentage inhibitions individually provided by the fungal cell wall degrading chitinolytic or glucanolytic enzyme and the antifungal fungal cell membrane affecting compound being less than 100%.

The term "locus to be protected from such fungus" includes seeds, roots, stems, leaves, flowers and fruits to be protected and to the soil surrounding seeds and roots to be protected, as well as animal or. human tissues or organs to be protected.

In another embodiment, the invention is directed to a method of protecting from a fungus, a plant which expresses fungal cell wall degrading chitinolytic or glucanolytic enzyme at a level of about 0.05 to 5% of total cellular protein, said method comprising contacting said plant with an antifungal effective amount of an antifungal fungal cell membrane affecting compound at a concentration where it individually provides about 4 to 95%, for example, 10 to 70% inhibition of spore germination.

In still another embodiment, the invention is directed to a transgenic plant protected against pathogenic fungi which is a plant susceptible to fungal attack which has been transformed to contain gene which expresses fungal cell wall degrading chitinolytic or glucanolytic enzyme at a level of about 0.05 to 5% of total cellular protein and also which has been transformed to contain gene which expresses protein antifungal cell membrane affecting compound or which has been infected with transgenic endomorphic microorganism producing said protein antifungal fungal cell membrane affecting compound typically in the xylem, in an amount to provide a concentration of said compound where it individually provides about 4 to 95% inhibition of spore germination.

The term "antifungal effective amount" is used herein to mean an amount effective to inhibit the germination or growth of a fungus.

DETAILED DESCRIPTION

Figure 1:
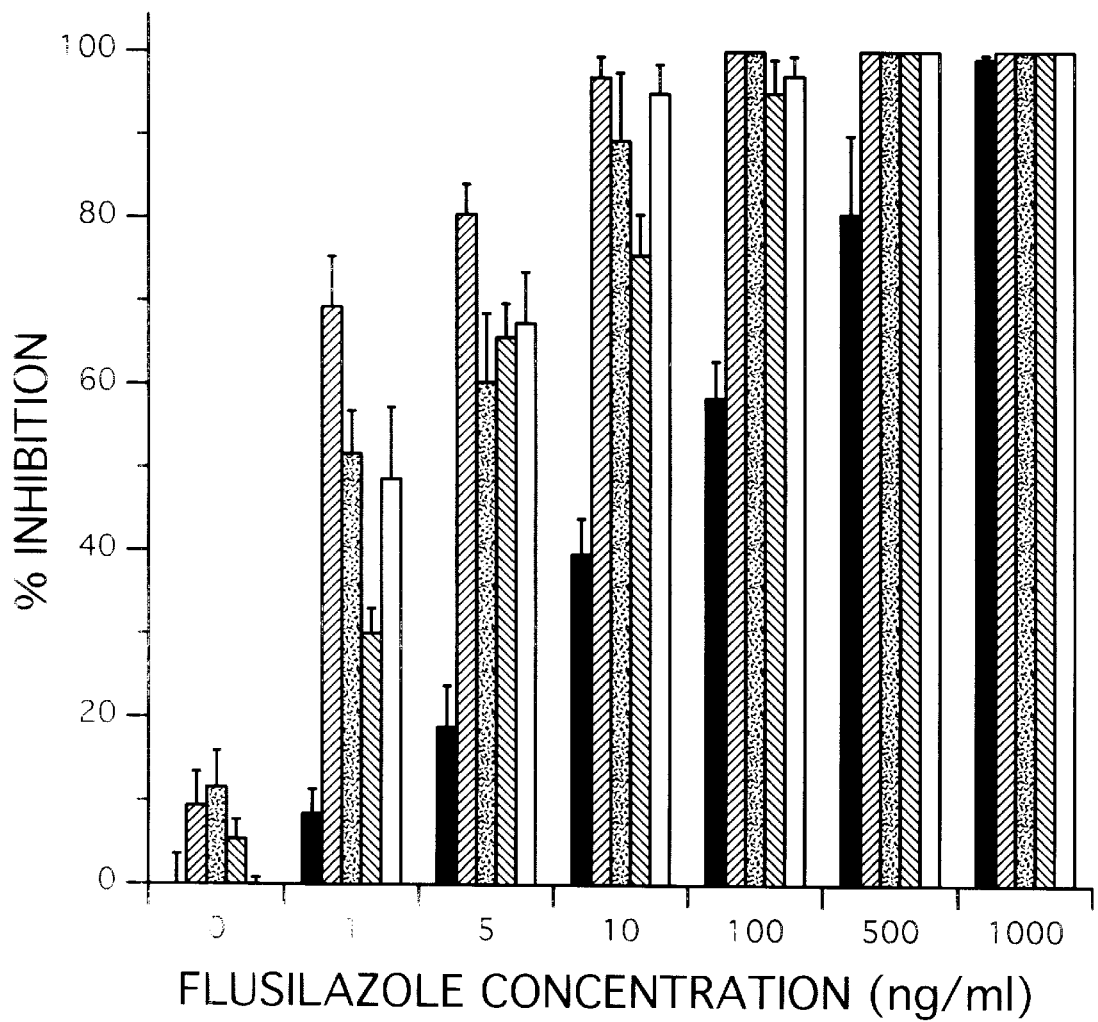
FIG. 1 is a set of bar graphs depicting % inhibition at various flusilazole concentrations, in the presence of different enzymes and in the absence of enzyme, showing results of Example II.

The fungal cell wall degrading chitinolytic and glucanolytic enzymes for use in the embodiments of the invention herein include, for example, chitinolytic enzymes and β-1,3-glucanolytic enzymes for degrading cell walls of fungi where the cell walls contain, as a major structural component, chitin and β-1,3-glucans.

These enzymes are found in fungi; bacteria and higher plants. They can be in natural form, i.e., not separated from the source, e.g., by utilizing source microorganisms in the system herein, or they may be in partially purified form, i.e, purified compared to natural form but with other protein present or they may be in biologically pure form or may be expressed by transgenic plant. Fungal cell wall degrading enzymes are readily obtained in biologically pure form from source fungal microorganisms by culturing the source microorganism, concentrating the culture filtrate, fractionating by gel filtration chromatography, concentrating and further purifying by chromatofocusing followed, if necessary, by isoelectrofocusing in a ROTOFOR® cell (BioRad, Richmond, Calif.). Fungal cell wall degrading enzymes are readily obtained in biologically pure form from bacteria and higher plants by processing comprising culturing, precipitating with $NH_4SO_4$, dissolving and purifying by chromatography and/or isoelectric focusing.

The fungal cell wall degrading chitinolytic enzymes cleave chitin, and include, for example, antifungal endochitinases, chitin 1,4-β-chitobiosidases and β-N-acetylglucosaminidases. These can be obtained from fungi, for example, from the genera Trichoderma, Gliocladium, Lycoperdon and Calvatia; from bacteria, e.g., from the genera Streptomyces, Vibrio, Serratia and Bacillus; and from higher plants, e.g., Nicotiana, Cucumis and Phaesolus.

The endochitinases are enzymes that randomly cleave chitin. Endochitinase activity is readily measured by determining optical density at 510 nm as reduction of turbidity of a 1% suspension of moist purified colloidal chitin in 100 mM sodium acetate buffer, pH 5.5, or in 50 mM $KHPO_4$ buffer, pH 6.7, after 24 hours of incubation at 30° C. For calculation of specific activity, one unit is defined as the amount of enzyme required to obtain a 5% turbidity reduction.

A very preferred endochitinase is coded for by gene of the genome of and is isolated and derived from *Trichoderma harzianum* strain P1 having accession No. ATCC 74058. The protein has a molecular weight of 36 kDa (as determined by sodium dodecyl sulfate polyacrylamide gel electrophoresis after the protein was prepared under reducing conditions, on direct comparison to migration of a 36 kDa protein) and an isoelectric point of 5.3±0.2 as determined based on its elution profile from a chromatofocusing column, and a molecular weight of 40 kDa (as determined by sodium dodecyl sulfate polyacrylamide gel electrophoresis after the protein was prepared under reducing conditions, from a regression based on the log of molecular weight of standard proteins) and an isoelectric point of 3.9 as determined by isoelectric focusing electrophoresis from a regression of distance versus the isoelectric point of standard proteins. The specific activity of the purified endochitinase was determined to be 0.86 units/μg protein with the turbidity reducing assay and 2.2 nkatal/μg protein when nitrophenyl-β-D-N,N',N"-triacetylchitotriose was used as a substrate. This enzyme and its production and purification to homogeneity are described in Harman et al U.S. Pat. No. 5,173,419, and also in Ser. No. 07/919,784, filed Jul. 27, 1992.

Another endochitinase is coded for by gene of the genome of and is isolated and derived from *Gliocladium virens* strain 41 having accession No. ATCC 20906 and has a molecular weight of 41 kDa (as determined by sodium dodecyl sulfate polyacrylamide gel electrophoresis after the protein was prepared under reducing conditions, from a regression based on the log of molecular weight of standard proteins) and an isoelectric point of 7.8 as determined by isoelectric focusing from a regression of distance versus the isoelectric point of standard proteins. The procedures used for molecular weight determination and isoelectric point determination are the same as those-described in detail in Ser. No. 07/919,784. The enzyme is active in citric acid/$K_3(PO_4)$ buffer over a pH range of 3.5 to 7.0 and shows a 90–100% activity between pH 4.0 and 6.0 and shows maximum activity at pH 4.5. The optimum temperature for endochitinase activity at pH 5.5 is between 30 and 37° C., and activity drops off sharply at temperatures above 40° C. This enzyme and its production and purification to homogeneity are described in. DiPietro, A., et al, Phytopathology 83, No. 3, 308–313 (1993). Furthermore, its purification to homogeneity is described in detail in Reference Example 1 hereinafter. The enzyme was purified to an activity 105-fold that of its activity in the culture filtrate.

Two endochitinases are coded for by gene of the genome of and are isolated and derived from *Nicotiana tabacum* cv. Havana 425 and these respectively have molecular weights of 32 kDa and 34 kDa. These endochitinases and their production and purification and obtaining of cDNA clone for endochitinase from *Nicotiana tabacum* cv. Havana 425 and transformation of plant to contain gene from *Nicotiana tabacum* cv. Havana 425 expressing endochitinase activity are described in Shinshi, H., et al, Proc. Natl. Acad. Sci. USA, 84, 89–93 (1/87) and Neuhaus, J. -M., et al, Plant Molecular Biology 16, 141–151 (1991).

The chitin 1,4-β-chitobiosidases cleave dimeric units from chitin from one end. Chitin 1,4-β-chitobiosidases are sometimes referred to for convenience hereinafter as chitobiosidases. Chitobiosidase activity is readily determined by measuring the release of p-nitrophenol from p-nitrophenyl-β-D-N,N'-diacetylchitobiose, e.g., by the following procedure. A substrate solution is formed by dissolving 3 mg of substrate in 10 ml 50 mM $KHPO_4$ buffer, pH 6.7. Fifty μl of substrate solution is added to a well in a microtiter plate (Corning). Thirty μl of test solution is added, and incubation is carried out at 50° C. for 15 minutes. Then the reaction is stopped by the addition of 50 μl of 0.4 M $Na_2CO_3$, and the optical density is read at 410 nm. An activity of one nanokatal (nkatal) corresponds to the release of 1 nmol nitrophenol per second.

A chitobiosidase is coded for by gene of the genome of and is isolated and derived from *Trichoderma harzianum* strain P1 having accession No. ATCC 74058 and in its most prevalent form has a molecular weight of 36 kDa (as determined by sodium dodecyl sulfate polyacrylamide gel electrophoresis after the protein was prepared under reducing conditions, on direct comparison to migration of a 36 kDa protein), and an isoelectric point of 4.4±0.2 as determined based on its elution profile from a chromatofocusing column and a molecular weight of 40 kDa (as determined by sodium dodecyl sulfate polyacrylamide gel electrophoresis after the protein was prepared under reducing conditions, from a regression based on the log of the molecular weight of standard proteins), and an isoelectric point of 3.9 as determined by isoelectric focusing electrophoresis from a regression of distance versus isoelectric point of standard proteins. Conditions for molecular weight determination and isoelectric point determination are described in detail in Ser. No. 07/919,784. It has an optimum pH for activity of about 3 to 7. This chitobiosidase and its production and purification are described in Harman et al U.S. Pat. No. 5,173,419 where it is referred to as a chitobiase, and also in Ser. No. 07/919,784, filed Jul. 27, 1992, where it is referred to as a chitobiase and also as a chitobiosidase. The enzyme obtained in Ser. No. 07/919,784 has a specific activity of 127 nkatal/mg protein and is purified to greater than a 200-fold increase in specific activity compared to its activity in the culture filtrate. Ser. No. 07/919,784 refers to the presence also of a minor band at 36 kDa. It has since been discovered that the chitobiosidase from *Trichoderma harzianum* strain P1 (ATCC 74058) gives three closely spaced protein bands with molecular weights of 40 kDa (staining most intensely), 38 kDa (faintest stain) and 35 kDa (intermediate intensity stain), as determined by sodium dodecyl sulfate polyacrylamide gel electrophoresis after the protein was prepared under reducing conditions, from a regression based on the log of the molecular weight of standard proteins, and that the three bands represent different levels of N-glycosylation of the same protein.

Another chitobiosidase is coded for by gene of the genome of and is isolated and derived from *Gliocladium virens* strain 41 having accession No. ATCC 20906 and has a molecular weight of 38 kDa (as determined by sodium dodecyl sulfate polyacrylamide gel electrophoresis after the protein was prepared under reducing conditions, from a regression based on the log of molecular weight of standard proteins), and an isoelectric point of 4.95 (as determined by isoelectric focusing electrophoresis from a regression of distance versus isoelectric point of standard protein). The proteins used in the determination of molecular mass were 6 standard proteins obtained from Bio-Rad Laboratories, Hercules, Calif., and these proteins and their molecular weights in kDa are respectively hen egg white lysozyme, 14.4; soybean trypsin inhibitor, 21.5; bovine carbonic anhydrase, 31; hen egg white ovalbumin, 45; bovine serum albumin, 66.2; and rabbit muscle phosphorylase b, 97.4. The proteins used in the determination of isoelectric point were 12 standard proteins obtained from Sigma Chemical Company and are respectively amyloglucosidase, 3.6; methyl red dye, 3.8; soybean trypsin inhibitor, 4.6; β-lactoglobulin, 5.1; bovine carbonic anhydrase B, 5.9; human carbonic anhydrase B, 6.6; horse myoglobin cyanocytic band, 6.8; horse myoglobin basic band, 7.2; L-lactic dehydrogenase from rabbit muscle acidic band, 8.3; L-lactic dehydrogenase from rabbit muscle middle band, 8.4; L-lactic dehydrogenase from rabbit muscle basic band, 8.6; and trypsinogen, 9.3. For the linear regressions, $r^2$ values ranged from 0.94 to 0.99. This enzyme and its production and purification to homogeneity are described in Reference Example 2 hereinafter.

Two chitibiosidases are coded for by gene of the genome of and are isolated and derived from. *Streptomyces albid-oflavus* having accession no. NRRL B-16746. These respectively have molecular weights of 27 kDa and 34 kDa and have isoelectric points less than 3.0. The chitobiosidase activity was isolated as follows: The bacteria were grown on slants of trypticase soy agar (BBL, Cockeysville, Md.). Growth was transferred to a liquid medium (50 mM Tris, pH 9.0, 0.012% magnesium sulfate, 0.1% glucose, 0.1% calcium chloride, 0.05% manganese sulfate, 0.025% ferrous. sulfate, 0.00125% zinc sulfate, 0.5% crab shell chitin (Sigma Chemical Co., St. Louis)). The biomass was removed from the broth by centrifugation and filtration. The remaining liquid was brought to 95% saturation with ammonium sulfate, and the precipitate was collected by centrifugation at 6000 ×g for 30 min. at 4° C. The pellet was resuspended in $dH_2O$, dialyzed against ice-cold $dH_2O$ to remove salt and centrifuged at 6000 ×g for 10 min. at 4° C. to remove insoluble particles. The culturing and purification up to this point is described in Broadway, R. M., et al, Lett. Appl. Microbiol. 20, 271–276 (1995). Isolation of chitobiosidase activity was obtained by isoelectric focusing separation as follows: The resulting liquid was applied in approximately equal amounts to compartments of a Rotofor Isoelectric Focusing apparatus (Bio-Rad). The first three fractions contain the chitobiosidase activity.

The β-N-acetylglucosaminidases cleave monomeric units from chitin from one end. β-N-Acetylglucosaminidases may be referred to for convenience hereinafter as glucosaminidases or as nagases. Glucosaminidase activity is readily determined by measuring the release of p-nitrophenol from p-nitrophenyl-β-D-N-acetylglucosaminide, e.g., by the same procedure as described above for assaying for chitobiosidase activity except for the substitution of substrate. An activity of one nanokatal (nkatal) corresponds to the release of 1 nmol nitrophenol per second. Glucosaminidase activity is present in culture filtrates from *Trichoderma harzianum* strain P1 having accession No. ATCC 74058 and from Gliocladium virens strain 41 having accession No. ATCC 20906.

A nagase coded for by gene of the genome of and isolated and derived from *Trichoderma harzianum* strain P1 having accession No. ATCC 74058 has a molecular weight of 72 kDa (as determined by sodium dodecyl sulfate polyacrylamide gel electrophoresis after the protein was prepared under reducing conditions, from a regression. based on the log of molecular weight of standard proteins), and an isoelectric point of 4.6 (as determined by isoelectric focusing electrophoresis from a regression of distance versus isoelectric point of standard proteins). It has good activity over a pH range of 4 to 7 and optimal activity between pH 5.0 and 5.5, as determined in a 50 mM citric acid/potassium phosphate buffer mixture at pH levels ranging from 3.0 to 9.0. It has good activity over a temperature range of 25 to 85° C. with optimal activity at 60 to 70° C., as determined in 50 mM potassium phosphate buffer pH 6.7 at temperatures between 20° C. and 100° C. It is quite resistant to heat inactivation, retaining about 70, 25 and 10% of activity after 15 minutes at 80, 90 and 100° C., respectively. This enzyme and its production and purification are described in Harman et al Ser. No. 08/049,390.

The fungal cell wall degrading glucanolytic enzymes include, for example, antifungal glucan 1,3-β-glucosidases. The glucan 1,3-β-glucosidases cleave 1,3-β-glucans. The sources for these enzymes are typically the same as the sources for chitinolytic enzymes and are preferably microorganisms from the genera Trichoderma and Gliocladium. Glucan 1,3-β-glucosidase activity is readily determined by measuring the amount of reducing sugar release from laminarin in a standard assay containing 250 µl of enzyme solution and 250 µl of a 0.1% solution of laminarin in 50 mM potassium phosphate buffer, pH 6.7, wherein incubation is carried out at 30° C. for 1 hour whereupon 250 µl of a copper reagent (prepared by dissolving 28 g $Na_2PO_4$ and 40 g potassium sodium tatrate in 700 ml deionized water, adding 100 ml of 1N NaOH, then adding 80 ml of a 10% (w/v) solution of $CuSO_4.5H_2O$ with stirring, then adding 180 g $Na_2SO_4$, when all the ingredients have dissolved, bringing to 1 L with deionized water, then allowing to stand for 2 days, then decanting and filtering) is added, and the admixture is covered with foil and heated for 20 minutes in a steam bath, whereupon, after cooling, 250 µl of arsenomolybdate reagent (prepared by dissolving 25 g of $(NH_4)_6Mo_7O_{24}.4H_2O$ in 450 ml deionized water, adding 21 ml concentrated $H_2SO_4$ with mixing, then adding a solution containing 3 g $Na_2HAsO_4.7H_2O$ in 25 ml distilled water and mixing, incubating at 37° C. for 2 days and storing in a brown bottle until used) is added with mixing, followed by adding. of 5 ml deionized water, and reading color in a spectrophotometer at 510 nm, and wherein appropriate controls without either enzyme or substrate may be run simultaneously; the quantity of reducing sugar is calculated from glucose standards included in the assay. An activity of one nkatal corresponds to the release of 1 nmol glucose equivalent per second. Glucan 1,3-β-glucosidase activity is present in culture filtrates from *Trichoderma harzianum* strain P1 having accession No. ATCC 74058 and from *Gliocladium virens* strain 41 having accession No. ATCC 20906.

A glucan 1,3-β-glucosidase is coded for by gene of the genome of and is isolated and derived from *Trichoderma harzianum* strain P1 having accession No. ATCC-74058 and has a molecular weight of 78 kDa (as determined by sodium dodecyl sulfate polyacrylamide gel electrophoresis after the protein was prepared under reducing conditions, from a regression based on the log of molecular weight of standard proteins) and an isoelectric point of 6.2 as determined by isoelectric focusing electrophoresis from a regression of distance versus the isoelectric point of standard proteins. The procedures for molecular weight determination and for isoelectric point determination are the same as those described in Ser. No. 07/919,784. The enzyme has activity against β-1,3 glucan laminarin between pH 4 and 7, with the strongest activity between 4.5 and 5.5. It releases glucose from laminarin at the same rate as reducing groups, which indicates that it is an exoglucanase cleaving monomeric glucose from the laminarin molecule. The enzyme is obtained and purified as generally described above with the medium for culturing of the microorganism being SMCS medium (the same medium used for production of endochitinasen from *G. virens* as described in Reference Example 1 hereinafter). After the chromatofocusing step, several peaks with glucan 1,3-β-glucosidase activity are detected and fractions from major activity peaks are pooled, dialyzed, concentrated and applied to the Rotofor cell to obtain an electrophoretically pure exo-glucanase. The production and purification of the enzyme are described in detail in Reference Example 3 hereinafter. The enzyme was purified to a specific activity. about 35-fold that of its activity in the culture filtrate.

Purified cell wall degrading enzyme has been found to inhibit the germination or growth of a fungus at a concentration in solution, for example, of 50 ppm to 1000 ppm.

As indicated above, the antifungal fungal cell membrane affecting compounds of the embodiments of the invention are selected from. the group consisting of sterollsynthesis inhibiting fungicides, antifungal peptide antibiotics, zeamatin and proteins that are serologically related to zeamatin, and antifungal lipid lytic enzymes.

The sterol synthesis inhibiting fungicides include dimethylation synthesis step inhibitors which are pyridines and pyrimidines and azoles including imidazoles and triazoles. Pyridines and pyrimidines are useful for agricultural purposes and include, for example, triarimol, fenarimol, nuarimol, buthiobate and pyrifenox. Imidazoles useful for agricultural purposes include, for example, imazalil, prochloraz, and triflumidol. Imidazoles useful for medicinal purposes include, for example, miconazole, isoconazole, econazole, clotrimazole, bifonazole, butoconazole, ketoconazole, tioconazole, oxiconazole, fenticonazole, sulconazole and omoconazole. Triazoles useful for agricultural purposes include, for example, triadimefon, triadimenol, bitertanol, diclobutrazole, propiconazole, penconazole, diniconazole, flutriafol, flusilazole, hexaconazole, tebuconazole, myclobutanil, cyproconazole, furconazole and CGA 169374. Triazoles useful for medicinal purposes include, for example, vibunazole, terconazole, itraconazole, fluconazole and ICI 195–739.

The antifungal peptide antibiotics. include, for example, valinomycin, gramicidin and peptaibols including trichorzianines, trichotoxins, alamethicins, paracelsins, trichobrachin, and zervamicins. As indicated in Ghisalberti, E. L, et al, Soil Biol. Biochem., Vol. 23, No. 11, 1011–1020 (1991), the peptaibols are peptides containing aminoisokutyric acid and a C-terminal. aminoalcohol with the term "peptaibol" being a coined word from the underlined portions of the aforestated definition. Valinomycin and gramicidin are available from Sigma Chemical Company. Langs, D. A., Science, Vol. 241, 188–191 (July 1988) describes gramicidin and refers to it as forming ion channels in lipid membranes. Ghisalberti, E. L., et al, Soil Biol. Biochem., Vol. 23, No. 11, 1011–1020 in a review article on antifungal antibiotics produced by Trichoderma spp. describes antifungal peptaibols alamethicin 1, alamethicin 2, paracelsins a–d, trichobrachin, trichotoxin a40, trichotoxin a50, trichorzianine A IIIc, and trichorzianine B IIIc. Ghisalberti et al describes these as interacting with phospholipid membranes and inducing membrane permeability. Brewer, D., et al, Canadian J. Microbiol. 33, 619–625 (1987) describes alamethicins produced by Trichoderma spp. and the isolation of two of them, namely alamethicin 3 and alamethicin 6 and mentions and describes zervamicins produced by Emericellopsis spp. Argondelis, A. D., J. Antibiot. 27, 321–328 (1974) describes zervamicins I and II. Schirmbock, M., et al, Applied and Environmental Microbiology, Vol. 60, No. 12, 4364–4370 (12/94) describes trichorzanines A1 and B1 from *T. harzianum* rifae (ATCC 36042). Schirmboch et al describes these as forming voltage-gated ion channels in black lipid membranes.

We turn now to zeamatin and proteins that are serologically related to zeamatin, that is cross react with antizeamatin antibody under reducing conditions. Zeamatin and its purification are described in Roberts, W. K., et al, Journal of General Microbiology, 136, 1771–1778 (1990). Roberts et al indicates that zeamatin has a molecular mass of 22 kDa and suggests its antifungal properties are the result of forming transmembrane pores in fungal membranes. The proteins that are serologically related to zeamatin include, for example, osmotin, thaumatin, PR-R, PR-S, NP24 and 22 kDa proteins having similar N-terminal amino acid sequence to zeamatin isolated from sorghum, oats and wheat. These are found in plants in response to stress, e.g., salt stress, and cause cell membrane permeabilization. Singh, N. K., et al, Plant Physiol., 15, 529–536 (1987) describes the recovery of osmotin from *Nicotiana tabacum* var Wisconsin 38 and indicates it has a molecular mass of 26 kDa and an isoelectric point-greater than 8.2 and occurs in two forms, an aqueous soluble form (osmotin I) and a detergent soluble form (osmotin II). Thaumatin is described in Edens, L., et al, Gene 18, 1–12 (1982). PR-R and PR-S, i.e., pathogenesis-related protein R and pathogenesis-related protein S, are characterized in Kauffman, S., et al, Plant Mol. Biol 14, 381–390 (1990). PR-R is also described in Cornelissen, B. J. C., et al, Nature (London) 321, 531–532 (1986). NP 24 is described in King, Plant Mol. Biol. 10, 401–411 (1988). Proteins of approximately 22 kDa molecular mass (i.e., similar to zeamatin) and having similar N-terminal amino acid sequence to zeamatin, thaumatin, PR-R and osmotin I and which cross reacted with antizeamatin antiserum are described in Vigers, A. J., et al, Molecular Plant-Microbe Interactions, Vol. 4, No. 4, 315–323 (1991) which suggests the name permatins to describe "this family of membrane-permeabilizing antifungal proteins" and proposes the names sormatin (for the protein isolated from sorghum), avematin (for the protein isolated from oats) and trimatin (for the protein isolated from wheat). Vigers, A. J., et al, Plant Science, 83, 155–161 (1992) describes the serological relation of PR-S and osmotin to zeamatin.

The antifungal lipid lytic enzymes include phospholipases and lipases. Phospholipases include phospholipase A (present in honey bee venom) and phospholipase B (available from Sigma Chemical Company. Lipases include Type I lipase (from wheat germ), Type I-A lipase (insoluble enzyme from wheat germ attached to 4% beaded agarose), Type II lipase (from porcine pancreas), lipase from human pancreas, Type VI-S lipase from porcine pancreas, Type VII lipase (from *Candida cylindracea*), Type VII-A lipase (insoluble enzyme from *Candida cylindracea*), Type XI lipase (from *Rhizopus arrhizus*), Type XII lipase (from *Chromobacterium vicosum*) and Type XII lipase (from Pseudomonas spp.); all these specifically mentioned lipases are available from Sigma Chemical Company.

We turn now to optional adjuvant components of the systems herein.

The optional antifungal polyene macrolide antibiotic adjuvants are described in Martin, J.-F., Am. Rev. Microbiol. 31:13–38 (1977) which describes them as having a lactone ring of 26–38 atoms, a polyene chromophore consisting of a series of 4–7 alternating double bonds that form part of the macrolide ring and usually one aminosugar moiety. Polyene macrolide antibiotics include the following which are listed in Martin: acosin, amphotericin B, aureofungin, aytactin, candicidin, candihexin A, candihexin B, candihexin E, candihexin F, chainin, dermostatin, DJ-400 $B_1$, DJ-400 $B_2$, etuscomycin, eurocidin A, eurocidin B, filipin, flavofungin, fungichromin, hamycin, heptafungin A, levorcin, mycoheptin, nystatin, perimycin, pimaricin, rimocidin, tetrin A, tetrin B and trichomycin. These, when included, are included in the systems herein in a fungus inhibition improving amount. This can be the conventional antifungal amount (dosage).

The antifungal epithiodiketopiperizine antibiotics include, for example, gliotoxin, gliovirin, chaetomin and sporidesmin. Jones, R. W., et al, Journal of General Microbiology, 134, 2067–2075 (1988) states that these are characterized as low-$M_r$, non polar molecules with bridged polysulfide region which confers activity. and suggests that the primary mechanism of action of gliotoxin involves selective binding to cytoplasmic membrane thiol groups. Gliotoxin is available from Sigma Chemical Company. These, when included, are included in a fungus inhibition improving amount. For gliotoxin, this can range, for example, from 1 ng/ml to 5,000 ng/ml.

The optional fungal cell wall biosynthesis inhibitor adjuvants include chitin synthetase inhibitors and β-1,3 glucan synthetase inhibitors.

The chitin synthetase inhibitors include, for. example, polyoxins A, B, D, E, F, G, H, J, K, L, M, N and O; kitazin P and nikkomycin Z. The isolations and characterization of polyoxin A and polyoxin B are described in Isano, K., et al, Biol. Chem. 29, 848 (1965). The isolations and characterizations of polyoxins D, E, F, G, H, J, K and L are described in Isono, K., et al, Agr. Biol. Chem. 30, 817 (1966) and 32, 792 (1968). The isolation and characterization of polyoxin M are described in Isono, K., et al, Tetrahedron Letters, 1970, 425. The isolation of polyoxins N and O are described in Japanese Kokai 72/23,596 (Chemical Abstracts 78:41566t (1973). Polyoxin B is available from Kaken Chemical Co., Ltd. Kitazin P is available from Kumiai Chemical Industry Co., Ltd. Antifungal usage of Polyoxin B and Kitazin P is mentioned in Watanabe, R., et al, Agric. Biol. Chem. 52(4), 895–901 (1988). Nikkomycin Z is available from Calbiochem and is mentioned in Roberts, W. K., et al, Journal of General Microbiology, 136, 1771–1778 (1990). The chitin synthetase inhibitors, when included, are included in the systems herein in a fungus inhibition improving amount which for these agents is a chitin synthesis inhibiting amount. An assay for chitin synthetase activity is-described in Cabib, E., et al, Chitin Synthase from *Saccharomyces cerevesiae*, pages 643–649, in Methods of Enzymology, Vol. 138, Ginsburg, V., editor, Academic Press, New York, 1987. Minimum inhibitory concentrations can be determined by including the inhibitor in the assay mixture of the assay for chitin synthetase activity. Minimum inhibitory concentration of polyoxin B against *B. cinerea* disclosed in Watanabe et al is 12.5 μg/ml. Minimum inhibitory concentrations of kitazin P against *B. cinerea* disclosed in Watanabe et al is 500 μg/ml.

A β-1,3-glucan synthetase inhibitor is L-sorbose. The mechanism of action of L-sorbose is discussed in Mishra, N. C., et al, Proc. Nat. Acad. Sci. USA, Vol. 69, No. 2, pp. 313–317, 2/72. The β-1,3-glucan synthetase inhibitors, when included, are included in the systems herein in a fungus inhibition improving amount. L-Sorbose may be included in compositions for systems herein in an amount ranging from 1 to 10%, for example 1% to 3%.

The optional detergent adjuvant component of the systems herein include, for example, non ionic detergents, e.g., sorbitan esters, polyoxyethylene fatty alkyl ethers, polyoxyethylene nonylphenol ethers, dialkyl sulfosuccinates, ethbxylated and propoxylated mono- or diglycerides, acetylated mono- or diglycerides, lactylated mono- or diglycerides, sugar esters, polysorbates and polyglycerol esters. The sorbitan esters include, for example, polyoxyethylene sorbitan monolaurate (Tween 21), polyoxyalkylene sorbitan monoleate (Tween 20), polyoxyalkylene sorbitan monooleate (Tween 81) and polyoxyalkylene sorbitan monopalmatate (Tween 40). An example of a polyoxyethylene fatty. alkyl ether is polyoxyethylene lauryl ether which is sold under the tradename Emulgen 120. An example of a polyoxyethylene nonylphenol ether is Emulgen 909. An example of a dialkyl sulfosuccinate is dioctyl sulfo succinate (Pelex OTP). The optional adjuvant detergent component can also be an anionic detergent, e.g., sodium lauryl sulfate, or a cationic detergent, e.g., trimethyl palmityl ammonium sulfate. The detergents, when included, are included in the systems herein in a fungus inhibition improving amount and this amount depends on the detergent included and can be as low, for example, as a concentration of 0.001% or as high, for example, as a concentration of 1%. Use of detergents in combination with antifungal agent is described in Watanabe, R., et al, Agric. Biol. Chem. 52 (4), 895–901 (1988) and minimum concentrations at which certain detergents inhibited mycelial growth of P. oryzae are described therein.

As indicated above, the weight ratio of fungal cell wall degrading enzyme to antifungal fungal cell membrane affecting compound is 0.005:1 to 500,000:1, in many cases 2:1 to 500,000:1. Preferred ratios are set forth in Table 1 below wherein "endochit." stands for endochitinase, and "chitobios" stands for chitobiosidase.

TABLE 1

| Combination | Preferred ratio | |
|---|---|---|
| T. harzianum endochit: flusilazole | 5,000:1 to | 85,000:1 |
| T. harzianum endochit: miconazole | 100:1 to | 1,500:1 |
| T. harzianum endochit: osmotin | 1:1 to | 150:1 |
| T. harzianum endochit: gramicidin | 1.5:1 to | 100:1 |
| T. harzianum endochit: valinomycin | 10:1 to | 350:1 |
| T. harzianum endochit: phospholipase B | 1:30 to | 500:1 |
| T. harzianum endochit: Trichorzianine A1 | 100:1 to | 10,100:1 |
| T. harzianum endochit: Trichorzianine B1 | 50:1 to | 12,000:1 |
| G. virens endochit: flusilazole | 10,000:1 to | 475,000:1 |
| G. virens endochit: miconazole | 250:1 to | 4,000:1 |
| G. virens endochit: osmotin | 1:1 to | 100:1 |
| G. virens endochit: gramicidin | 1:7 to | 50:1 |
| G. virens endochit: valinonycin | 5:1 to | 850:1 |
| G. virens endochit: phospholipase B | 1:100 to | 100:1 |
| G. virens endochit: Trichorzianine A1 | 10:1 to | 10,000:1 |
| G. virens endochit: Trichorzianine B1 | 20:1 to | 1,500:1 |
| N. tabacum endochit: flusilazole | 1,000:1 to | 400,000:1 |
| N. tabacum endochit: miconazole | 600:1 to | 4,000:1 |
| N. tabacum endochit: osmotin | 25:1 to | 350:1 |
| N. tabacum endochit: gramicidin | 1:50 to | 500:1 |
| N. tabacum endochit: valinonycin | 50:1 to | 2,000:1 |
| N. tabacum endochit: phospholipase B | 1:1 to | 2,000:1 |
| N. tabacum endochit: Trichorzianine A1 | 300:1 to | 35,000:1 |
| N. tabacum endochit: Trichorzianine B1 | 500:1 to | 40,000:1 |
| T. harzianum chitobios: flusilazole | 2,500:1 to | 350,000:1 |
| T. harzianum chitobios: miconazole | 400:1 to | 3,500:1 |
| T. harzianum chitobios: osmotin | 20:1 to | 200:1 |
| T. harzianum chitobios: gramicidin | 1.5:1 to | 200:1 |
| T. harzianum chitobios: valinonycin | 100:1 to | 2,500:1 |
| T. harzianum chitobios: phospholipase B | 5:1 to | 3,000:1 |
| T. harzianum chitobios: Trichorzianine A1 | 150:1 to | 15,000:1 |
| T. harzianum chitobios: Trichorzianine B1 | 300:1 to | 15,000:1 |
| G. virens chitobios: flusilazole | 1,500:1 to | 300,000:1 |
| G. virens chitobios: miconazole | 250:1 to | 3,000:1 |
| G. virens chitobios: osmotin | 10:1 to | 150:1 |
| G. virens chitobios: gramicidin | 1:1 to | 500:1 |
| G. virens chitobios: valinonycin | 150:1 to | 4,000:1 |
| G. virens chitobios: phospholipase B | 10:1 to | 3,000:1 |
| G. virens chitobios: Trichorzianine A1 | 450:1 to | 20,000:1 |
| G. virens chitobios: Trichorzianine B1 | 350:1 to | 19,000:1 |
| S. albidoflavus chitobios: flusilazole | 12,000:1 to | 250,000:1 |
| S. albidoflavus chitobios: miconazole | 300:1 to | 3,000:1 |
| S. albidoflavus chitobios: osmotin | 1:1 to | 30:1 |
| S. albidoflavus chitobios: gramicidin | 1:1 to | 100:1 |
| S. albidoflavus chitobios: valinonycin | 5:1 to | 1,000:1 |
| S. albidoflavus chitobios: phospholipase B | 1:50 to | 500:1 |
| S. albidoflavus chitobios: Trichorzianine A1 | 80:1 to | 8,000:1 |
| S. albidoflavus chitobios: Trichorzianine B1 | 30:1 to | 10,000:1 |
| T. harzianum nagase: flusilazole | 7,000:1 to | 280,000:1 |
| T. harzianum nagase: miconazole | 100:1 to | 20,000:1 |
| T. harzianum nagase: osmotin | 1:1 to | 250:1 |
| T. harzianum nagase: gramicidin | 1:1 to | 500:1 |
| T. harzianum nagase: valinonycin | 120:1 to | 2,000:1 |
| T. harzianum nagase: phospholipase B | 1:1 to | 1,500:1 |
| T. harzianum nagase: Trichorzianine A1 | 1:150 to | 5,000:1 |
| T. harzianum nagase: Trichorzianine B1 | 250:1 to | 8,000:1 |
| T. harzianum glucosidase: flusilazole | 7,500:1 to | 450,000:1 |
| T. harzianum glucosidase: miconazole | 75:1 to | 45,000:1 |
| T. harzianum glucosidase: osmotin | 5:1 to | 220:1 |
| T. harzianum glucosidase: gramicidin | 1:1 to | 300:1 |
| T. harzianum glucosidase: valinomycin | 7:1 to | 1,500:1 |

TABLE 1-continued

| Combination | Preferred ratio | |
|---|---|---|
| T. harzianum glucosidase: phospholipase B | 10:1 to | 500:1 |
| T. harzianum glucosidase: Trichorzianine A1 | 70:1 to | 9,000:1 |
| T. harzianum glucosidase: Trichorzianine B1 | 100:1 to | 10,000:1 |

Still narrower ranges for T. harzianum endochitinase: flusilazole are 5,000:1 to 85,000:1 and for T. harzianum endochitinase: miconazole are 100:1 to 650:1.

Compositions for use in the systems herein are readily formulated by admixing the fungal cell wall degrading enzymes and the antifungal fungal cell membrane affecting compounds with non-toxic carriers appropriate for the particular use for a composition, e.g., agriculturally acceptable carriers for agricultural uses and pharmaceutically acceptable carriers for medicinal uses. They may be formulated as liquids (solutions or suspensions) or as solids. Since the fungal cell wall degrading enzymes need free water for activity, water must be present at the time of function. This can be accomplished, for example, by applying the fungal cell wall degrading enzymes as aqueous solutions or by formulating the system components as dry powders and applying the powders with the enzyme becoming active once water becomes available, e.g., from rain. Water is a preferred vehicle where components are soluble in it. Osmotin, phospholipase B, trichorzianine A1 and trichorzianine B1 are readily dissolved in water. Organic solvents can also be used and may be required in some cases if a solution is desired. Guidance for forming solutions follows. Gramicidin dissolves in ethanol. Miconazole dissolves in 50% (v:v) ethanol. Flusilazole and valinomycin dissolve in acetone. Gliotoxin dissolves in methanol and ethanol. Suspension can also be employed.

We turn now to formulations for application of the optional adjuvant components. Most polyene macrolide antibiotics have poor water solubility and are therefore normally formulated as dispersions or suspensions for application or applied as a powder. The chitin synthetase inhibitors may also be applied as a powder. Polyoxin B may be dissolved in aqueous ethanol. Kitazin P may be dissolved in a small amount of dimethylformanide and then diluted with water. L-sorbose may be dissolved in water.

We turn now to the method of the invention of inhibiting the germination or growth of a fungus which comprises contacting such fungus or a locus to be protected from such fungus with an antifungal effective amount of a combination of a fungal cell wall degrading chitinolytic or glucanolytic enzyme in a concentration where said enzyme individually provides 2 to 50% inhibition of spore germination and antifungal fungal cell membrane affecting compound which is not chitinolytic or glucanolytic enzyme and which is not expressed by the same organism as the fungal cell wall degrading enzyme in nature in a concentration where said compound individually provides about 4 to 95% inhibition of spore germination, the total of the percentage inhibitions individually provided by the fungal cell wall degrading chitinolytic or glucanolytic enzyme and the antifungal fungal cell membrane affecting compound being less than 100%. The fungal cell wall degrading enzyme and the antifungal fungal cell membrane affecting compound are the same as those discussed in the description of the system of the invention. The effective concentrations are the same as those discussed in the description of the system of the invention. The antifungal effective amount is an amount which inhibits the germination or growth of the fungus that is treated in the method.

For medicinal purposes (i.e., human and veterinary therapy) all the active components can be administered in the same way as the antifungal fungal cell membrane affecting compound is applied when used as the only active ingredient, e.g., topically applied to the skin of a human or non-human animal. Administration can also be, at least in some instances, via parenteral injection, e.g., intraperitoneally; this administration route is particularly useful where the immune system has been compromised since immune-deficient humans and individuals will inactivate enzymatic proteins more slowly than normal individuals.

For agricultural purposes, application can be, for example, to the seed, foliage, roots or fruit of a plant to be protected, or to the soil surrounding said plant, or to the fungus thereon which is to be inhibited. Normally, application is topical. However, other administration strategies can be used.

The system and method described above in the detailed description section contemplate application of the fungal cell wall degrading enzyme and the antifungal fungal cell membrane application as part of the same composition or concurrently as part of separate compositions or separately at different times. When the fungal cell wall degrading enzyme and antifungal fungal cell membrane affecting compounds are applied separately at different times, the inhibition obtained is the same as when the two kinds of agents are applied in the same composition or in different compositions but concurrently, when the antifungal fungal cell membrane affecting compound is applied even as much as 8 hours after the fungal cell wall degrading enzyme. On the other hand, application of the antifungal cell membrane affecting compound before the cell wall degrading enzyme results in reduction in the percentage inhibition obtained compared to when the two kinds of agents are applied as part of the same composition or concurrently in separate compositions until the cell wall degrading enzyme and the antifungal fungal cell membrane affecting compound are both in contact with the fungus for at least about 16 hours. The presence of fungal cell wall degrading enzyme is necessary for about 4 to 8 hours for the highest level of synergistic antifungal effect to be obtained.

The system and method described above in the detailed description section inhibit the germination or growth of fungal species from genera including Fusarium, Gliociadium, Rhizoctonia, Trichoderma, Uncinula, Ustilago, Erysiphe, Botrytis, Saccharomyces, Sclerotium and Alternaria. The specific examples hereinafter show synergism for said system and method herein, in every instance where the antifungal fungal cell membrane affecting compound is used in a concentration less than that where it is substantially entirely effective alone, in application to *Botrytis cinerea*, and in application to *Fusarium oxysporum*, which were selected in the work supporting this invention as model test fungi. Botrytis cinerea is a fungus which is pathogenic to fruits including grapes, raspberries, and apples and to beans and other crops. *Fusarium oxysporum* is a fungus which is pathogenic, for example, to tomatoes, melons, garden peas, cowpeas, beans, soybeans, alfalfa, flax, cotton, carnations, and tobacco.

The synergistic interaction provided by the system and method described above in the detailed description section allows reduction of the quantity of antifungal fungal cell membrane affecting compound that is required for use for a particular inhibition of fungi as much 100- to 1000-fold and this reduction allows usage of fungicides which are otherwise too highly toxic or produce unacceptable side effects at fungicidal or fungistatic dosages, allows usage at dosages less than those which produce side effects and should reduce or at least delay the occurrence of natural resistance to important chemical fungicides.

We turn now to the embodiment herein directed to a method of protecting from a fungus a plant which expresses fungal cell wall degrading chitinolytic or glucanolytic enzyme at a level of 0.05 to 5% of total cellular protein, said method comprising contacting said plant with an antifungal effective amount of an antifungal fungal cell membrane affecting compound at a concentration where it individually provides about 4 to 95% inhibition of spore germination. The plant is a plant which is susceptible to the fungus being protected against which is transformed to contain gene which expresses fungal cell wall degrading chitinolytic or glucanolytic enzyme in the stated amount or which has been infected with transgenic endomorphic microorganisms producing said fungal cell wall degrading chitinolytic or glucanolytic enzyme, typically in the xylem, to produce enzyme internally in the plant in the stated amount. The fungi protected against can be, for example, from the genera of pathogenic fungi described above. Genes coding for fungal cell wall degrading chitinolytic or glucanolytic enzymes can be isolated from microorganisms or other organisms producing them. For example, the characterization and isolation of the gene coding for the aforedescribed endochitinase from *Trichoderma harzianum* strain P1 is described in Harman et al U.S. Pat. No. 5,378,821. Such gene can be inserted into the genome of a plant to be protected, for example, by Agrobacterium-mediated transformation, by biolistic transformation or by other methods known to those skilled in the art. Methods for use for transformation of plants to contain genes are described in Broglie, K., et al., Science 254, 1194–1197 (1991); and in Neuhaus, J.-M., et al., Plant Molec. Biol. 16,141–151 (1991); and in Norelli, J. L., et al., J. Amer. Soc. Hort. Sci. 118,311–316 (1993) taken with Norelli, J. L., et al., Euphytica 77,123–128 (1993); these articles are incorporated herein by reference. The antifungal fungal cell membrane affecting compounds are those described above and the application of antifungal cell membrane affecting compound to the plant can be carried out as described above. Example XX hereinafter is directed to transforming the above described endochitinase encoding gene from *Trichoderma harzianum* strain P1 into tobacco plants using Agrobacterium to obtain the expression of active enzyme in different parts of the plant in an amount of 1–3% of the total cellular protein and application of antifungal fungal cell membrane affecting compound thereto so that it becomes systemic to act synergistically with the expressed endochitinase in providing fungal inhibition.

We turn now to the embodiment herein directed to a transgenic plant protected against pathogenic fungi which is a plant susceptible to fungal attack which has been transformed to contain gene which expresses fungal cell wall degrading chitinolytic or glucanolytic enzyme at a level of about 0.05 to 5% of total cellular protein and also which also has been transformed to contain gene which expresses protein antifungal cell membrane affecting compound or which has been infected with transgenic endomorphic microorganism producing said protein antifungal fungal cell membrane affecting compound typically in the xylem, in an amount to provide a concentration of said compound where it individually provides about 4 to 95% inhibition of spore germination. The fungi protected against can be, for example, from the genera of pathogenic fungi described above. The transformation to contain gene which expresses fungal cell wall degrading chitinolytic or glucanolytic enzyme in the named amounts is described above. Genes coding for protein antifungal fungal cell membrane affecting compound are described in Kumar, V., Plant Molec. Biol. 18,621–622 (1992) and in Watanabe, Y., et al., FEMS Microbiology Letters 124,29–34 (1994). Such genes can be inserted into the genome of a plant, for example, as described. in the paragraph directly above. Exemplary of this embodiment is a crop plant, e.g., a tobacco plant, transformed to contain gene from *Nicotiana tabacum* coding for osmotin and which has been transformed to contain the above described endochitinase encoding gene from *Trichoderma harzianum* strain P1 so the expressed osmotin and expressed endochitinase interact synergistically in providing fungal inhibition.

The following reference examples set forth preparation of some enzymes used in the working examples which illustrate the invention.

REFERENCE EXAMPLE 1

Endochitinase from *Gliocladium virens* strain 41 having accession No. ATCC 20906 as described above was prepared as set forth below.

Synthetic medium was made up containing 680 mg $KH_2PO_4$, 870 mg $K_2HPO_4$, 200 mg KCl, 1 g $NH_4NO_3$, 200 mg $CaCl_2$, 200 mg $MgSO_4.7H_2O$, 2 mg $FeSO_4$, 2 mg $ZnSO_4$, 2 mg $MnSO_4$, 42 g moist purified colloidal chitin (prepared as described in Vessey, J.C., et al, Trans. Br. Mycol. Soc. 60:710–713, 1973), 5 g sucrose, in 1 L distilled water, final pH 6.0.

100 ml of the synthetic medium was placed in a 250 ml Erlenmeyer flask.

The flask was inoculated with conidia grown by inoculation of potato dextrose agar (conidia of *Gliocladium virens* ATCC 20906) to provide $10^7$ conidia $ml^{-1}$ medium and the admixture was incubated at 25° C. for 5 or 7 days on a rotary shaker at 200 rpm. The culture filtrate was harvested by centrifugation at 8000 ×g for 10 minutes and removal of residual particulates by filtration through a glass fiber filter.

The purified endochitinase was isolated from the culture filtrate as described below with all steps being carried out at 4° C. except for concentration which was carried out at room temperature.

The filtered culture filtrate was transferred into dialysis tubing (6,000 to 8,000 Da cutoff) and concentrated 30–40-fold by placing the tubing in solid polyethylene glycol (35,000 MW; Fluka Chemika-Biochemicha, Buchs, Switzerland). The concentrate was dialyzed overnight against 50 mM potassium phosphate buffer pH 6.7 (5 L buffer $L^{-1}$ culture filtrate) and( applied to a gel filtration column (5×60 cm) containing SEPHACRYL® S-300 HR (Pharmacia LKB Biotechnology, Uppsala, Sweden) equilibrated with 50 mM potassium phosphate buffer pH 6.7 containing 200 mM NaCl. The material from 1 L of culture medium was chromatographed separately in two samples on SEPHACRYL® S-300 HR. Fractions, approximately 8 ml each, were eluted with 1500 ml of 50 mM potassium phosphate buffer containing 200 mM NaCl. A first peak between fractions 70 and 120 contained high levels of chitobiosidase and N-acetyl-β-D-glucosaminidase activity. A second peak with endochitinase, β-1,3-glucanase, and chitobiosidase activity was detected in fractions 120 to 140. Fractions 140 to 160 contained endochitinase activity; proteins in this region were apparently not separated on the basis of molecular weight, but adsorbed to the gel matrix since they eluted at or greater than the total column volume. The fractions 140 to 160 from the first sample and similar fractions from the other, showing only endochitinase activity, were pooled. The pooled fractions (160 ml) were transferred into dialysis tubing (6,000 to 8,000 Da cut-off) and concentrated 30- to 40-fold by-placing the tubing in solid polyethylene glycol (35,000 MW; Fluka Chemika-Biochemika, Buchs, Switzerland) and dialyzed overnight against a 20-fold volume of 25 mM ethanolamine-HCl buffer pH 8.7. The sample (about 25 ml) was then applied to a chromatofocusing column (1×30 cm) packed with PBE94 (Pharmacia LKB), and equilibrated with the same buffer used for dialysis. The column was eluted at a flow rate of 50 ml $h^{-1}$ with Polybuffer 96 (Pharmacia LKB) diluted 1:10 and adjusted to pH 7.0 with HCl according to the manufacturer's direction. A sharp peak at pH 8.0 containing endochitinase-activity was detected in the eluted fractions. The peak fractions were pooled and the pooled fractions (about 40 ml) were dialyzed first against a 20-fold volume of 1M NaCl and then against a 40-fold volume of distilled water to remove Polybuffer, and concentrated to a volume of 2 ml in a collodion bag system (10,000 Daj UH 100/1, Schleicher & Schuell. Inc., Keene, N.H.). The sample (2 ml), i.e., the concentrated fractions, was applied to compartments 15 and 16 (pH 8.0–8.5) of a ROTOFOR® isoelectric focusing cell (Bio-Rad, Richmond, Calif.) loaded with 35 ml distilled water containing 2% of Biolyte Ampholytes pH 3–10 (Bio-Rad), run at 12 W constant power, at a temperature of 40° C., after one hour of prefocusing run, and the run was continued for 5 hours. The fractions (each about 2 ml) were collected and assayed for endochitinase activity. The peak fractions contained homogeneous endochitinase as shown by the presence of a single protein band upon SDS-PAGE and upon Native PAGE. A single fluorescent activity band was observed following overlay of the native gel with the methylumbelliferyl substrate.

This activity corresponded to the position of the single protein band detected with coomassie blue and silver stain.

The results of each purification step are summarized in Table 2 below. The endochitinase was purified 105-fold with a recovery of 8%. The quantity of endochitinase produced in the original culture filtrate was calculated to be at least 10 mg $L^{-1}$.

TABLE 2

| Step | Total protein (mg) | Enzyme activity (Units) | Specific activity (U $mg^{-1}$) | Purification (fold) | Yield (%) |
|---|---|---|---|---|---|
| Crude filtrate | 1065.0 | 10,400 | 9.7 | 1.0 | 100 |
| Dialysis | 192.0 | 9,066 | 47.2 | 4.8 | 87 |
| Sephacryl S-300 HR | 7.7 | 2,849 | 371.0 | 38.2 | 27 |
| Chromatofocusing | 3.2 | 1,984 | 620.3 | 63.9 | 19 |
| Rotofor Cell | 0.8 | 815 | 1018.5 | 105.0 | 8 |

The peak (active) fractions were pooled, dialyzed against 1M NaCl and then against distilled water as described above, and concentrated to dryness in a Speedvac apparatus. The enzyme was stored at −20° C. and reconstituted in an appropriate volume of sterilized distilled water for use.

REFERENCE EXAMPLE 2

Chitobiosidase from *Gliocladium virens* strain 41 having accession No. ATCC 20906 as described above was prepared as described below.

Conidia of the Fungus *G. virens* strain 41 (ATCC 20906) were stored on silica gel at −20° C. and used to inoculate potato dextrose agar (PDA: Difco Laboratories, Detroit, Mich.) plates. For enzyme production the fungus was grown in 250 ml Erlenmeyer flasks containing 100 ml of a synthetic medium (SMCS) with colloidal chitin and sucrose as carbon sources. SMCS contained 680 mg $KH_2PO_4$, 870 mg $K_2HPO_4$, 200 mg KCl, 1 g $NH_4NO_3$, 200 mg $CaCl_2$, 200 mg $MgSO_4.7H_2O$, 2 mg $FeSO_4$, 2 mg $ZnSO_4$, 42 g moist purified colloidal chitin, 5 g sucrose, in 1 L distilled water, final pH 6. The flasks were inoculated with conidia collected from freshly grown PDA plates providing $10^7$ conidia $ml^{-1}$ medium, and incubated at 25° C. for 5 days on a rotary shaker at 200 rpm. The culture filtrate was harvested by centrifugation at 8000 xg for 15 minutes and particulate removed by filtration through a glass fiber filter.

The purified chitin 1,4-β-chitobiosidase was isolated from the culture filtrate as described below with all steps being carried out at 4° C. except for concentration which was carried out at room temperature.

The filtered culture filtrate was transferred into dialysis tubing (6,000 to 8,000 Da cut-off) and dialyzed overnight against 50 mM potassium phosphate buffer pH 6.7 containing 200 mM NaCl (8 L buffer $L^{-1}$ culture filtrate), then concentrated approximately 25-fold by placing the tubing in solid polyethylene glycol (20,000 MW; Fisher Scientific). The concentrate was applied, in two sample runs, to a gel filtration column (5×60 cm) containing SEPHACRYL® S-300 (Pharmacia LKB Biotechnology, Uppsala, Sweden) equilibrated with 50 mM potassium phosphate buffer pH 6.7 containing 200 mM NaCl and 0.05% $NaN_3$. Fractions, approximately 10 ml, were eluted with the same buffer using reverse gravitational flow at 140 ml $h^{-1}$. Fractions were assayed for various enzyme activity. Fractions 85–100, which contained high levels of chitobiosidase, endochitinase and glucanase activities, were pooled and concentrated as described above to approximately 25 ml, then dialyzed overnight against a 20-fold volume of 25 mM ethanolamine-HCl buffer pH 8.7. The sample was applied to a chromatofocusing column (1×30 cm) packed with PBE 94 medium (Pharmacia LKB), and equilibrated with the same buffer used for dialysis. Approximately 8 ml fractions were eluted at a flow rate of 50 ml $h^{-1}$ with Polybuffer 96 (Pharmacia LKB), diluted 1:10 and adjusted to pH 7.0 with HCl according to the manufacturer's directions. Fractions 2–8 contained glucanase activity and fractions 12–16 contained endochitinase activity. The chitobiosidase activity was not eluted from the column at. the pH conditions used above. The chitin 1,4-β-chitobiosidase enzyme was removed from the column by eluting with 1 M NaCl. The bulk 1 M chitin 1,4-β-chitobiosidase fraction was dialyzed against a 20-fold volume of distilled water, concentrated to approximately 10 ml as described above and dialyzed against a 40-fold volume of 25 mM imidazole-HCl buffer, pH 6.7. The sample was applied to the same chromatofocusing column used above that had been equilibrated to pH 6.7 with the imidazole-HCl buffer. Fractions were collected by eluting with Polybuffer 74 (Pharmacia), diluted 1:13 and adjusted to pH 3.6 with HCl. Approximately 8 ml fractions were collected with fractions 12–17 containing chitobiosidase activity. These fractions were pooled, concentrated, dialyzed against a 20-fold volume of 1 M NaCl, then against a 100-fold volume of distilled water. At this point the chitin 1,4-β-chitobiosidase was determined to be pure by the presence of only a single band using sodium dodecyl sulfate polyacrylamide gel, native polyacrylamide gel and isoelectric focusing gel electrophoresis. A single fluorescent activity band was observed following overlay of the native gel with the methylumbelliferyl substrate. The sample was concentrated to dryness in a Speedvac apparatus and stored at −20° C.

REFERENCE EXAMPLE 3

A glucan 1,3-β-glucosidase isolated from *Trichoderma harzianum* strain P1 having accession No. ATCC 74058 as described above was prepared as described below.

Crude enzyme solutions were prepared using the growth conditions described for Reference Example 1, except that strain P1 of *T. harzianum* was substituted for *G. virens* ATCC 20906.

All procedures except concentration steps were carried out at 4° C. Enzyme solutions were concentrated at room temperature. The filtered culture filtrate was transferred into dialysis tubing (6,000 to 8,000 Da cut-off) and concentrated 20-fold by placing the tubing in solid polyethylene glycol (35,000 MW; Fluka Chemika-Biochemika, Buchs, Switzerland). The concentrate was dialyzed overnight against 50 mM potassium phosphate buffer pH 6.7 (5 L buffer $L^{-1}$ culture filtrate) and applied to a gel filtration column (5×60 cm) containing SEPHACRYL® S-300 HR (Pharmacia LKB Biotechnology, Uppsala, Sweden) equilibrated with 50 mM potassium phosphate buffer pH 6.7 containing 200 mM NaCl. Fractions (10 ml) were eluted with the same buffer using reverse flow at a rate of 140 ml $h^{-1}$. The material from 1 liter of culture medium was chromatographed separately in two samples on SEPHACRYL® S-300 HR, and fractions (numbers 72 to 84 from the first sample, similar ones from the second) containing glucosidase activity were pooled (approximately 230 ml) and concentrated to about 20 ml as described above. They were then dialyzed overnight against a 20-fold volume of 25 mM Tris-$CH_3COOH$ buffer, pH 8.0. The sample was then applied to a chromatofocusing column (1×30 cm) packed with PBE 94 (Pharmacia LKB), and equilibrated with the same buffer used for dialysis. The column was eluted at a flow rate of 50 ml $h^{-1}$ with Polybuffer 96 (Pharmacia LKB), diluted 1:13 and adjusted to pH 7.0 with $CH_3COOH$ according to the manufacturer's directions. Fractions of interest (fractions 13 to 16; 24 ml total) were pooled, dialyzed first against a 20-fold volume of 1 M NaCl and then against a 40-fold volume distilled water to remove Polybuffer, and concentrated to a volume of 2 ml in a collodion bag system (10,000 Da cutoff; UH 100/1, Schleicher & Schuell Inc., Keene, NH). The enzyme solution was stored at −20° C. until use.

The results of the purification from 1 L culture filtrate are summarized in Table 3 below.

TABLE 3

| Step | Total protein (mg) | Enzyme activity (nkatal) | Specific activity (nkatal $mg^{-1}$) | Purification (fold) | Yield (%) |
| --- | --- | --- | --- | --- | --- |
| Dialyzed culture filtrate | 450 | 1938 | 4.3 | 1.0 | 100 |
| Sephacryl S-300 HR | 144 | 907 | 6.3 | 1.5 | 47 |
| Chromatofocusing | 2.3 | 351 | 153 | 36 | 18 |

The invention is illustrated by the specific examples set forth below.

For the examples, the *B. cinerea* was *B. cinerea* strain 12 isolated from grapes by R. Pearson of Cornell University and the *F. oxysporum* was *F. oxysporum* strain FOP1 isolated from beans in Naples, Italy. For the examples, the osmotin I and endochitinase from *Nicotiana tabacum* were gifts from R. Bressan of Purdue University and the trichorzianines were a gift from B. Bodo of Paris, France.

EXAMPLE I

The antifungal fungal cell membrane affecting compounds tested were flusilazole (E.I. duPont de Nemours) and miconazole (Sigma Chemical Co.).

For the assays herein, the flusilazole was dissolved in acetone and the miconazole was dissolved in 50% ethanol.

The fungal cell wall degrading enzymes tested were endochitinase from Trichoderma harzianum strain P1 (ATCC 74058) prepared as described in Harman et al U.S. Pat. No. 5,173,419 and also in Ser. No. 07/919,784, filed Jul. 27, 1992; the endochitinase from Gliocladium virens strain 41 (ATCC 20906) prepared as described in Reference Example 1; the 40 kDa chitobiosidase from Trichoderma harzianum strain P1 (ATCC 74058) prepared as described in Harman et al in Ser. No. 07/919,784, filed Jul. 27, 1992; and the glucan 1,3-β-glucosidase from Trichoderma harzianum strain P1 (ATCC 74058) prepared as described in Reference Example 3. The fungal cell wall degrading enzymes tested were dissolved in deionized water.

Assay mixtures were prepared that contained 20 µl of a conidial suspension ($10^5$ to $10^6$ conidia/ml) of the test fungus, which was the plant pathogen Botrytis cinerea, 20 µl of a nutrient solution, potato dextrose broth (Difco Laboratories, Detroit, Mich.) made at 3 times the standard rate, 18 µl of a fungal cell wall degrading enzyme solution made to the appropriate concentration (for controls, water was substituted), and 2 µl of the solution or suspension of the antifungal fungal cell membrane affecting compound. As controls, the various solvent solutions were tested at the final concentrations employed, but they had no effect on the test fungus.

Mixtures as indicated above were placed in sterile Eppendorf tubes and incubated 24 to 30 hours at 25° C. Portions of the mixtures were placed on a microscope slide and the germination of the first 100 conidia seen were evaluated. Each treatment was done in triplicate in each experiment, and each experiment was repeated. Percent inhibition was calculated according to the following equation: % I=(1−% $S_t$/% $S_c$)×100, where % I represents the percentage inhibition, % $S_t$ represents percentage germination of spores in the treatment of interest, and % $S_c$ represents the percentage of spores germinating in the control (i.e., with neither antifungal fungal cell membrane affecting compounds, nor enzyme). Appropriate concentrations of the various fungal cell wall degrading enzymes and antifungal fungal cell membrane affecting compounds were evaluated by preliminary experiments which determined, the dosage response curve for each substance singly. Concentrations of fungal cell wall degrading enzyme solutions were employed ranging from 0 to 100 µg/ml, and the concentration of antifungal fungal cell membrane affecting compound was chosen that provided about 20% inhibition of spore germination of B. cinerea. The concentration for each chemical is provided in the tables below.

Results for combinations of antifungal fungal cell membrane affecting compound and endochitinase from Trichoderma harzianum strain P1 are set forth in Table 4 below.

TABLE 4

| Fungicides | % inhibition of different concentrations of enzyme (µg ml$^{-1}$) | | | | |
|---|---|---|---|---|---|
| | 0 | 25 | 50 | 75 | 100 |
| Flusilazole (5 ng ml$^{-1}$) | 18 | 99 | 100 | 100 | 100 |
| Miconazole (0.5 µg ml$^{-1}$) | 19 | 100 | 100 | 100 | 100 |
| None | 0 | 29 | 61 | 65 | 73 |

Results for combinations of antifungal fungal cell membrane affecting compound and endochitinase from Gliocladium virens strain 41 (ATCC 20906) are set forth in Table 5 below.

TABLE 5

| Fungicides | % inhibition at different concentrations of enzyme (µg ml$^{-1}$) | | | | |
|---|---|---|---|---|---|
| | 0 | 25 | 50 | 75 | 100 |
| Flusilazole (5 ng ml$^{-1}$) | 18 | 89 | 100 | 100 | 100 |
| Miconazole (0.5 µg ml$^{-1}$) | 19 | 99 | 100 | 100 | 100 |
| None | 0 | 0 | 0 | 24 | 35 |

Results for combinations of antifungal fungal cell membrane affecting compound and chitobiosidase from Trichoderma harzianum strain P1 (ATCC 74058) are set forth in Table 6 below.

TABLE 6

| Fungicides | % inhibition at different concentrations of enzyme (µg ml$^{-1}$) | | | | |
|---|---|---|---|---|---|
| | 0 | 25 | 50 | 75 | 100 |
| Flusilazole (5 ng ml$^{-1}$) | 18 | 60 | 100 | 100 | 100 |
| Miconazole (0.5 µg ml$^{-1}$) | 19 | 85 | 100 | 100 | 100 |
| None | 0 | 11 | 20 | 24 | 28 |

Results for combinations of antifungal fungal cell membrane affecting compound glucan 1,3-β-glucosidase from Trichoderma harzianum strain P1 (ATCC 74058) are set forth in Table 7 below.

TABLE 7

| Fungicides | %. inhibition at different concentrations of enzyme (µg ml$^{-1}$) | | | | |
|---|---|---|---|---|---|
| | 0 | 25 | 50 | 75 | 100 |
| Flusilazole (5 ng ml$^{-1}$) | 18 | 49 | 63 | 89 | 100 |
| Miconazole (0.5 µg ml$^{-1}$) | 19 | 50 | 70 | 88 | 100 |
| None | 0 | 17 | 32 | 40 | 50 |

Every combination provided a synergistic interaction. The most appropriate equation to test for synergy was described by Richer (Richer, D. L. Pestic. Sci. 19, 3.09–315, 1987) as Limpel's formula $E_e=X+Y-XY/100$, where $E_e$ is the expected effect from additive responses of the chemicals and X and Y are percentage inhibition of the chemicals. Thus, if X provides 20% inhibition and Y provides 30%, the expected additive effect is 20+30−(20×30)/100=44%. Any value greater than 44% is evidence of synergy. This equation is based on the consideration that if X kills 20% of the organisms available, then only 80% of the total are available to Y.

The tables above provide values for each antifungal fungal cell membrane affecting compound/fungal cell wall degrading enzyme combination, with the antifungal fungal cell membrane affecting compound used at the $ED_{20}$ level (dose effective to cause 20% inhibition when antifungal fungal cell membrane affecting compound is used alone) and fungal cell wall degrading enzyme concentrations ranging from 0 to 100 µg/ml. The levels of synergy shown are substantial; for example, miconazole alone at 0.5 µg/ml gave 19% inhibition and the endochitinase from G. virens alone at 25 µg/ml gave 0% inhibition, while the combination gave 99% inhibition.

EXAMPLE II

The assay procedure, fungal cell wall degrading enzymes, and antifungal fungal cell membrane affecting compounds were the same as those used in Example I. As in Example I, the test fungus was *B. cinerea*.

Figure 2:
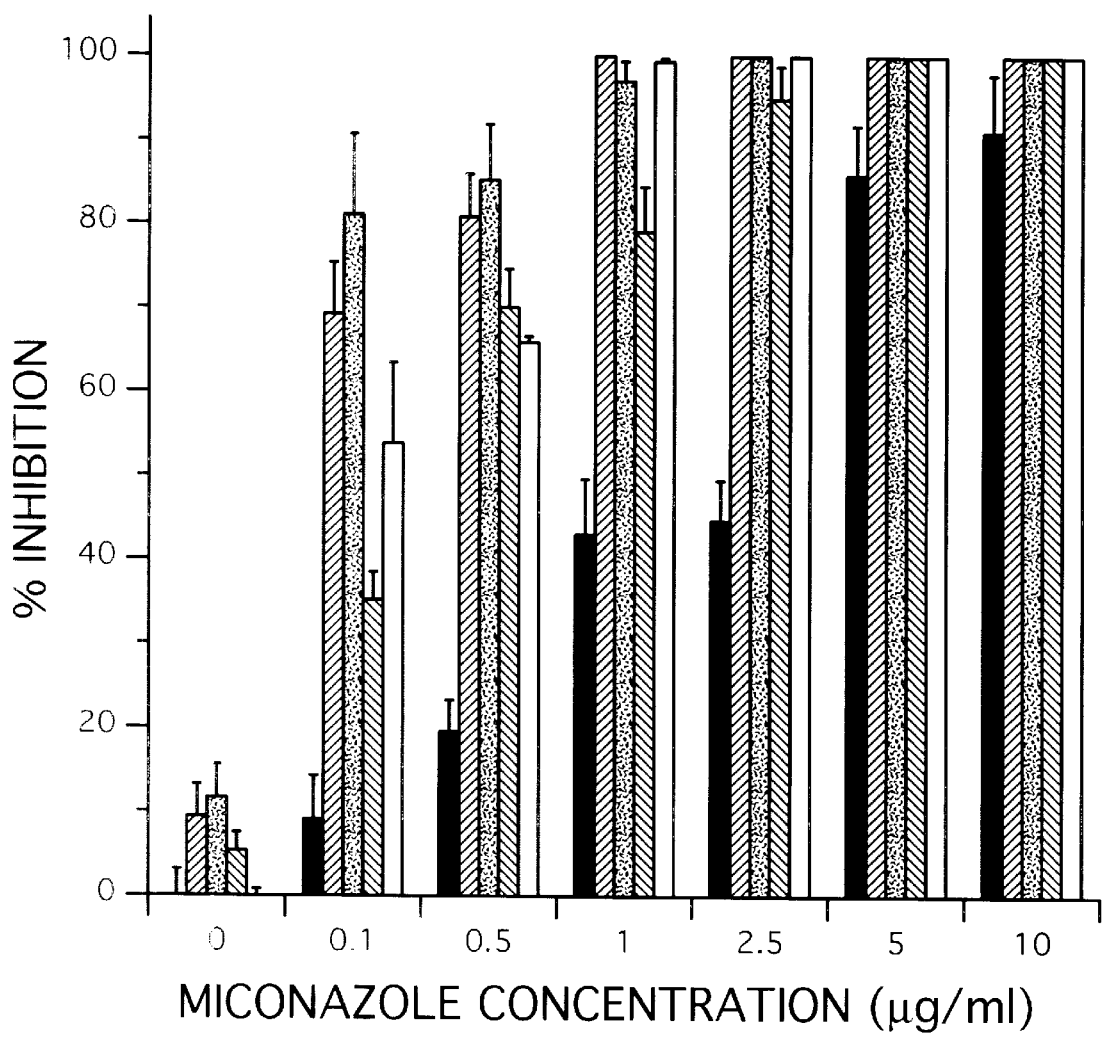
FIG. 2 is a set of bar graphs depicting % inhibition at various miconazole concentrations, in the presence of different enzymes and in the absence of enzyme, showing results of Example II.

Results are presented in FIGS. 1 and 2 which are bar graphs showing % inhibition at antifungal fungal cell membrane affecting compound concentrations as recited, in the presence of fungal cell wall degrading enzyme and in the absence of fungal cell wall degrading enzyme, wherein the totally black bars denote no fungal cell wall degrading enzyme, the hatched bars with alternating black and dotted lines denote endochitinase from *Trichoderma harzianum* strain P1 (ATCC 74058) at 10 μg/ml, the bars filled in with dots denote 40 kDa chitobiosidase from *Trichoderma harzianum* strain P1 (ATCC 74058) at 25 μg/ml, the bars hatched with alternating open areas and lines denote glucan 1,3-β-glucosidase from *Trichoderma harzianum* strain P1 (ATCC 74058) at. 25 μg/ml and the bars that are open denote endochitinase from *Gliocladium virens* strain 41 (ATCC 20906) at 25 μg/ml . In the graphs, error bars indicate standard deviations. The values for inhibition are means across two experiments with three replicates for each experiment.

Results are also set forth in Table 8 below wherein $E_e$ is the expected effect from an additive response according to Limpel's formula expressed as percent inhibition and $I_o$ is the percent inhibition observed and "Endoc.(P1)" stands for endochitinase from *Trichoderma harzianum* strain P1 (ATCC 74058), "Chitob. (P1)" stands for chitobiosidase from *Trichoderma harzianum* strain P1 (ATCC 74058), "Glucan.(P1)" stands for glucan 1,3-β-glucosidase from *Trichoderma harzianuim* strain P1 (ATCC 74058) and "Endoc.(41)" stands for endochitinase. from *Gliocladium virens* strain 41 (ATCC 20906), and each of the fungal cell wall degrading enzymes was used at a concentration of 25 μg/ml.

TABLE 8

| Toxins (concentration) | Endoc. (P1) 25 μg ml$^{-1}$ | | Chitob. (P1) 25 μg ml$^{-1}$ | | Glucan. (P1) 25 μg ml$^{-1}$ | | Endoc. (41) 25 pg ml$^{-1}$ | |
|---|---|---|---|---|---|---|---|---|
|  | $E_e$ | $I_o$ | $E_e$ | $I_o$ | $E_e$ | $I_o$ | $E_e$ | $I_o$ |
| Flusilazole (5 ng ml$^{-1}$) | 41 | 99 | 27 | 60 | 22.1 | 65 | 18 | 67 |
| Miconazole (0.5 μg ml$^{-1}$) | 42.5 | 100 | 27.9 | 85 | 23 | 70 | 19 | 66 |

Table 9 below shows $ED_{50}$ values for endochitinase from *Trichoderma harzianum* strain P1 (ATCC 74058) and for the antifungal fungal cell membrane affecting compounds tested with no endochitinase and with endochitinase at concentrations indicated. $ED_{50}$ is the dose effective for 50% inhibition.

TABLE 9

| | Endochitinase ($ED_{50}$ of 41 μg ml$^{-1}$) (μg ml$^{-1}$) | | |
|---|---|---|---|
| Fungicides | 0 | 10 | 25 |
| Flusilazole | 0.06 | 0.0007 | 0.0003 |
| Miconazole | 3.0 | 0.06 | 0.04 |

Table 10 below shows $ED_{50}$ values for chitobiosidase from *Trichoderma harzianum* strain P1 (ATCC 74058) and for the antifungal fungal cell membrane affecting compounds tested with no chitobiosidase and with chitobiosidase at concentrations indicated.

TABLE 10

| | Chitobiosidase ($ED_{50}$ of 152 μg ml$^{-1}$) (μg ml$^{-1}$) | | | | |
|---|---|---|---|---|---|
| Fungicides | 0 | 25 | 50 | 75 | 100 |
| Flusilazole | 0.06 | 0.001 | 0.0004 | 0.00035 | 0.0003 |
| Miconazole | 3.0 | 0.06 | 0.045 | 0.04 | 0.03 |

Table 11 below shows $ED_{50}$ values for glucan 1,3-β-glucosidase from *Trichoderma harzianum* strain P1 (ATCC 74058) and for the antifungal fungal cell-membrane affecting compounds tested with no glucosidase and with glucosidase at concentrations indicated.

TABLE 11

| | Glucosidase ($ED_{50}$ of 90 μg ml$^{-1}$) (μg ml$^{-1}$) | | | |
|---|---|---|---|---|
| Fungicides | 0 | 25 | 50 | 75 |
| Flusilazole | 0.06 | 0.0033 | 0.001 | 0.00017 |
| Miconazole | 3.0 | 0.27 | 0.04 | 0.0018 |

Table 12 below shows $ED_{50}$ values for endochitinase from *Gliocladium virens* strain 41 (ATCC 20906) and for the antifungal fungal cell membrane affecting compounds tested with no endochitinase and with endochitinase at concentrations indicated.

TABLE 12

| | Endochitinase ($ED_{50}$ of 195 μg ml$^{-1}$) (μg ml$^{-1}$) | | | | |
|---|---|---|---|---|---|
| Fungicides | 0 | 25 | 50 | 75 | 100 |
| Flusilazole | 0.06 | 0.0025 | 0.001 | 0.0045 | 0.00022 |
| Miconazole | 3.0 | 0.092 | 0.06 | 0.04 | 0.025 |

In data not depicted in figures or shown in tables, the addition of 1 ng ml$^{-1}$ of flusilazole reduced the $ED_{50}$ value 6.8-fold for endochitinase from *Trichoderma harzianum* strain P1 (ATCC 74058) and 4.6-, 1.3- and 3.9-fold for chitobiosidase and glucanase from *Trichoderma harzianum* strain P1 (ATCC 74058) and endochitinase from *Gliocladium virens* strain 41 (ATCC 20906), respectively.

The addition of the cell wall degrading enzymes to the prxeparations of antifungal fungal cell membrane affecting compounds at the concentrations tested increased the occurrence of morphological changes such as lysis of the mycelium and hyphal tips in the germinating spores of *B. cinerea*.

EXAMPLE III

This experiment tested the effect of endochitinase from *Gliocladium virens* strain 41 (endoc G) on the inhibition of spore germination of *Botrytis cinerea* strain 12 by osmotin I.

Assays were carried out by the procedure described in the summary of the invention section. Dose response curves were obtained by probit analysis of data collected from two separate experiments with each experiment involving three treatment replicates.

Figure 3:
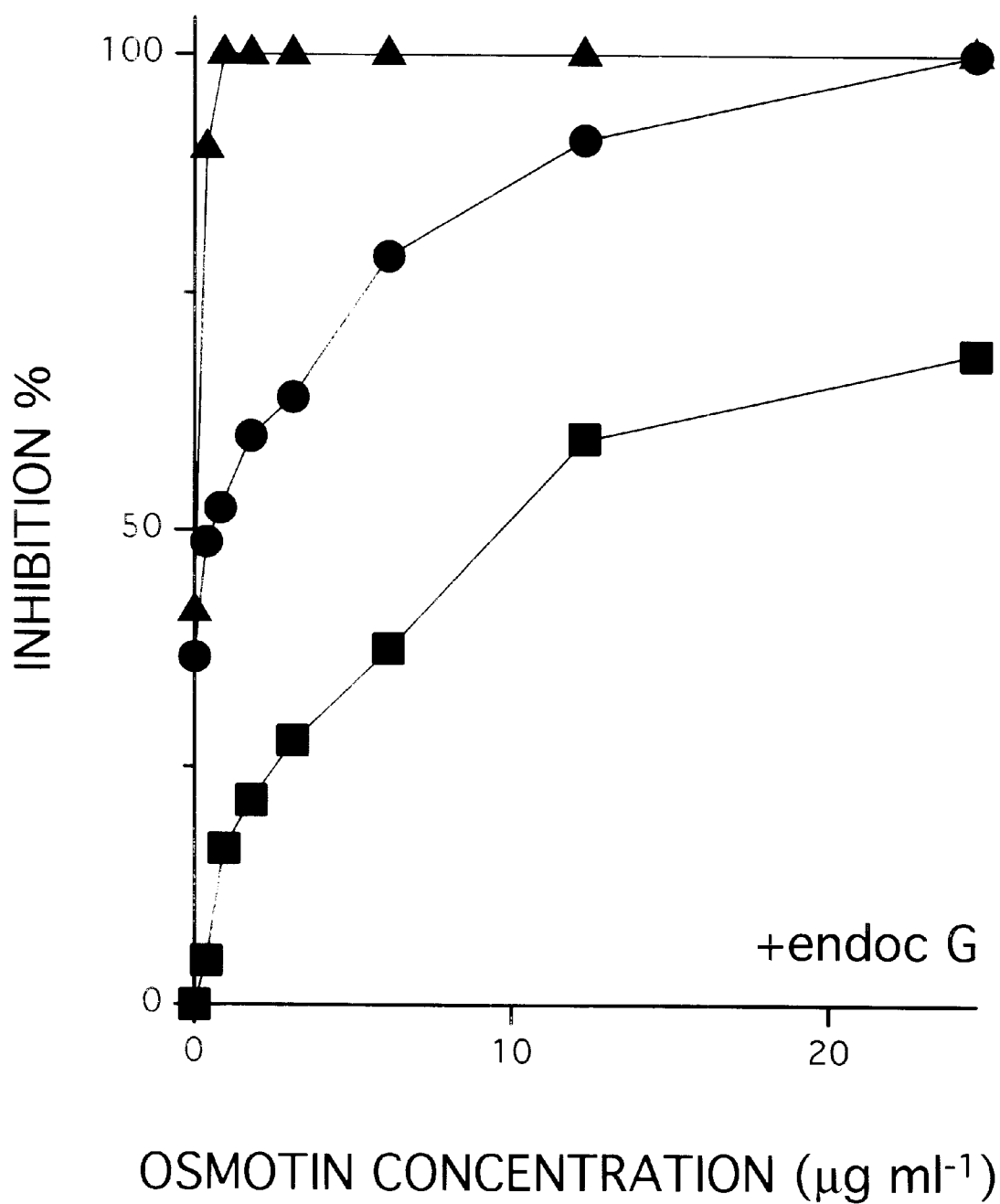
FIG. 3 is a set of graphs of osmotin concentration versus percent inhibition of spore germination of B. cinerea with concentration of endochitinase from G. virens strain 41 varied and shows results of Example III.

FIG. 3 shows the results. In FIG. 3, the filled in squares represent data points where endoc G was present in the assay mixture at a concentration of 0 µg/ml, the filled in circles represent data points where endoc G was present in the assay mixture at a concentration of 5 µg/ml and the filled in triangles represent data points where endoc G was present in the assay mixture at a concentration of 10 µg/ml.

As indicated in FIG. 3, the combination of fungal cell wall degrading enzyme and antifungal fungal cell membrane affecting compound inhibit spore germination of *B. cinerea* more strongly than each agent alone.

EXAMPLE IV

This experiment tested the effect of glucosidase from *Trichoderma harzianum* strain P1 (glucos T) on the inhibition of spore germination of *Botrytis cinerea* strain 12 by osmotin I.

Assays were carried out by the procedure described in the summary of the invention section. Dose response curves were obtained by probit analysis of data collected from two separate experiments with each experiment involving three treatment replicates.

Figure 4:
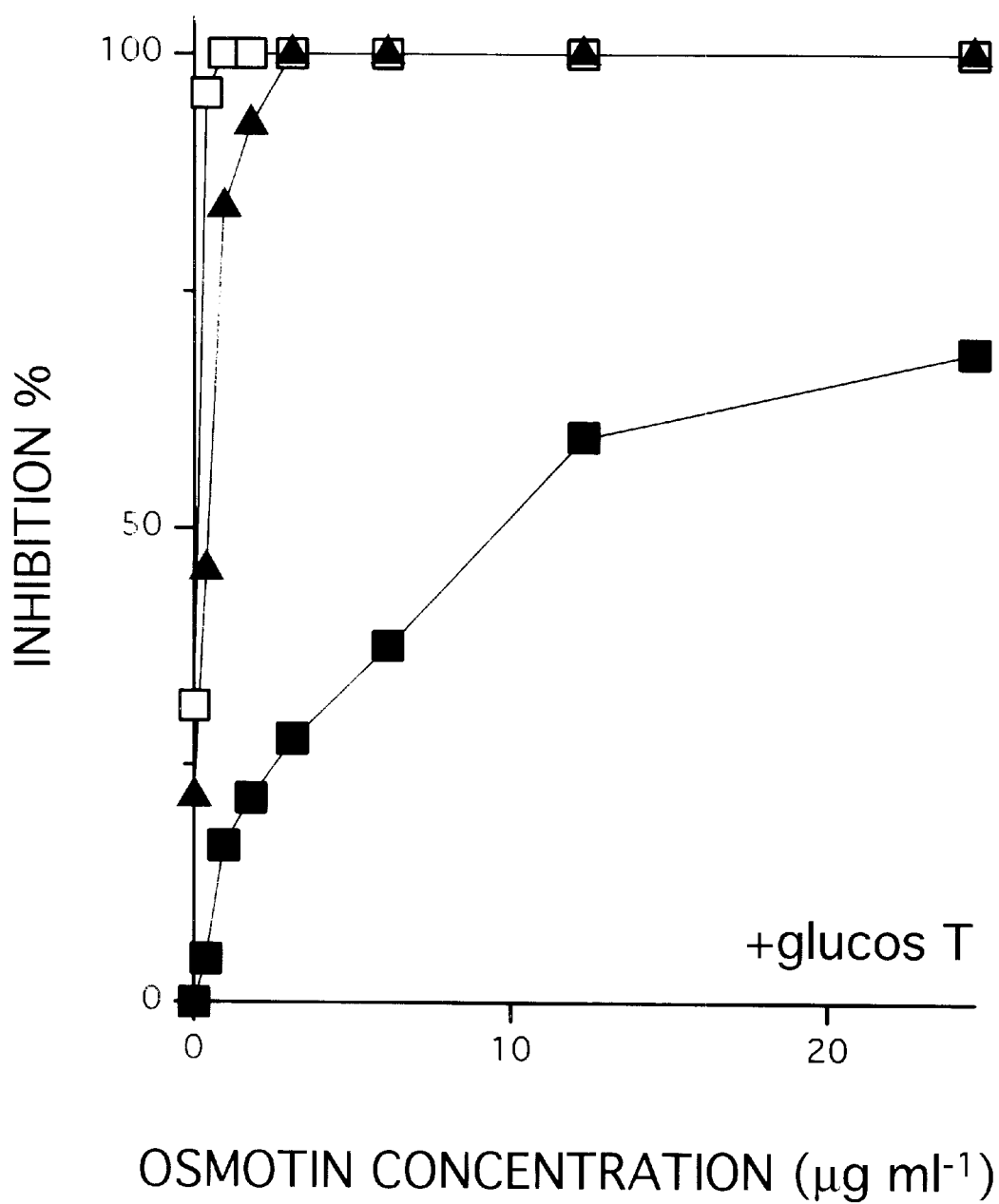
FIG. 4 is a set of graphs of osmotin concentration versus percent inhibition of spore germination of B. cinerea with concentration of glucosidase from T. harzianum strain P1 varied and shows results of Example IV.

FIG. 4 shows the results. In FIG. 4, the filled in squares represent data points where glucos T was present in the assay mixture at a concentration of 0 µg/ml, the filled in triangles represent data points where glucos T was present in the assay mixture at a concentration of 10 µg/ml and the open squares represent data points where glucos T was present in the assay mixture at a concentration of 25 µg/ml.

As indicated in FIG. 4, the combination of fungal cell wall degrading enzyme and antifungal fungal cell membrane affecting compound inhibit spore germination of *B. cinerea* more strongly than each agent alone.

EXAMPLE V

This experiment tested the effect of endochitinase from *Trichoderma harzianum* strain P1 (endoc T) on the inhibition of spore germination of *Fusarium oxysporum* strain FOP1 by osmotin I.

Assays were carried out by the procedure described in the summary of the invention section. Dose response curves were obtained by probit analysis of data collected from two separate experiments with each experiment involving three treatment replicates.

Figure 5:
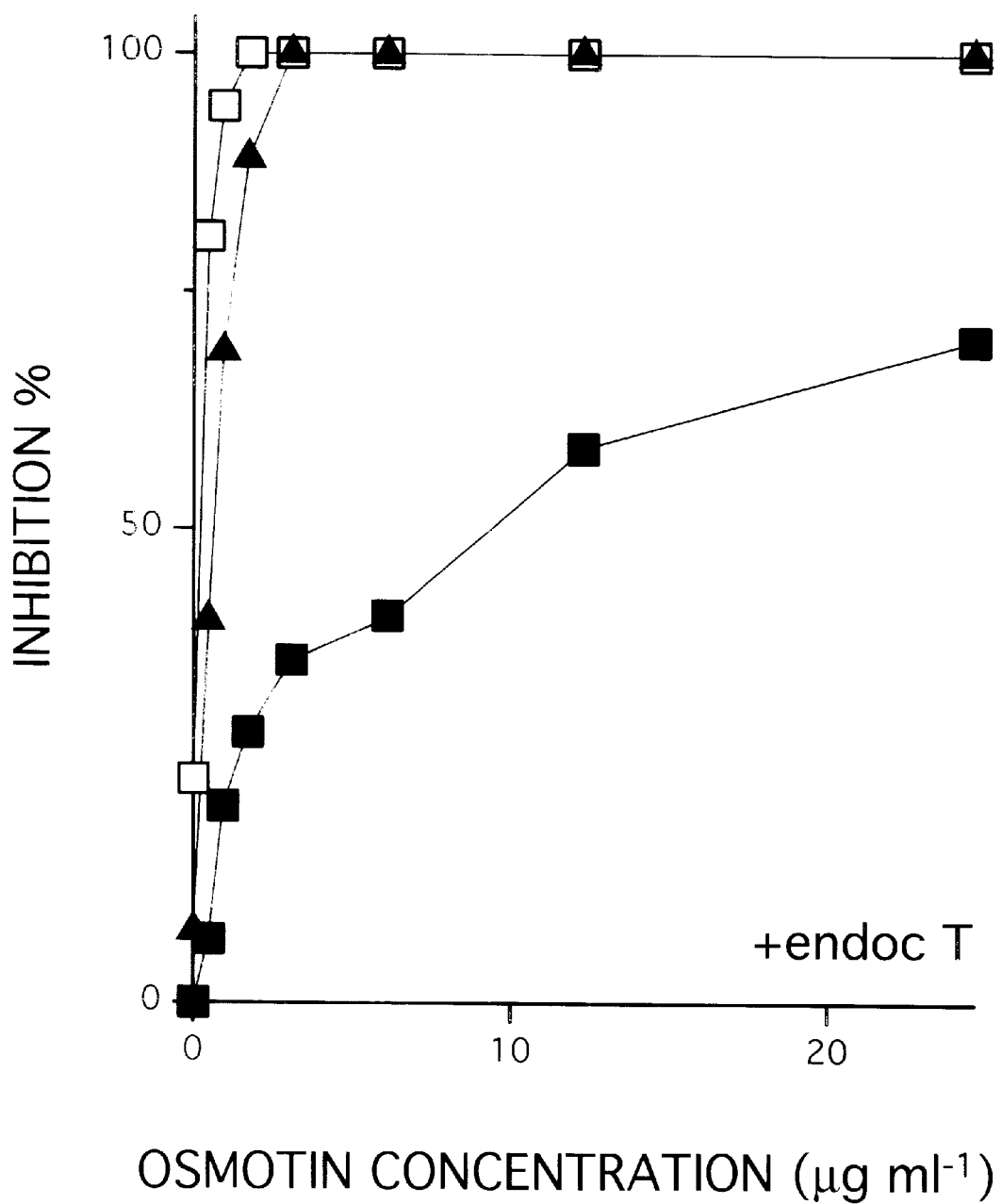
FIG. 5 is a set of graphs of osmotin concentration versus percent inhibition of spore germination of F. oxysporum with concentration of endochitinase from T. harzianum strain P1 varied and shows results of Example V.

FIG. 5 shows the results. In FIG. 5, the filled in squares represent data points where endoc T was present in the assay mixture at a concentration of 0 µg/ml, the filled in triangles represent data points where endoc T was present in the assay mixture at a concentration of 10 µg/ml and the open squares represent data points where endoc T was present in the assay mixture at a concentration of 25 µg/ml.

As indicated in FIG. 5, the combination of fungal cell wall degrading enzyme and antifungal fungal cell membrane affecting compound inhibit spore germination of *F. oxysporum* more strongly than each agent alone.

EXAMPLE VI

This experiment tested the effect of glucosidase from *Trichoderma harzianum* strain P1 (glucos T) on the inhibition of spore germination of *Fusarium oxysporum* strain FOP1 by osmotin I.

Assays were carried out by the procedure described in the summary of the invention section. Dose response curves were obtained by probit analysis of data collected from two separate experiments with each experiment involving three treatment replicates.

Figure 6:
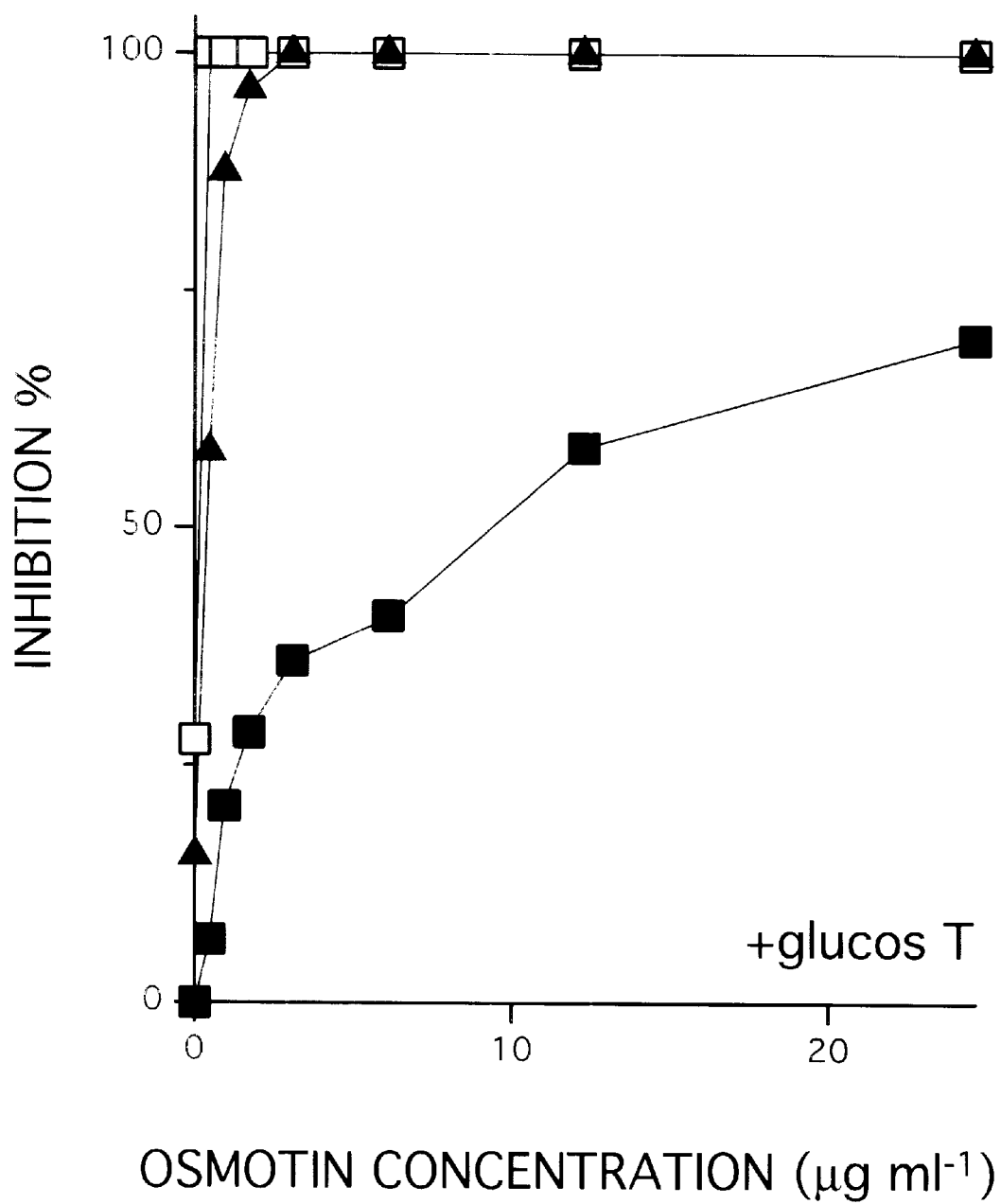
FIG. 6 is a set of graphs of osmotin concentration versus percent inhibition of spore germination of F. oxysporum with concentration of glucosidase from T. harzianum strain P1 varied and shows results of Example VI.

FIG. 6 shows the results. In FIG. 6, the filled in squares represent. data points where glucos T was present in the assay mixture at a concentration of 0 µg/ml, the filled in triangles represent data points where glucos T was present in the assay mixture at a concentration of µg/ml and the open squares represent data points where glucos T was present in the assay mixture at a concentration of 25 µg/ml.

As indicated in FIG. 6, the combination of fungal cell wall degrading enzyme and antifungal fungal cell membrane affecting compound inhibit spore germination of *F. oxysporum* more strongly than each agent alone.

EXAMPLE VII

This experiment tested the effect of endochitinase from *G. virens* strain 41 (endoc G) on the inhibition of spore germination of *B. cinerea* strain 12 by gramicidin.

Assays were carried out by the procedure described in the summary of the invention section. Dose response curves were obtained by probit analysis of data collected from two separate experiments with each experiment involving three treatment replicates.

Figure 7:
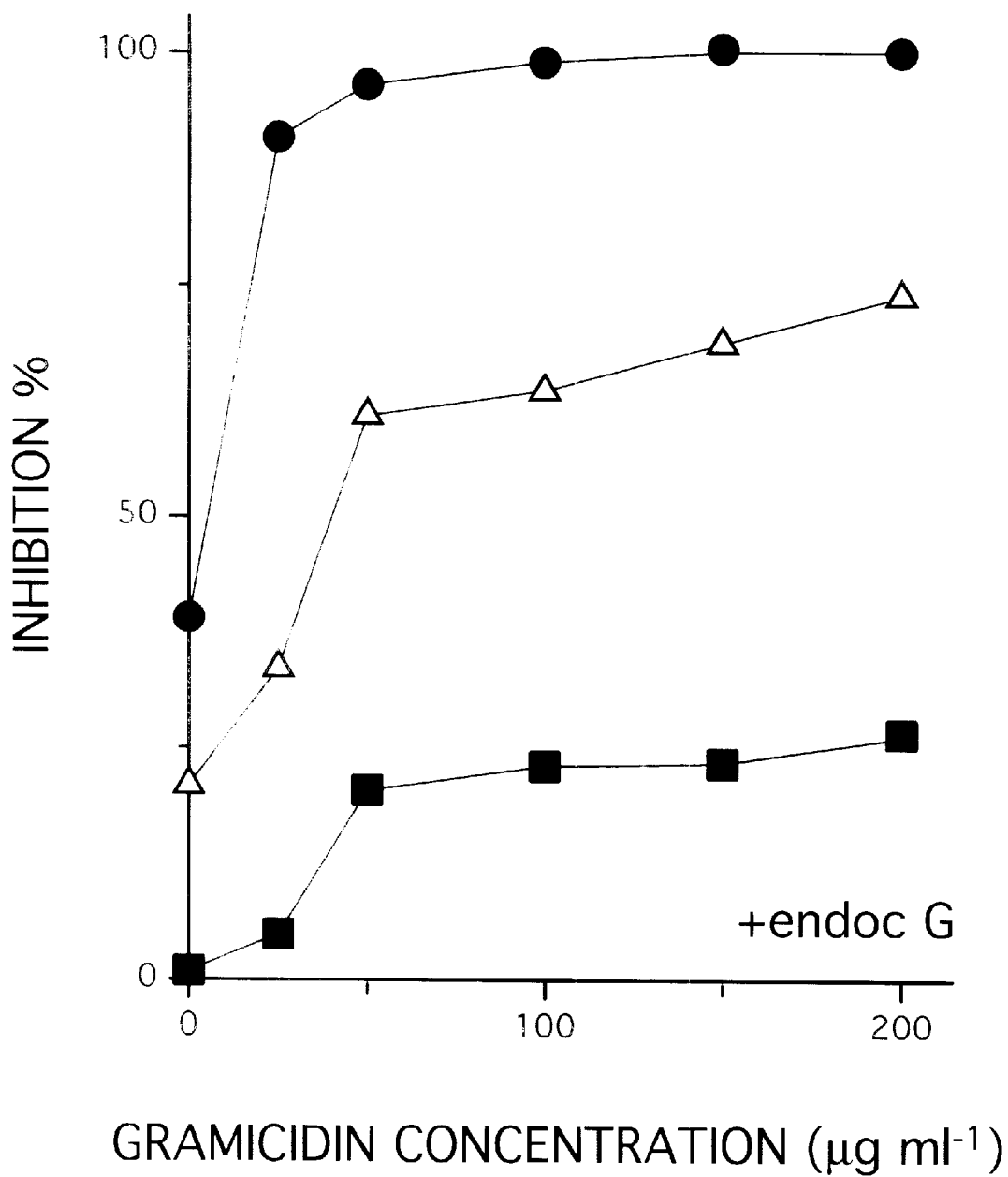
FIG. 7 is a set of graphs of gramicidin concentration versus percent inhibition of spore germination of B. cinerea with concentration of endochitinase from G. virens strain 41 varied and shows results of Example VII.

FIG. 7 shows the results. In FIG. 7, the filled in squares represent data points where endoc G was present in the assay mixture at a concentration of 0 µg/ml, the open triangles represent data points where endoc G was present in the assay mixture at a concentration of 2.5 µg/ml and the filled in circles represent data points where endoc G was present in the assay mixture at a concentration of 5 µg/ml.

As indicated in FIG. 7, the combination of fungal cell wall degrading enzyme and antifungal fungal cell membrane affecting compound inhibit spore germination of *B. cinerea* more strongly than each agent alone. As further indicated in FIG. 7, gramicidin alone was able to provide 20–25% inhibition of spore germination of *B. cinerea* and fungal cell wall degrading enzyme was able to improve the inhibition to a level of about 100%.

EXAMPLE VIII

This experiment tested the effect of glucosidase from *T. harzianum* strain P1 (glucose T) on the inhibition of spore germination of *F. oxysporum* strain FOP1 by gramicidin.

Assays were carried out by the procedure described in the summary of the invention section. Dose response curves were obtained by probit analysis of data collected from two separate experiments with each experiment involving three treatment replicates.

Figure 8:
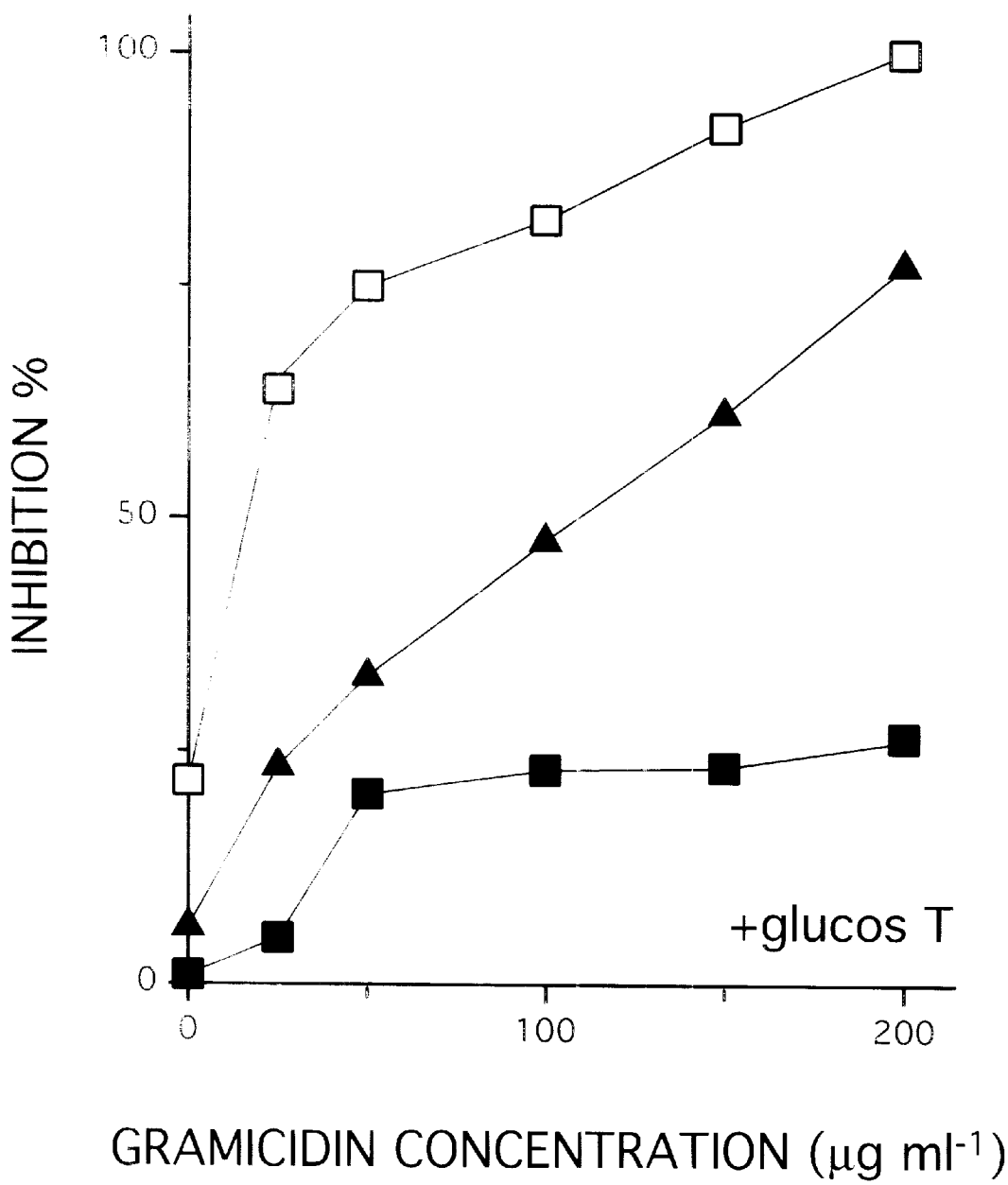
FIG. 8 is a set of graphs of gramicidin concentration versus percent inhibition of spore germination of F. oxysporum with concentration of glucosidase from T. harzianum strain P1 varied and shows results of Example VIII.

FIG. 8 shows the results. In FIG. 8, the filled in squares represent data points where glucos T was present in the assay mixture at a concentration of 0 μg/ml, the filled in triangles represent data points where glucos T was present in the assay mixture at a concentration of 10 μg/ml and the open squares represent data points where glucos T was present in the assay mixture at a concentration of 25 μg/ml.

As indicated in FIG. 8, the combination of fungal cell wall degrading enzyme and antifungal fungal cell membrane affecting compound inhibit spore germination of *F. oxysporum* more strongly than each. agent alone. As further indicated in FIG. 8, gramacidin alone was able to provide 20–25% inhibition of spore germination of *F. oxysporum* and fungal cell wall degrading enzyme was able to improve the inhibition to a level of about 100%.

EXAMPLE IX

This experiment tested the effect of endochitinase from *G. virens* strain 41 (endoc G) on the inhibition of spore germination of *B. cinerea* strain 12 by valinomycin.

Assays were carried out by the procedure described in the summary of the invention section. Dose response curves were obtained by probit analysis of data collected from two separate experiments with each experiment involving three treatment replicates.

Figure 9:
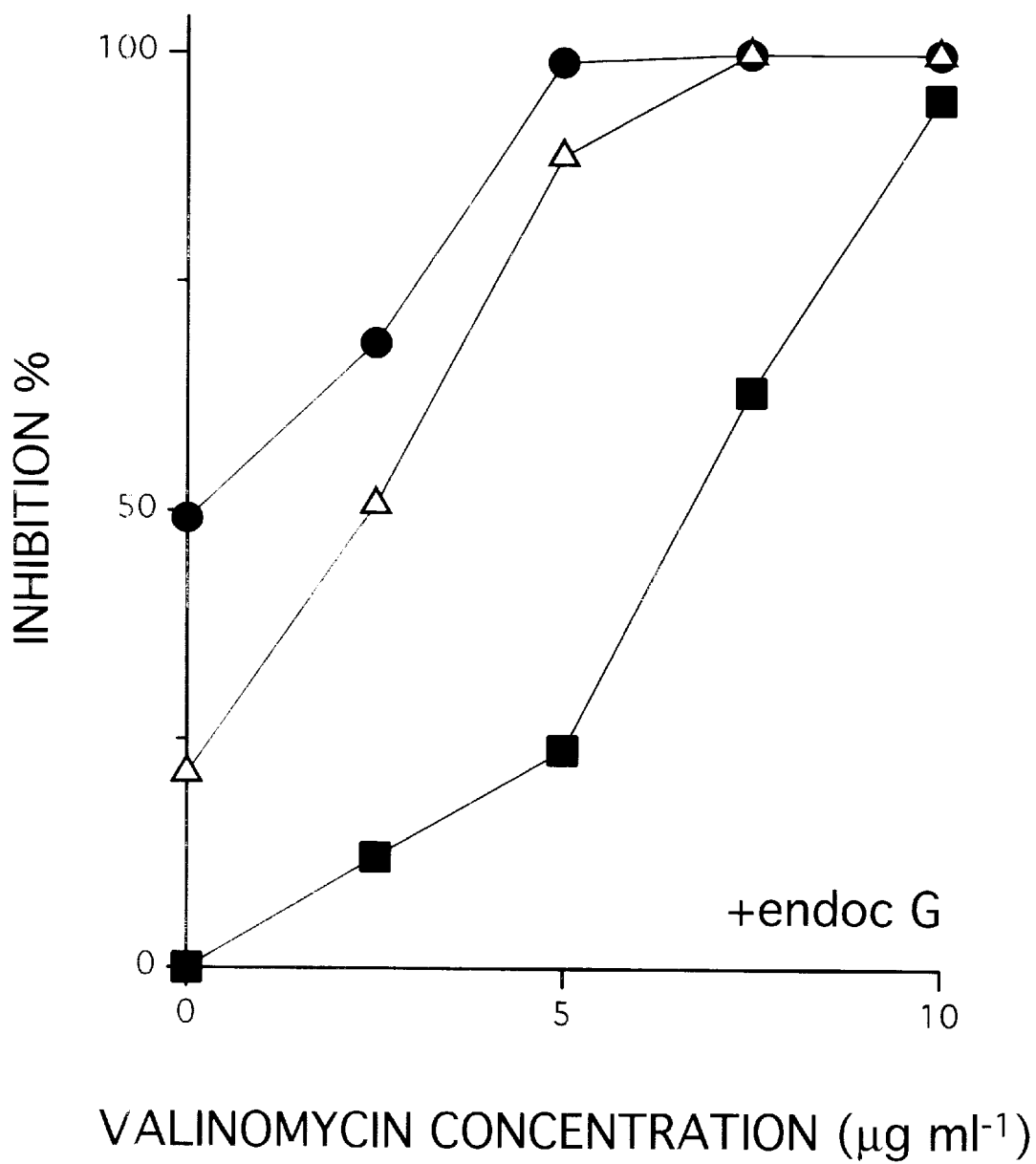
FIG. 9 is a set of graphs of valinomycin concentration versus percent inhibition of spore germination of B. cinerea with shows results of Example IX.

FIG. 9 shows the results. In FIG. 9, the filled in squares represent data points where endoc G was present in the assay mixture at a concentration of 0 μg/ml, the open triangles represent data points where endoc G was present in the assay mixture at a concentration of 2.5 μg/ml and the filled in circles represent data points where endoc G was present in the assay mixture at a concentration of 5 μg/ml.

As indicated in FIG. 9, the combination of fungal cell wall degrading enzyme and antifungal fungal cell membrane affecting compound inhibit spore germination of *B. cinerea* more strongly than each agent alone.

EXAMPLE X

This experiment tested the effect of glucosidase from *T. harzianum* strain P1 (glucos T) on the inhibition of spore germination of *F. oxysporum* strain FOP1 by valinomycin.

Assays were carried out by the procedure described in the summary of the invention section. Dose response curves were obtained by probit analysis of data collected from two separate experiments with each experiment involving three treatment replicates.

Figure 10:
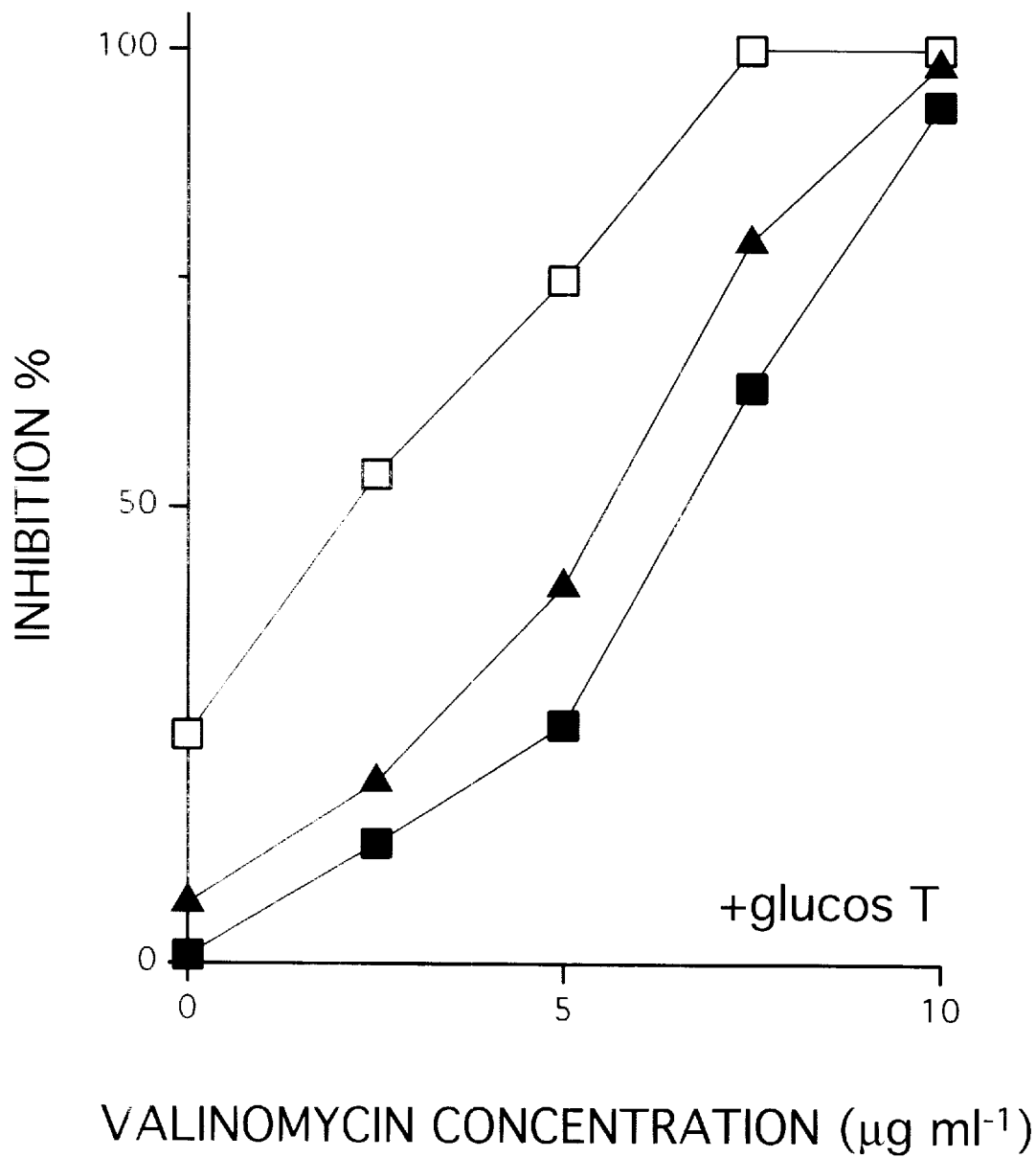
FIG. 10 is a set of graphs of valinomycin concentration versus percent inhibition of spore germination of F. oxysporum with concentration of glucosidase from T. harzianum strain P1 varied and shows results of Example X.

FIG. 10 shows the results. In FIG. 10, the filled in squares represent data points where glucos T was present in the assay mixture at a concentration of 0 μg/ml, the filled in triangles represent data points where glucose T was present in the assay mixture at a concentration of 10 μg/ml and the open squares represent data points where glucos T was present in the assay mixture at a concentration of 25 μg/ml.

As indicated in FIG. 10, the combination of fungal cell wall degrading enzyme and antifungal fungal cell membrane affecting compound inhibit spore germination of *F. oxysporum* more strongly than each agent alone.

EXAMPLE XI

This experiment tested the effect of endochitinase from *T. harzianum* strain P1 (endoc T) on the inhibition of spore germination of *B. cinerea* strain 12 by phospholipase B.

Assays were carried out by the procedure described in the summary of the invention section. Dose response curves were obtained by probit analysis of data collected from two separate experiments with each experiment involving three treatment replicates.

Figure 11:
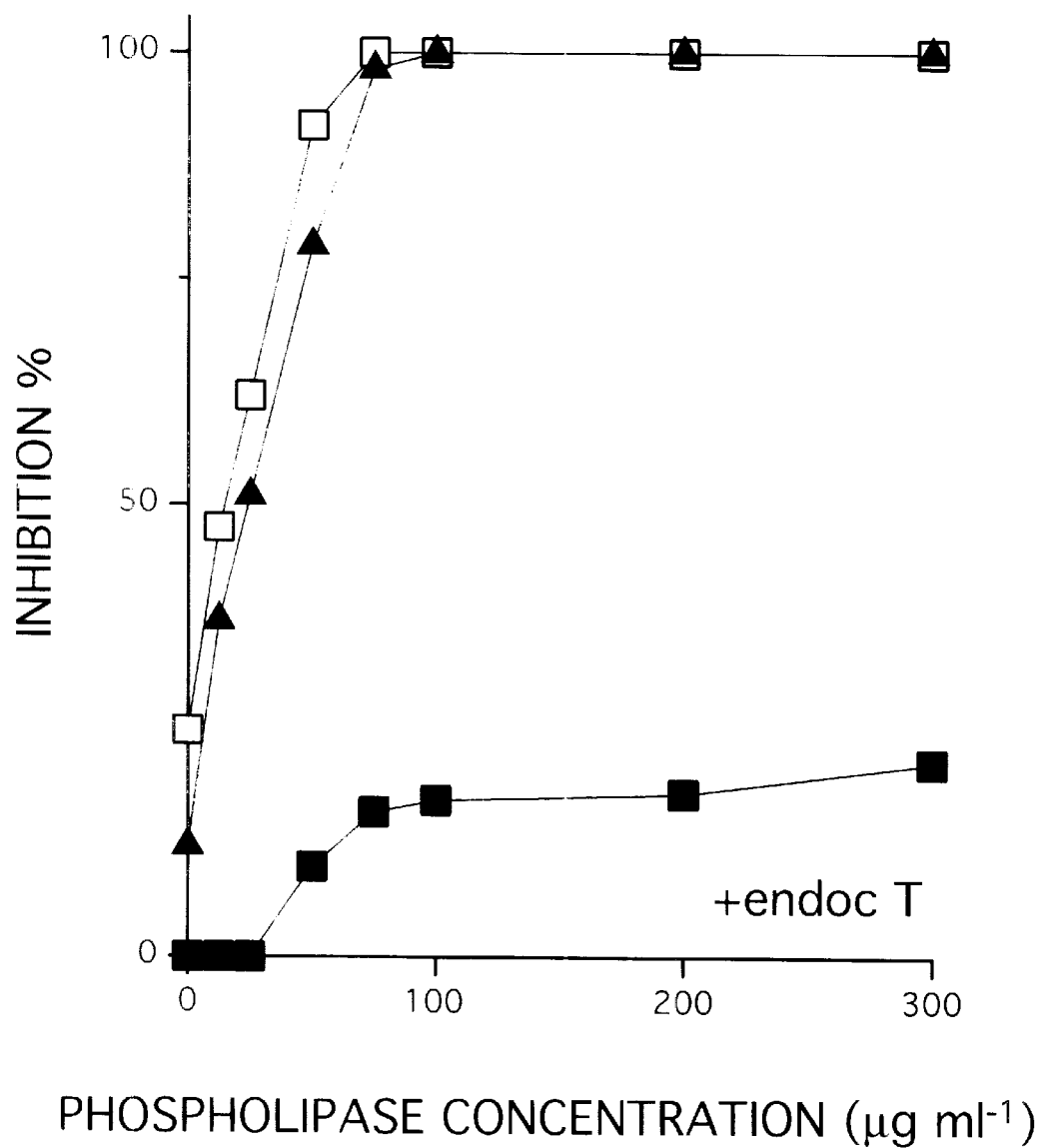
FIG. 11 is a set of graphs of phospholipase B concentration versus percent inhibition of spore germination of B. cinerea with concentration of endochitinase from T. harzianum strain P1 varied and shows results of Example XI.

FIG. 11 shows the results. In FIG. 11, the filled in squares represent data points where endoc T was present in the assay mixture at a concentration of 0 μg/ml, the filled in triangles represent data points where endoc T was present in. the assay mixture at a concentration of 10 μg/ml and the open squares represent data points where endoc T was present in the assay mixture at a concentration of 25 μg/ml.

As indicated in FIG. 11, the combination of fungal cell wall degrading enzyme and antifungal fungal cell membrane affecting compound inhibit spore germination of *B. cinerea* more strongly than each agent alone. As further indicated in FIG. 11, phospholipase B alone was able to provide 15–20% inhibition of spore germination of *B. cinerea* and fungal cell wall degrading enzyme was able to improve the inhibition to a level of about 100%.

EXAMPLE XII

This experiment tested the effect of chitobiosidase from *S. albidoflavus* NRRL B-16746 (chitob S) on the inhibition of spore germination of *B. cinerea* strain 12 by phospholipase B.

Assays were carried out by the procedure described in the summary of the invention section. Dose response curves were obtained by probit analysis of data collected from two separate experiments with each experiment involving three treatment replicates.

Figure 12:
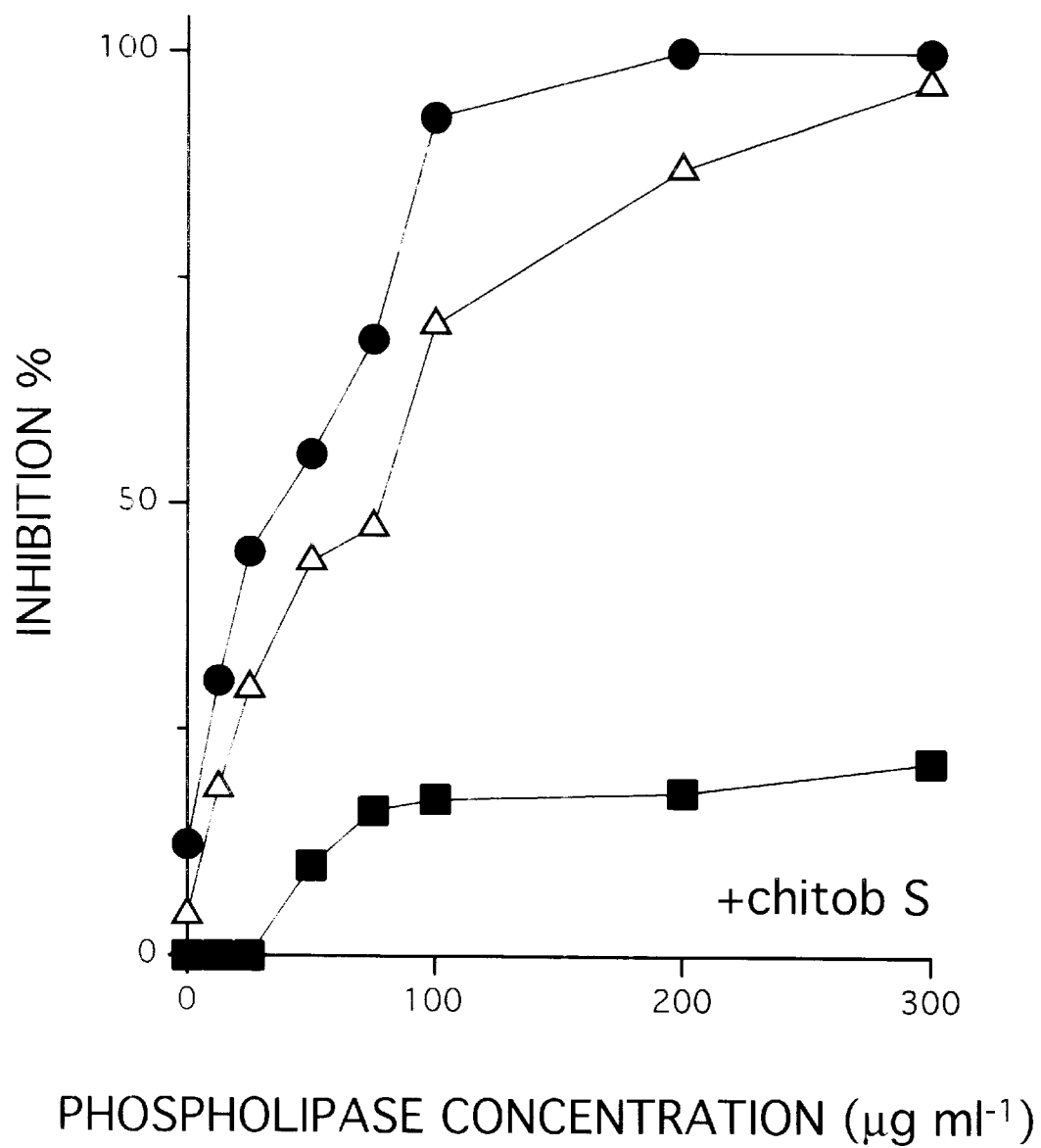
FIG. 12 is a set of graphs of phospholipase B concentration versus percent inhibition of spore germination of B. cinerea with concentration of chitobiosidase from S. albidoflavus NRRL B-16746 varied and shows results of Example XII.

FIG. 12 shows the results. In FIG. 12, the filled in squares represent data points where chitob S was present in the assay mixture at a concentration of 0 μg/ml, the open triangles represent data points where chitob S was present in the assay mixture at a concentration of 2.5 μg/ml and the filled in circles represent data points where chitob S was present in the assay mixture at a concentration of 5 μg/ml.

As indicated in FIG. 12, the combination of fungal cell wall degrading enzyme and antifungal fungal cell membrane affecting compound inhibit spore germination of *B. cinerea* more strongly than each agent alone. As further indicated in FIG. 12, phospholipase B alone was able to provide 15–20% inhibition of spore germination of *B. cinerea* and fungal cell wall degrading enzyme was able to improve the inhibition to a level of about 100%.

EXAMPLE XIII

This experiment tested the effect of endochitinase from *G. virens* strain 41 (endoc G) on the inhibition of spore germination of *F. oxysporum* strain FOP1 by trichorzianine A1.

Assays were carried out by the procedure described in the summary of the invention section. Dose response curves were obtained by probit analysis of data collected from two separate experiments with each experiment involving three treatment replicates.

Figure 13:
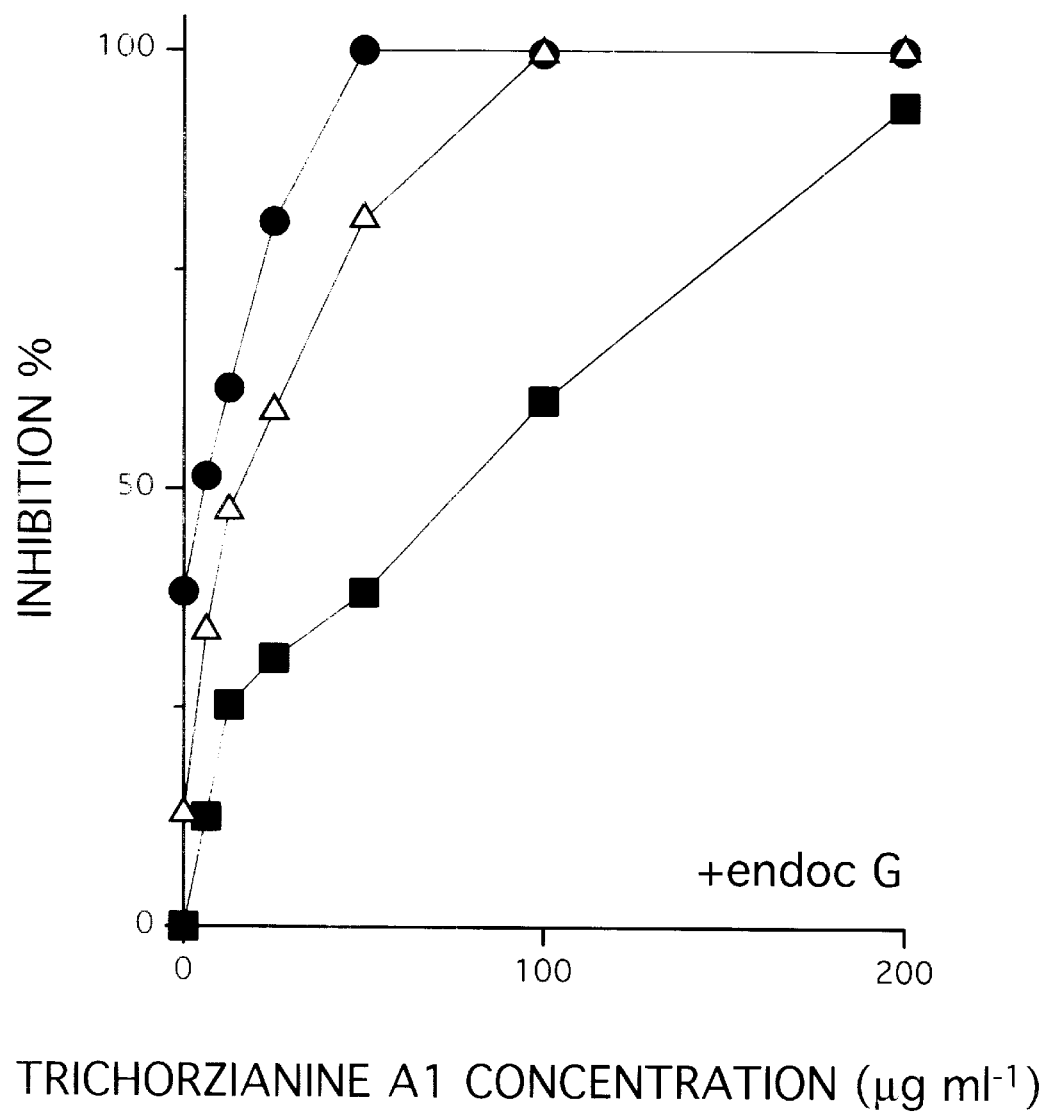
FIG. 13 is a set of graphs of trichorzianine A1 concentration versus percent inhibition of F. oxysporum with concentration of endochitinase from G. virens strain 41 varied and shows results of Example XIII.

FIG. 13 shows the results. In FIG. 13, the filled in squares represent data points where endoc G was present in the assay mixture at a concentration of 0 μg/ml, the open triangles represent data points where endoc G was present in the assay mixture at a concentration of 2.5 μg/ml and the filled in squares represent data points where endoc G was present in the assay mixture at a concentration of 5 μg/ml.

As indicated in FIG. 13, the combination of fungal cell wall degrading enzyme and antifungal fungal cell membrane affecting compound inhibit spore germination of *F. oxysporum* more strongly than each agent alone.

EXAMPLE XIV

This experiment tested the effect of nagase from *T. harzianum* strain P1 (NAGas T) on the inhibition of spore germination of *F. oxysporum* strain FOP1 by trichorzianine A1.

Assays were carried out by the procedure described in the summary of the invention section. Dose response curves were obtained by probit analysis of data collected from two separate experiments with each experiment involving three treatment replicates.

Figure 14:
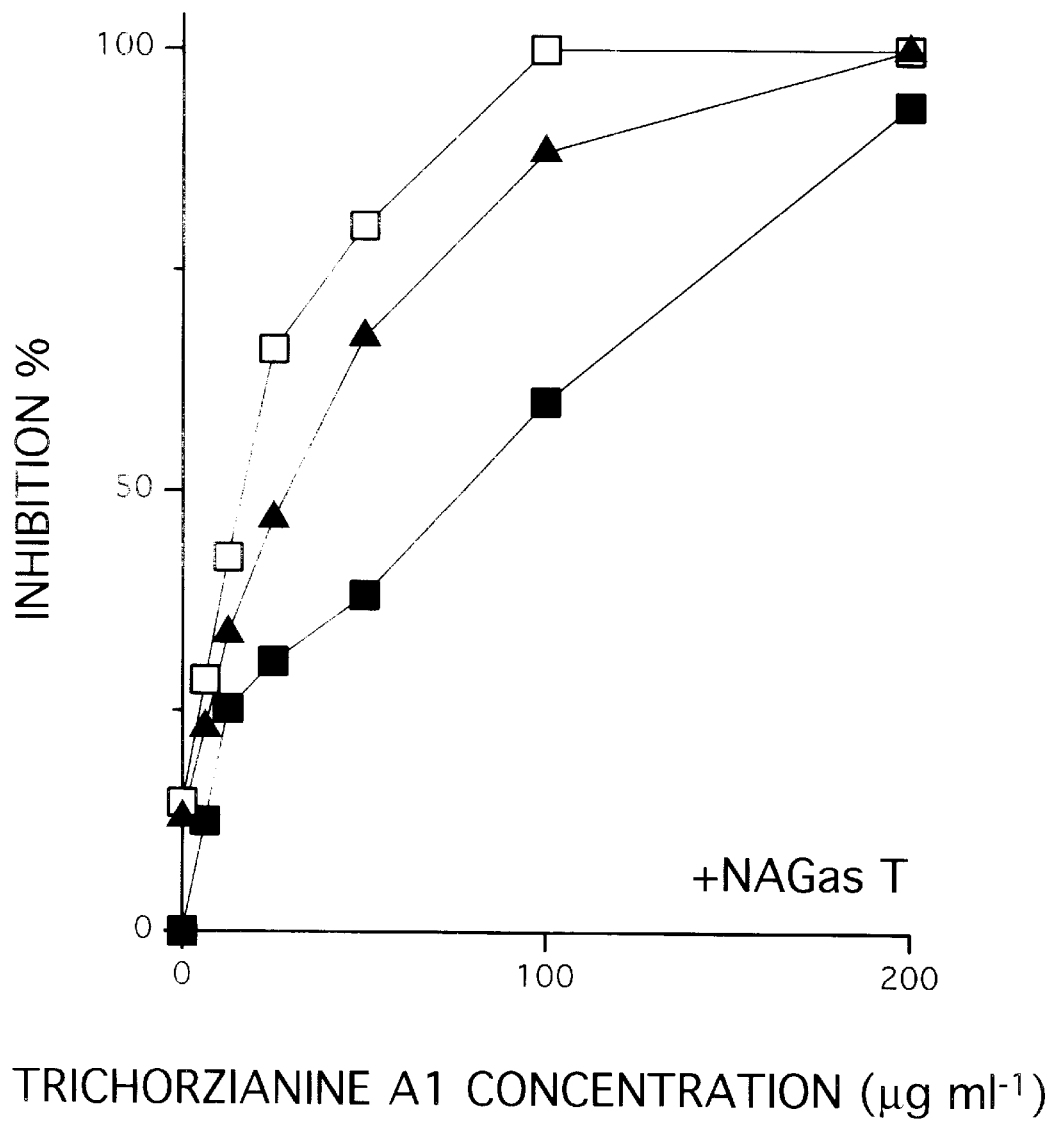
FIG. 14 is a set of graphs of trichorzianine A1 concentration versus percent inhibition of F. oxysporum with concentration of nagase from Trichoderma harzianum strain P1 varied and shows results of Example XIV.
Figure 15:
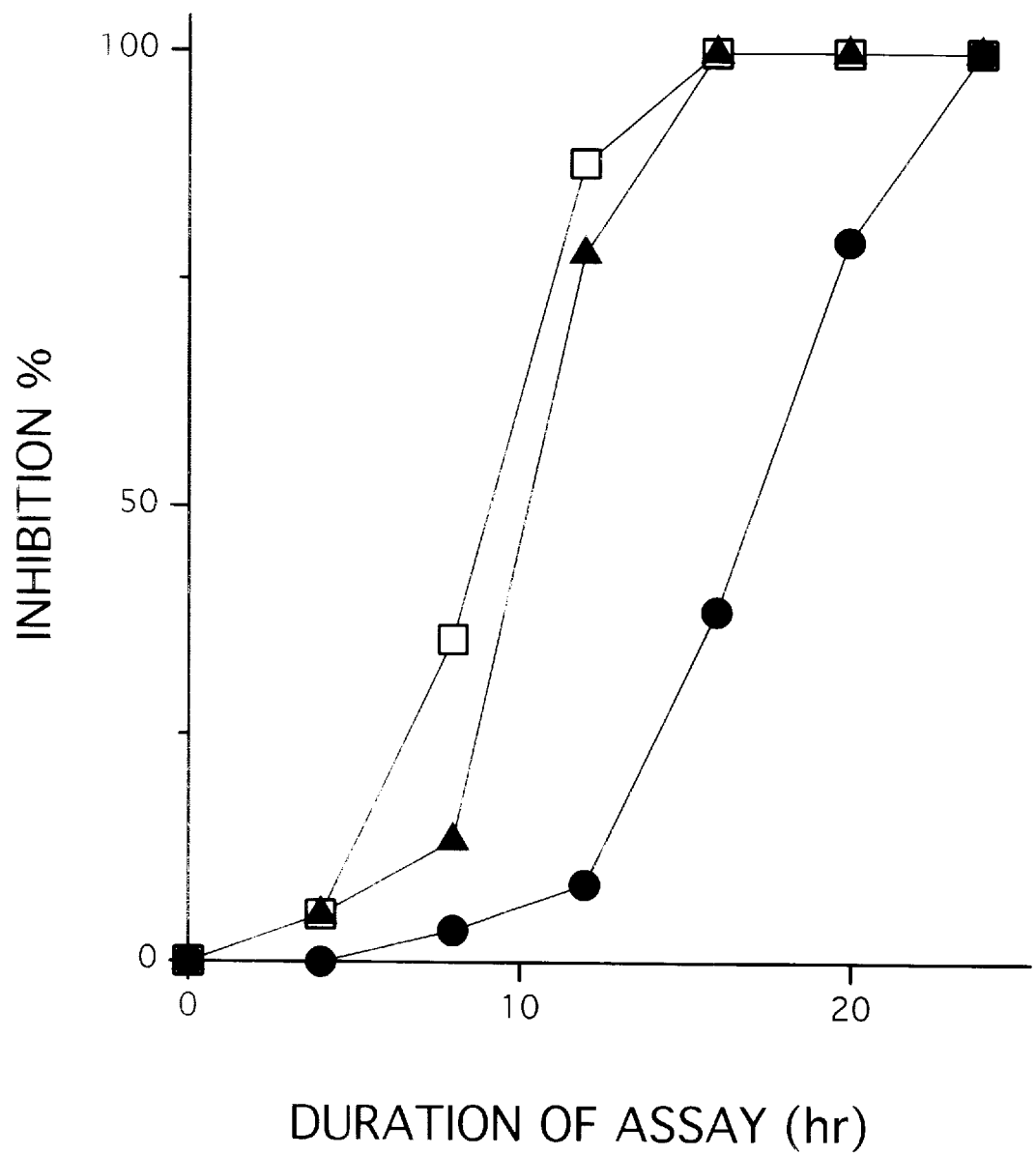
FIG. 15 is a set of graphs of duration of assay versus percent relative time of application of antifungal fungal cell membrane affecting compound osmotin I and fungal cell wall degrading enzyme endochitinase from *Nicotiana tabacum* cv. Havana 425 and shows results of one experiment of Example XV.
Figure 16:
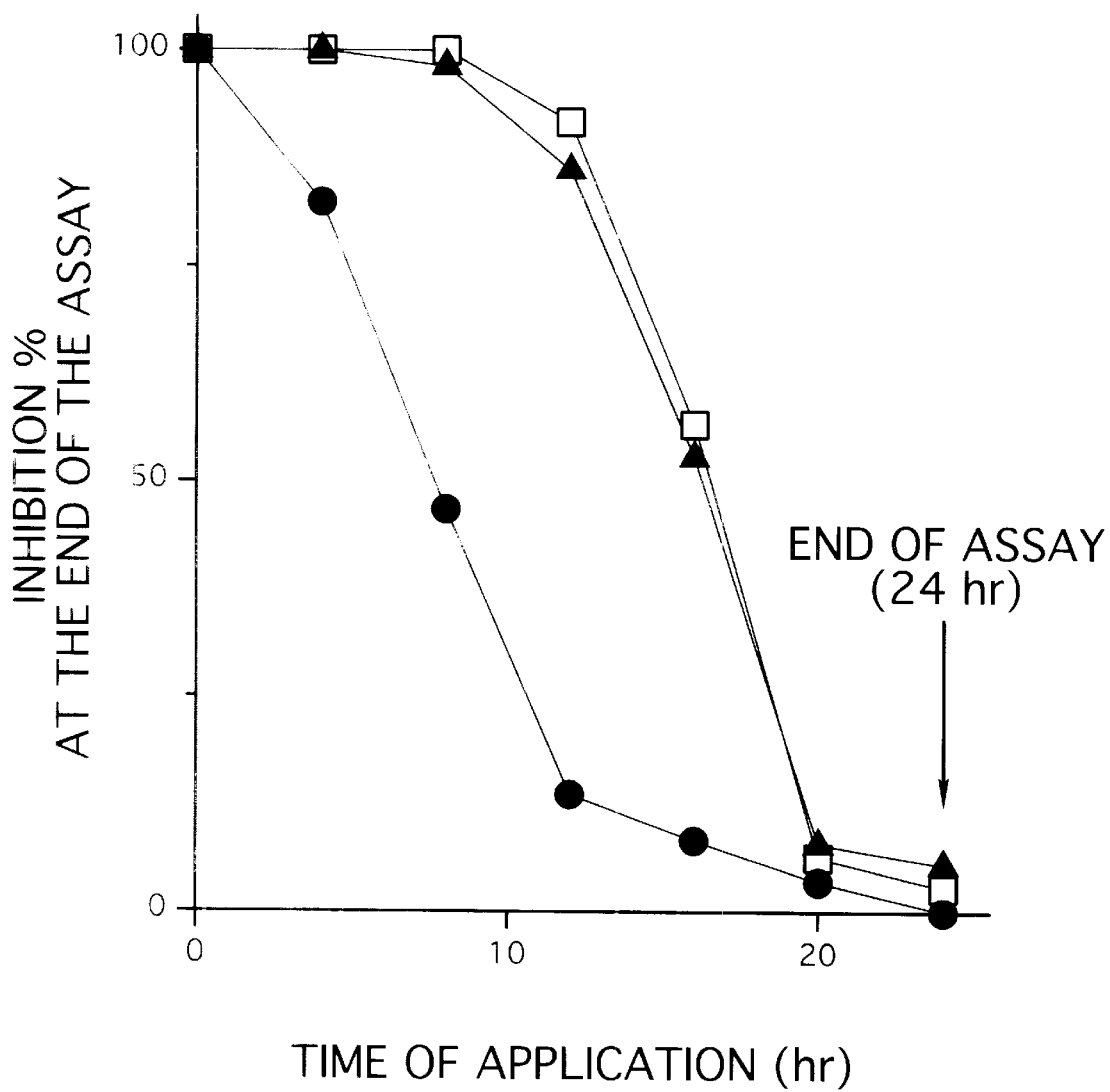
FIG. 16 is a set of graphs of time of application versus percent inhibition obtained at the end of 24 hours where each of the graphs represents a variation in relative time of application of antifungal fungal cell membrane affecting compound osmotin I and fungal cell wall degrading enzyme endochitinase from *Nicotiana tabacum* cv. Havana 425 and shows results of a second experiment of Example XV.

FIG. 14 shows the results. In FIG. 14, the filled in squares represent data points where NAGas T was present in the assay mixture at a concentration of 0 µg/ml, the filled in triangles represent data points where NAGas T was present in the assay mixture at a concentration of 10 µg/ml and the open squares represent data points where NAGas T was present in the assay mixture at a concentration of 25 µg/ml.

As indicated in FIG. 14, the combination of fungal cell wall degrading enzyme and antifungal fungal cell membrane affecting compound inhibit spore germination of *F. oxysporum* more strongly than each agent alone.

EXAMPLE XV

This example compares the effect of varying the time of application of fungal cell wall degrading enzyme and antifungal fungal cell membrane affecting compound on inhibition of spore germination of *B. cinerea*.

Assays were carried out by the procedure described in the summary of invention section. Time response curves were obtained by probit analysis of data collected from two separate experiments with three treatment replicates in each experiment.

The fungal cell wall degrading enzyme was endochitinase activity from *Nicotiana tabacum* cv. Havana 425 as described. above (endoc P).

The antifungal fungal cell membrane affecting compound was osmotin I.

The endoc P was used at a concentration of 32 μg/ml. The osmotin I was used at a concentration of 0.5 μg/ml. At these concentrations, the two agents applied concurrently gave 100% inhibition and the agents applied singly gave low inhibitions.

In one experiment, in one run, endoc P and osmotin I were applied at time 0; in another run, endoc P was applied at time 0 and osmotin I 8 hours later; and in another run, osmotin I was applied at time 0 and endoc P was applied 8 hours later. The results are shown in FIG. 15. In FIG. 15, the open squares denote data points for the run where endoc. P and osmotin I were applied at time 0, the filled in triangles denote data points where endoc P was applied at time 0 and osmotin I was applied 8 hours later and the filled in circles represent data points where osmotin I was applied at time 0 and endoc P was applied 8 hours later. As indicated in FIG. 15, if the antifungal fungal cell membrane affecting compound is applied 8 hours after the application of the fungal cell wall degrading enzyme, the resulting curve is substantially the same as if the two kinds of agents were both applied at the beginning of the assay. On the other hand, when the cell wall degrading enzyme was applied 8 hours after the application of the antifungal fungal cell membrane affecting compound, there is reduction in percentage inhibition obtained compared to when the two kinds of agents were both applied at the beginning of the assay until both kinds of agents have been in contact with the fungus for at least about 16 hours.

Consistent results were obtained for the inhibition of either spore germination or germ tube elongation with 15 different combinations of antifungal fungal cell membrane affecting compound and fungal cell wall degrading enzyme including besides that set forth. above, gliotoxin/endochitinase from *G. virens* strain 41, gliotoxin/glucosidase from *T. harzianum* strain P1, osmotin I/endochitinase from *T. harzianum* strain P1, trichorzianine A1/endochitinase from *T. harzianum* strain P1, trichorzianine B1/nagase from *T. harzianum* strain P1, flusilazole/endochitinase from *G. virens* strain 41 and miconazole/endochitinase from *T. harzianum* strain P1.

In another experiment, inhibitions obtained at the end of the standard bioassay (24 hours) versus time of application for both agents together, endoc P at time 0 and osmotin I at different times, and osmotin I applied at time 0 and endoc P applied at different times, were determined. The results are set forth in FIG. 16 wherein the open boxes denote data points for application of both compounds together, the filled in triangles denote data points for application of endoc P at time 0 and osmotin I applied at different times and the filled in circles denote data points for application at time 0 and endoc P at different times. Similar curves to those in FIG. 16 were obtained for other antifungal fungal cell membrane affecting compound-fungal cell wall degrading enzyme combinations.

EXAMPLE XVI

Each of 8 antifungal fungal cell membrane affecting compounds were used in combination with each of 8 or 6 fungal cell wall degrading enzymes to provide 50% inhibition ($ED_{50}$) of *B. cinerea* strain 12 spore germination. Each fungal cell wall degrading enzyme was used at a concentration giving 10% inhibition of spore germination when used alone in combination with an amount of antifungal fungal cell membrane affecting compound so the combination gave 50% inhibition of spore germination.

The antifungal fungal cell membrane affecting compounds employed were osmotin I, gramicidin, valinomycin, phospholipase B (phospholip in tables below), trichorzianine A1 (trich. A1 in tables below), trichorzianine B1 (trich. B1 in tables below), flusilazole and miconazole.

The fungal cell wall degrading enzymes employed were endochitinase from *T. harzianum* strain P1 as described above (Endoc T below), endochitinase from *G. virens* strain 41 as described above (Endoc G below), endochitinase from *Nicotiana tabacum* cv. Havana 425 as described above (Endoc P below), chitobiosidase from *T. harzianum* strain P1 as described above (Chitob T below), chitobiosidase from *G. virens* strain 41 as described above (Chitob G below), chitobiosidase from *S. albidoflavus* NRRL B-16746 as described above (Chitob S below), nagase from *Trichoderma harzianum* strain P1 as described above (NAGas T below) and glucosidase from *Trichoderma harzianum* strain P1 as described above (Glucos T below).

Dose response curves were determined for each antifungal fungal cell membrane affecting compound and for each fungal cell wall degrading enzyme singly. Then each fungal cell wall degrading enzyme at a concentration giving 10% inhibition when used alone was combined with with increasing amounts of antifungal fungal cell membrane affecting compound. Then the concentration of antifungal fungal cell membrane affecting compound causing the $ED_{50}$ for each combination was calculated by probit analysis of data collected from two experiments with three treatment replicates for each experiment. Assays for inhibition of spore germination were carried out as described in the summary of invention section above.

The relative level of synergism (RS below) for each combination was calculated by applying Limpel's formula: Ee=X+Y-(XY/100) as described in Richer, D. L, Pestic. Sci. 19, 309–315, 1987. In Limpel's formula, X and Y are the percentages of inhibition relative to each compound used alone and Ee is the expected effect for an additional (non-synergistic) effect. If the combination of the two agents produces an observed effect (Eo) greater than Ee, synergism exists, and as the difference between Eo and Ee increases, the level of synergism is greater. In this experiment, the X value (percentage inhibition by fungal cell wall degrading enzyme when used alone was chosen to be 10 (10% inhibition of spore germination when used alone) and the observed effect, Eo, was 50 (i.e., 50% inhibition of spore germination). The Y values were obtained from the determined concentrations of antifungal cell membrane affecting compound causing the $ED_{50}$ for a combination and the dose response curves for the antifungal cell membrane affecting compound used alone—i.e., the Y value was the percent inhibition for the antifungal fungal cell membrane affecting compound when used alone for the concentration of antifungal fungal cell membrane affecting compound that was determined to cause the $ED_{50}$ for the combination. Ee values were then calculated from Limpel's formula. The relative level of synergism, Eo–Ee, is Eo–(X+Y–(XY/100)) or in this case 50–(10+Y–Y/10) where Y is as described above. If no synergism exists, the RS value approaches zero while 40 is the highest possible value.

Results for $ED_{50}$ and RS are given in tables below. The upper and lower 95% fiducial limits for 95% probability for $ED_{50}$ and RS are given in parenthesis after the value listed.

The concentration of each cell wall degrading enzyme used (i.e., corresponding to an $ED_{10}$ for the enzyme alone) were as follows: Endoc T, 11 µg/ml; Endoc G. 3.5 µg/ml; Chitob T, 25 µg/ml; Chitob G, 29 µg/ml; NAGas T, 17 µg/ml; Glucos T, 20 µg/ml; Endoc P, 32 µg/ml; Chitob S, 4 µg/ml.

The results are given in Table 14 below for the antifungal fungal cell membrane affecting compound osmotin I.

TABLE 14

| mixture of compounds | $ED_{50}$ (µg ml$^{-1}$) | RS |
|---|---|---|
| Osmotin + | 10.0 (8–12) | — |
| Endoc T | 0.7 (0.6–0.8) | 30.0 (34.6–27.4) |
| Endoc G | 0.5 (0.2–0.6) | 37.3 (40–34) |
| Chitob T | 1.0 (0.9–1.2) | 22.0 (23.8–21) |
| Chitob G | 3.0 (2.5–3.4) | 15.7 (17.5–13) |
| NAGas T | 0.6 (0.4–0.7) | 34.6 (36–30) |
| Glucos T | 0.3 (0.2–0.5) | 40.0 (40–37.3) |
| Endoc P | 0.3 (0.1–0.5) | 40.0 (40–37.3) |
| Chitob S | 5.0 (4.2–55) | 11.0 (13–10.4) |

Thus, for example, the concentration of osmotin for 50% inhibition of spore germination was reduced from 10.0 µg/ml to 0.3 µg/ml by the inclusion of 32 µg/ml of Endoc P.

The results are given in Table 15 below for the antifungal fungal cell membrane affecting compound gramicidin.

TABLE 15

| mixture of compounds | $ED_{50}$ (µg ml$^{-1}$) | RS |
|---|---|---|
| Gramicidin + | >300 | — |
| Endoc T | 25 (20–29) | 34.6 (36.4–30.1) |
| Endoc G | 28 (25–30) | 31.0 (34.6–29.2) |

TABLE 15-continued

| mixture of compounds | $ED_{50}$ (µg ml$^{-1}$) | RS |
|---|---|---|
| Chitob T | 47 (46–49) | 22.9 (24.7–22.1) |
| Chitob G | 60 (57–62) | 17.5 (21.2–16.6) |
| NAGas T | 30 (29–31) | 29.2 (30.1–28.3) |
| Glucos T | 27 (24–29) | 32.8 (35.5–30.1) |
| Endoc P | 47 (44–49) | 22.9 (24.7–22.1) |
| Chitob S | 30 (27–33) | 29.2 (32.8–28.3) |

The results are given in Table 16 below for the antifungal fungal cell membrane affecting compound valinomycin.

TABLE 16

| mixture of compounds | $ED_{50}$ (µg ml$^{-1}$) | RS |
|---|---|---|
| Valinomycin + | 7.3 (7.0–7.6) | — |
| Endoc T | 1.0 (0.9–1/1) | 40.0 (+0–39.1) |
| Endoc G | 1.5 (1.3–1.7) | 36.4 (39.1–35.5) |
| Chitob T | 5.1 (4.8–5.3) | 26.5 (28.3–22) |
| Chitob G | 5.5 (5.4–5.7) | 23.8 (24.7–18.4) |
| NAGas T | 1.8 (1.7–1.9) | 32.8 (35.5–31.9) |
| Glucos T | 1.2 (1.0–1.4) | 39.1 (40–37.3) |
| Endoc P | 2.5 (2.2–2.6) | 29.2 (31–28.3) |
| Chitob S | 5.6 (5.5–5.7) | 19.7 (23.8–18.4) |

The results are given in Table 17 below for the antifungal cell membrane affecting compound phospholipase B.

TABLE 17

| mixture of compounds | $ED_{50}$ (µg ml$^{-1}$) | RS |
|---|---|---|
| Phospholip + | >300 | — |
| Endoc T | 25 (21–28) | 40.0 (40–40) |
| Endoc G | 40 (36–44) | 38.2 (40–31.9) |
| Chitob T | 55 (51–58) | 31.0 (31.9–29.2) |
| Chitob G | 43 (42–46) | 32.8 (34.6–31.9) |
| NAGas T | 32 (29–34) | 40.0 (40–40) |
| Glucos T | 31 (30–32) | 40.0 (40–40) |
| Endoc P | 120 (107–139) | 22.9 (23.8–18.4) |
| Chitob S | 63 (60–66) | 26.1 (26.5–25.6) |

The results are given in Table 18 below for the antifungal fungal cell membrane affecting compound trichorzianine A1.

TABLE 18

| mixture of compounds | $ED_{50}$ (µg ml$^{-1}$) | RS |
|---|---|---|
| Trich. A1 + | 90.5 (85–95) | — |
| Endoc T | 13.0 (11–14.8) | 20.2 (23–20) |
| Endoc G | 13.1 (10.5–15) | 20.0 (23.8–19) |
| Chitob T | 27.0 (24.5–29) | 15.3 (17.5–14) |
| Chitob G | 29.0 (26–32) | 14.0 (16.6–13) |
| NAGas T | 22.2 (20–24) | 18.3 (19–17) |
| Glucos T | 22.0 (19–25) | 18.5 (19–17.5) |
| Endoc P | 29 (26.5–31) | 14.0 (16.5–12) |
| Chitob S | 20.1 (18–22) | 19.1 (18–18.5) |

The results are given in Table 19 below for the antifungal fungal cell membrane affecting compound trichorzianine B1.

TABLE 19

| mixture of compounds | $ED_{50}$ ($\mu g\ ml^{-1}$) | RS |
|---|---|---|
| Trich. B1 + | 95.2 (92–99) | — |
| Endoc T | 25 (23–27) | 23.8 (25.6–22) |
| Endoc G | 30 (28–31.5) | 19.5 (21–18) |
| Chitob T | 35 (34–36) | 16.8 (15–17) |
| Chitob G | 36 (33–38.5) | 16.5 (18–15.5) |
| NAGas T | 28 (24–31) | 21.9 (26–18) |
| Glucos T | 33 (32–34) | 17.3 (18–17) |
| Endoc P | 52 (50–55) | 11.2 (13–10) |
| Chitob S | 30 (27–31) | 19.5 (22–18) |

The results are given in Table 20 below for the antifungal fungal cell membrane affecting compound flusilazole.

TABLE 20

| mixture of compounds | $ED_{50}$ ($ng\ ml^{-1}$) | RS |
|---|---|---|
| Flusilazole + | 68 (61–85) | — |
| Endoc T | 0.6 (0.4–0.8) | 40 (40–39) |
| Endoc G | 0.7 (0.7–0.8) | 46 (40–39) |
| Chitob T | 1.9 (1.6–2.1) | 32.8 (34–30) |
| Chitob G | 5 (4–6.5) | 23.8 (26–20) |
| NAGas T | 0.9 (0.8–1) | 38.8 (39–37) |
| Glucos T | 0.8 (0.7–1) | 39 (40–37) |

The results are given in Table 21 below for the antifungal fungal cell membrane affecting compound miconazole.

TABLE 21

| mixture of compounds | $ED_{50}$ ($ng\ ml^{-1}$) | RS |
|---|---|---|
| Miconazole + | 3.0 (2–4) | — |
| Endoc T | 0.07 (0.06–0.08) | 37.3 (39–36) |
| Endoc G | 0.01 (0.01–0.03) | 39.5 (40–39) |
| Chitob T | 0.06 (0.04–0.08) | 38.2 (39–36) |
| Chitob G | 0.06 (0.05–0.07) | 38.2 (39–36) |
| NAGas T | 0.1 (0.06–0.2) | 36.4 (39–31) |
| Glucos T | 0.2 (0.1–0.3) | 31 (32–30) |

EXAMPLE XVII

An experiment was carried out the same as in Example XVI except that the fungus used in the inhibition testing was *Fusarium oxysporum* strain FOP1.

The concentrations of each fungal cell wall degrading enzyme used (i.e., corresponding to an $ED_{10}$ for the enzyme alone) were as follows: Endoc T,. 10 $\mu g/ml$; Endoc G, 5 $\mu g/ml$; Chitob T, 30 $\mu g/ml$; Chitob G, 33 $\mu g/ml$; NAGas T, 12 $\mu g/ml$; Glucos T, 14 $\mu g/ml$; Endoc P. 38 $\mu g/ml$; and Chitob S, 8 $\mu g/ml$.

The results are given in Table 22 below for the antifungal fungal cell membrane affecting compound osmotin I.

TABLE 22

| mixture of compounds | $ED_{50}$ ($ng\ ml^{-1}$) | RS |
|---|---|---|
| Osmotin + | 11.0 (8–12) | — |
| Endoc T | 0.2 (0.1–0.3) | 38.0 (40–36.4) |

TABLE 22-continued

| mixture of compounds | $ED_{50}$ ($ng\ ml^{-1}$) | RS |
|---|---|---|
| Endoc G | 0.2 (0.1–0.4) | 38.5 (40–34.5) |
| Chitob T | 0.9 (0.7–1.1) | 24.0 (26–21) |
| Chitob G | 1.0 (0.9–1.1) | 23.1 (24–21) |
| NAGas T | 0.6 (0.4–0.7) | 28.8 (34.5–26) |
| Glucos T | 0.1 (0.1–0.2) | 40.0 (40–38.5) |
| Endoc P | 0.1 (0.1–0.1) | 40.0 (40–40) |
| Chitob S | 2.3 (2.2–2.5) | 8.0 (11.2–6.5) |

The results are given in Table 23 below for the antifungal fungal cell membrane affecting compound gramicidin.

TABLE 23

| mixture of compounds | $ED_{50}$ ($ng\ ml^{-1}$) | RS |
|---|---|---|
| Gramicidin + | >300 | — |
| Endoc T | 30 (26–33) | 31.0 (32–22) |
| Endoc G | 18 (16–22) | 40.0 (40–38) |
| Chitob T | 97 (95–100) | 12.0 (13–11) |
| Chitob G | 102 (97–112) | 10.0 (11–5.5) |
| NAGas T | 32 (29–35) | 22.8 (25–20) |
| Glucos T | 26 (23–29) | 32.0 (34–25) |
| Endoc P | 110 (104–121) | 6.0 (8–5) |
| Chitob S | 27 (23–30) | 30.4 (34–24) |

The results are given in Table 24 below for the antifungal fungal cell membrane affecting compound valinomycin.

TABLE 24

| mixture of compounds | ED ($ng\ ml^{-1}$) | RS |
|---|---|---|
| Valinomycin + | 8.5 (8.0–9.0) | — |
| Endoc T | 1.5 (1.4–1.7) | 31.9 (34–28.5) |
| Endoc G | 1.0 (0.3–1.2) | 40.0 (40–38.5) |
| Chitob T | 2.5 (2.1–2.7) | 25.0 (27–23.5) |
| Chitob G | 3.0 (2.9–3.1) | 20.4 (21.5–19) |
| NAGas T | 3.5 (3.3–3.7) | 18.2 (18.5–17) |
| Glucos T | 1.1 (1.0–1.3) | 40.0 (40–38) |
| Endoc P | 4.0 (3.9–4.1) | 7.6 (9–6) |
| Chitob S | 1.6 (1.5–1.7) | 30.0 (31.9–28.5) |

The results are given in Table 25 below for the antifungal fungal cell membrane affecting compound phospholipase B.

TABLE 25

| mixture of compounds | $ED_{50}$ ($ng\ ml^{-1}$) | RS |
|---|---|---|
| Phospholip + | >300 | — |
| Endoc T | 29 (26–31) | 40.0 (40–38.5) |
| Endoc G | 35 (31–38) | 37.5 (38.5–34) |
| Chitob T | 49 (45–55) | 30.5 (31–27) |
| Chitob G | 65 (57–70) | 20.4 (22–19) |
| NAGas T | 40 (35–44) | 32.8 (37.5–31.2) |
| Glucos T | 49 (40–55) | 30.5 (32.8–27) |
| Endoc P | 70 (67–79) | 19.0 (19.5–18.5) |
| Chitob S | 44 (38–50) | 31.2 (34–29) |

The results are given in Table 26 below for the antifungal fungal cell membrane affecting compound trichorzianine A1.

TABLE 26

| mixture of compounds | ED$_{50}$ (ng ml$^{-1}$) | RS |
|---|---|---|
| Trich. A1 | 87 (83–91) | — |
| Endoc T | 10 (9–11.8) | 17.5 (23–15.5) |
| Endoc G | 3 (2.5–3.5) | 30.5 (33–28.5) |
| Chitob T | 12 (10.5–13.5) | 15.8 (18–13) |
| Chitob G | 15 (11–19) | 10.2 (16–7) |
| NAGas T | 14 (12–16) | 13.2 (15.8–9.5) |
| Glucos T | 8 (7–9) | 27.5 (30–23) |
| Endoc P | 12 (10.5–14) | 15.2 (18–13.2) |
| Chitob S | 11 (10–13) | 16.0 (18–13.5) |

The results are given in Table 27 below for the antifungal fungal cell membrane affecting compound trichorzianine B1.

TABLE 27

| mixture of compounds | ED$_{50}$ (ng ml$^{-1}$) | RS |
|---|---|---|
| Trich. B1 | 95.5 (92–99) | — |
| Endoc T | 15 (10–19) | 16.0 (23–13) |
| Endoc G | 10 (8–11.5) | 23.0 (25.5–21) |
| Chitob T | 22 (20–24) | 10.0 (12–8.5) |
| Chitob G | 24 (21–27) | 8.5 (11–7.5) |
| NAGas T | 20 (18–22) | 12.0 (14–10) |
| Glucos T | 11 (10–13) | 22.0 (23–21.5) |
| Endoc P | 20.5 (17–24) | 11.4 (15–8.5) |
| Chitob S | 20 (16–24) | 12.4 (16–8.5) |

The results are given in Table 28 below for the antifungal fungal cell membrane affecting compound flusilazole.

TABLE 28

| mixture of compounds | ED$_{50}$ (ng ml$^{-1}$) | RS |
|---|---|---|
| Flusilazole + | 59.0 (51–65) | — |
| Endoc T | 0.3 (0.1–0.5) | 40.0 (40–39) |
| Endoc G | 0.1 (0.1–0.2) | 40.0 (40–40) |
| Chitob T | 1.0 (0.8–1.2) | 34.0 (37–30) |
| Chitob G | 4.0 (3–4.5) | 28.5 (29–27) |
| NAGas T | 0.9 (0.8–1) | 35.5 (37–34) |
| Glucos T | 0.7 (0.6–0.8) | 38.5 (39–37) |

The results are given in Table 29 below for the antifungal fungal cell membrane affecting compound miconazole.

TABLE 29

| mixture of compounds | ED$_{50}$ (ng ml$^{-1}$) | RS |
|---|---|---|
| Miconazole + | 5.0 (4.5–5.5) | — |
| Endoc T | 0.1 (0.07–0.2) | 38.0 (39.5–36.5) |
| Endoc G | 0.06 (0.05–0.07) | 40.0 (40–40) |
| Chitob T | 0.6 (0.4–0.8) | 33.0 (34–27.5) |
| Chitob G | 0.7 (0.6–0.8) | 28.5 (33–27.5) |
| NAGas T | 0.4 (0.3–0.5) | 34.0 (35.5–33) |
| Glucos T | 0.3 (0.1–0.5) | 35.5 (38–33) |

EXAMPLE XVIII

This example shows the effect of the application of L-sorbose on the inhibition of spore germination and germ tube elongation of *B. cinerea*.

L-Sorbose was applied together with each of the fungal cell wall degrading enzymes mentioned in Examples XVI and XVII. It did not improve the activity of the enzymes except in the case of glucosidase from *T. harzianum* strain P1 where the ED$_{50}$ (dose effective to inhibit 50% of spore germination) was lowered about 1.5 fold.

The following applications were made to *B. cinerea*: (a) osmotin I alone; (b) osmotin I plus 1% sorbose; (c) osmotin I plus 3% sorbose; (d) osmotin I plus 1% L-sorbose and 10 μg/ml glucosidase from *T. harzianum* strain P1; and (e) osmotin I plus 1% L-sorbose and 2.5 μg/ml of endochitinase from *G. virens* strain 41. The sorbose concentrations are percentage of the reaction mixture on a weight/volume basis.

Figure 17:
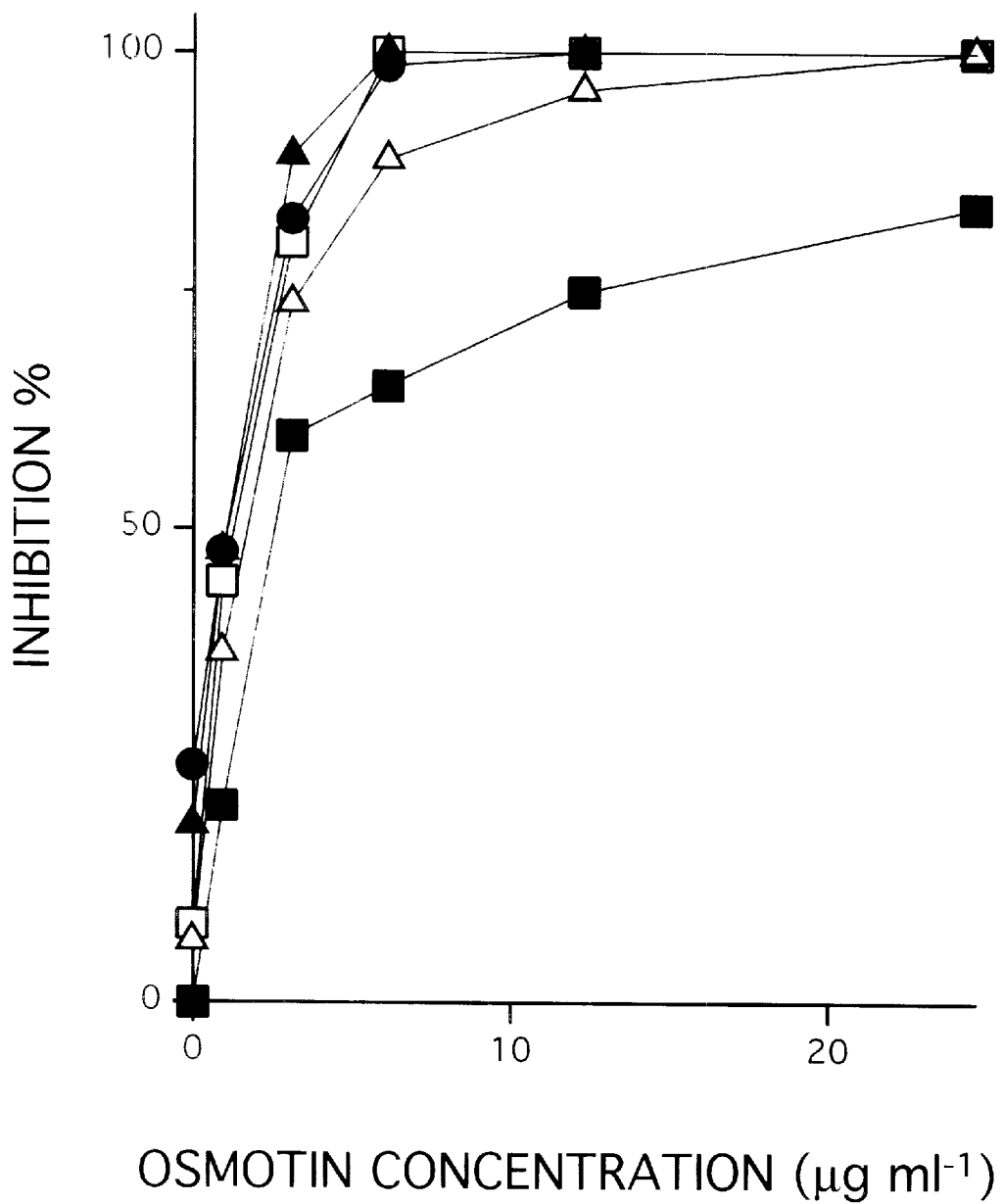
FIG. 17 is a set of graphs of osmotin concentration versus percent inhibition of spore germination of *B. cinerea* indicating the effect of application of L-sorbose and shows results of Example XVIII.

The results for (a)–(e) are shown in FIG. 17 wherein the filled in squares denote the data points for (a); the open triangles denote the data points for (b); the filled in circles denote the data points for (c); the filled in triangles denote the data points for (d); and the open squares denote the data points for (e).

Similar curves were obtained for other antifungal fungal cell membrane affecting compounds (flusilazole, gramicidin, valinomycin and trichorzianine A1 were additionally tested) together with L-sorbose and for antifungal fungal cell membrane affecting compounds together with L-sorbose and fungal cell wall degrading enzymes.

Similar curves were obtained when inhibition of germ tube elongation was determined rather than inhibition of spore germination.

Synergistic, in both inhibiting spore germination and in inhibiting germ tube elongation, were the combinations L-sorbose-antifungal fungal cell membrane affecting compound and L-sorbose-antifungal cell membrane affecting compound-fungal cell wall degrading enzyme. Instances of Ee and Eo values for the inhibition of spore germination were 17 and 50%, respectively, for the combination L-sorbose-trichorzianine A1; and 10 and 50%, respectively, for the combination L-sorbose-trichorzianine A1-glucosidase from *T. harzianum* strain P1.

EXAMPLE XIX

Data for inhibition of germ tube elongation was consistent with data for inhibition of spore germination obtained in Examples I–XV.

EXAMPLE XX

The gene (ThEn42) encoding endochitinase from *T. harzianum* strain P1 from genomic DNA, and whose exon sequence is provided in U.S. Pat. No. 5,378,821, was present as an insert in the plasmid pCRII (the original plasmid is available commercially from Invitrogen Corporation, San Diego, Calif.). This sequence was removed from the pCRII vector by restriction digestion and ligated into pBI121 (Clontech Laboratories, Palo Alto, Cailf.). Plasmid pBI121 contains the cauliflower mosaic virus 35S promoter which drives expression in higher plants, the NPT II gene for kanamycin resistance necessary for selection of transformed plants, and also a gene encoding β-glucuronidase. This plasmid was digested with the restriction enzymes BamH I and EcoR I; this linearized the plasmid and excised the gene encoding β-glucuronidase. ThEn42 was obtained from the plasmid containing it by the following procedure: The plasmid was linearized by restriction with BamH I, since pCRII contains unique site just upstream from the ThEn42 gene. There were two restriction sites for EcoR I in the plasmid. One was very near the 5' end of the endochitinase gene, in the untranslated region, and the other was just downstream from the 3' end of the gene. Therefore, a partial digest with EcoR I was done of the linearized plasmid, and the fragment that was the size of the full gene, including the untranslated region, was obtained following electrophoresis and electroelution. The isolated ThEn42 gene and the linear pBI121 plasmid therefore had both EcoR I and BamH I sticky ends. The gene and linear plasmid were then mixed and ligated together, and the orientation of the sticky ends was such that only correct orientation of the gene relative to the 35S promoter was possible. Once the ligation was complete, the presence of the gene in the recircularized plasmid was verified by polymerase chain reaction with appropriate primers. Similar procedures could be used to place ThEn42 in other plasmids behind other promoters known to those skilled in the art. The plasmid so obtained (p35S-ThEn42) was used to transform either *E. coli* to maintain it, or into *Agrobacterium tumifaciens* for plant transformation.

The plasmid so obtained can be used to transform a variety of plants to contain and express ThEn42. This specific example deals with tobacco. Agrobacterium-mediated transformation (*Agrobacterium tumefaciens* strain LBA4404 was used) of *Nicotiana tabacum* var Samsum NN leaf disks was carried out as described in the following reference (Horsh, R. B., Fry, J. E., Hoffman, N. C. Eichhltz, D., Rogers, S. G. and Fraley, R. T. 1985. A simple and general method for transferring genes into plants. Science. 227: 1229–1231). Kanamycin resistant plantlets were scored for their ability to form roots in two consecutive steps of propagation in Murashige-Skoog (MS) medium containing 3% (w/v) sucrose and 100 mg per liter of kanamycin sulfate, and full plants were regenerated from those which formed roots.

Expression of active endochitinase can be detected in extracts from transformed plants using standard enzyme assays (see U.S. Pat. No. 5,173,419) using either the methylumbelliferyl or the nitrophenyl derivatives of N,N',N" tri-acetylchitotriose. The expression of the transgenic endochitinase was demonstrated in transformed tobacco by assay with the methylumbelliferyl substrate. The expressed endochitinase was found to be present in an amount of 1–3% of total cellular protein.

The enzyme so expressed in the plant can then be admixed with membrane active compounds if such compounds are taken up and translocated within the plant. As an example, flusilazole is formulated into the commercial fungicide NuStar (E. I duPont Co., Newark, Del.). Therefore, transgenic plants can be sprayed with the fungicide either according to the label rates, or preferably at 0.5 or 0.1 times the recommended rate. Once plants transgenic plants are treated with the fungicide, the enzyme and fungicide will be present as a synergistic mixture within the plant.

Results of the examples show the reduction of the quantity of the antifungal fungal cell membrane affecting compounds necessary to obtain any level of inhibition when such compounds were used in combination with the fungal cell wall degrading enzymes tested.

*Trichoderma harzianum* strain P1 was deposited on May 20, 1991 at the American Type Culture Collection and was assigned accession number ATCC 74058. *Gliocladium virens* strain 041 was deposited on Oct. 24, 1988 at the American Type Culture Collection and was assigned accession number ATCC 20906. *Streptomyces albidoflavus* NRRL B-16746 (also known as strain 10) was deposited on Feb. 28, 1996 at the American Type Culture Collection and was assigned accession number ATCC 55742. The American Type Culture Collection is located at 12301 Parklawn Drive, Rockville, Md. 20852, U.S.A. *Nicotiana tabacum* cv. Havana 425 was deposited in the USDA Plant Introduction inventory in 1961 under accession number PI 552350 and is maintained in the Tobacco Collection (Curator: Verne A. Sisson, Crop Science Department, North Carolina State University, Oxford Tobacco Research Station, P.O. Box 1555, Oxford, N.C. 27565).

Variations in the invention will be obvious to those skilled in the art. Therefore, the invention is defined by the claims.

What is claimed is:

1. A transgenic plant transformed with a DNA molecule encoding a fungal cell wall degrading enzyme, wherein the enzyme is selected from the group consisting of Trichoderma endochitinase and Trichoderma β-N-acetylglucosaminidase and the transgenic plant is more fungal resistant than an untransformed form of the plant.

2. The transgenic plant according to claim 1, wherein said cell wall degrading enzyme is Trichoderma endochitinase.

3. The transgenic plant according to claim 1, wherein the cell wall degrading enzyme is from *Trichoderma harzianum*.

4. The transgenic plant according to claim 1, wherein said cell wall degrading enzyme is Trichoderma β-N-acetylglucosaminidase.

5. A method of enhancing fungal resistance in a plant comprising:

transforming the plant with a DNA molecule encoding a fungal cell wall degrading enzyme, wherein the enzyme is selected from the group consisting of Trichoderma endochitinase and Trichoderma β-N-acetylglucosaminidase under conditions effective to make the transformed plant more fungal resistant than an untransformed form of the plant.

6. The method according to claim 5, wherein said cell wall degrading enzyme is Trichoderma endochitinase.

7. The method according to claim 5, wherein the cell wall degrading enzyme is from *Trichoderma harzianum*.

8. The method according to claim 5, wherein said cell wall degrading enzyme is Trichoderma β-N-acetylglucosaminidase.

9. A method of enhancing fungal resistance in a plant comprising:

transforming the plant with a DNA molecule encoding a fungal cell wall degrading enzyme wherein the enzyme is selected from the group consisting of Trichoderma endochitinase and Trichoderma β-N-acetylglucosaminidase under conditions effective to make the transformed plant more fungal resistant than an untransformed form of the plant and applying to the plant an antifungal fungal cell membrane affecting compound, wherein the antifungal fungal cell membrane affecting compound is selected from the group consisting of a sterol synthesis inhibiting fungicide, zeamatin, a protein serologically related to zeamatin, valinomycin, gramicidin, a peptaibol, and a mixture thereof.

10. The method according to claim 9, wherein the antifungal fungal cell membrane affecting compound is a sterol synthesis inhibiting fungicide.

11. The method according to claim 9, wherein the antifungal fungal cell membrane affecting compound is zeamatin or a protein serologically related to zeamatin.

12. The method according to claim 9, wherein the antifungal fungal cell membrane affecting compound is valinomycin, gramicidin, or a peptaibol.

13. The method according to claim 9, wherein said cell wall degrading enzyme is Trichoderma endochitinase.

14. The method according to claim 9, wherein the antifungal fungal cell membrane affecting compound is applied with a carrier.

15. The method according to claim 9, further comprising:
   applying to the plant a material selected from the group consisting of an antifungal polyene macrolide antibiotic, an antifungal epithiodiketopiperizine chitin synthetase inhibitor, a β-1,3-glucan synthetase inhibitor, a detergent, and a mixture thereof.

16. The method according to claim 9, wherein the cell wall degrading enzyme is from *Trichoderma harzianum*.

17. The method according to claim 9, wherein said cell wall degrading enzyme is Trichoderma β-N-acetylglucosaminidase.

* * * * *